(12) United States Patent
Yasuno et al.

(10) Patent No.: US 12,387,837 B2
(45) Date of Patent: Aug. 12, 2025

(54) METHOD OF PROCESSING OPHTHALMIC DATA, OPHTHALMIC DATA PROCESSING APPARATUS, AND OPHTHALMIC EXAMINATION APPARATUS

(71) Applicants: University of Tsukuba, Ibaraki (JP); Topcon Corporation, Tokyo (JP)

(72) Inventors: Yoshiaki Yasuno, Tsukuba (JP); Shuichi Makita, Tsukuba (JP); Tatsuo Yamaguchi, Warabi (JP); Shinnosuke Azuma, Tokyo (JP)

(73) Assignees: UNIVERSITY OF TSUKUBA, Tsukuba (JP); TOPCON CORPORATION, Tokyo (JP)

( * ) Notice: Subject to any disclaimer, the term of this patent is extended or adjusted under 35 U.S.C. 154(b) by 748 days.

(21) Appl. No.: 17/683,379

(22) Filed: Mar. 1, 2022

(65) Prior Publication Data

US 2022/0273170 A1 Sep. 1, 2022

(30) Foreign Application Priority Data

Mar. 1, 2021 (JP) ................. 2021-031618

(51) Int. Cl.
*G16H 30/40* (2018.01)
*A61B 3/113* (2006.01)
(Continued)

(52) U.S. Cl.
CPC ............. *G16H 30/40* (2018.01); *A61B 3/113* (2013.01); *G06N 20/00* (2019.01); *G16H 30/20* (2018.01);
(Continued)

(58) Field of Classification Search
CPC ........ G16H 30/40; G16H 30/20; G16H 50/20; G16H 40/63; G16H 50/70; A61B 3/113;
(Continued)

(56) References Cited

U.S. PATENT DOCUMENTS

| 2006/0164653 A1 | 7/2006 | Everett et al. |
| 2008/0221819 A1 | 9/2008 | Everett et al. |

(Continued)

FOREIGN PATENT DOCUMENTS

| JP | 2007-130403 A | 5/2007 |
| JP | 2008528954 A | 7/2008 |

(Continued)

OTHER PUBLICATIONS

Chen et al., "Three-dimensional Eye Motion Correction by Lissajous Scan Optical Coherence Tomography", Biomedical Optics Express, vol. 8, No. 3, Mar. 1, 2017, pp. 1783-1802.

(Continued)

*Primary Examiner* — Vu Le
*Assistant Examiner* — Rachel Anne Ometz
(74) *Attorney, Agent, or Firm* — XSENSUS LLP

(57) ABSTRACT

A method of processing ophthalmic data of some embodiment examples includes preparing a data set acquired by applying optical scanning of a two-dimensional pattern to a subject's eye. The two-dimensional pattern of the optical scanning includes a series of cycles that intersects each other. The method further includes generating position history data based on the data set. The position history data represents a temporal change in a position of the subject's eye.

21 Claims, 23 Drawing Sheets

(51) Int. Cl.
*G06N 20/00* (2019.01)
*G06T 7/20* (2017.01)
*G06T 7/215* (2017.01)
*G06T 11/00* (2006.01)
*G16H 30/20* (2018.01)
*G16H 50/20* (2018.01)

(52) U.S. Cl.
CPC .............. *G06T 7/20* (2013.01); *G06T 7/215* (2017.01); *G06T 11/003* (2013.01); *G06T 2207/10101* (2013.01); *G06T 2207/30041* (2013.01); *G16H 50/20* (2018.01)

(58) Field of Classification Search
CPC ........ A61B 3/102; G06N 20/00; G06N 3/045; G06N 3/044; G06N 3/08; G06N 20/10; G06T 7/20; G06T 7/215; G06T 11/003; G06T 2207/10101; G06T 2207/30041
See application file for complete search history.

(56) References Cited

U.S. PATENT DOCUMENTS

| | | | |
|---|---|---|---|
| 2010/0142780 A1 | 6/2010 | Yasuno et al. | |
| 2010/0245838 A1 | 9/2010 | Everett et al. | |
| 2010/0284021 A1* | 11/2010 | Hacker | G01B 9/02028 356/497 |
| 2011/0267340 A1* | 11/2011 | Kraus | A61B 3/102 345/419 |
| 2012/0140175 A1 | 6/2012 | Everett et al. | |
| 2012/0249956 A1* | 10/2012 | Narasimha-Iyer | A61B 5/0066 351/246 |
| 2013/0301008 A1 | 11/2013 | Srivastava et al. | |
| 2014/0240670 A1 | 8/2014 | Everett et al. | |
| 2015/0085252 A1 | 3/2015 | Fujimura et al. | |
| 2016/0106314 A1 | 4/2016 | Everett et al. | |
| 2016/0317029 A1 | 11/2016 | Srivastava et al. | |
| 2016/0345822 A1 | 12/2016 | Fujimura et al. | |
| 2017/0258317 A1* | 9/2017 | Bajraszewski | A61B 3/0025 |
| 2018/0116501 A1* | 5/2018 | Akiba | G01N 21/17 |
| 2018/0242839 A1 | 8/2018 | Fukuhara et al. | |
| 2018/0303339 A1* | 10/2018 | Moriguchi | A61B 3/152 |
| 2019/0272641 A1* | 9/2019 | Akama | G06T 3/20 |
| 2021/0353139 A1* | 11/2021 | Wagner | G06T 7/30 |
| 2023/0022601 A1* | 1/2023 | Grillini | A61B 3/024 |

FOREIGN PATENT DOCUMENTS

| | | |
|---|---|---|
| JP | 2013-248376 A | 12/2013 |
| JP | 2015-515894 A | 6/2015 |
| JP | 2016-17915 A | 2/2016 |
| JP | 2016-49243 A | 4/2016 |
| JP | 2018-68578 A | 5/2018 |
| JP | 2018068578 A * | 5/2018 |
| JP | 2018-140004 A | 9/2018 |
| JP | 2018-140049 A | 9/2018 |
| JP | 2022507284 A | 1/2022 |
| WO | 2020115052 A1 | 6/2020 |

OTHER PUBLICATIONS

Chen et al., "Eye-Motion-Corrected Optical Coherence Tomography Angiography Using Lissajous Scanning", Biomedical Optics Express, vol. 9, No. 3, Mar. 1, 2018, pp. 1111-1129.

Kinkelder et al., "Heartbeat-Induced Axial Motion Artifacts in Optical Coherence Tomography Measurements of the Retina", Investigative Ophthalmology & Visual Science, vol. 52, No. 6, May 2011, pp. 3908-3913.

Japanese Office Action issued Aug. 20, 2024, in corresponding Japanese Patent Application No. 2021-031618, 10pp.

* cited by examiner

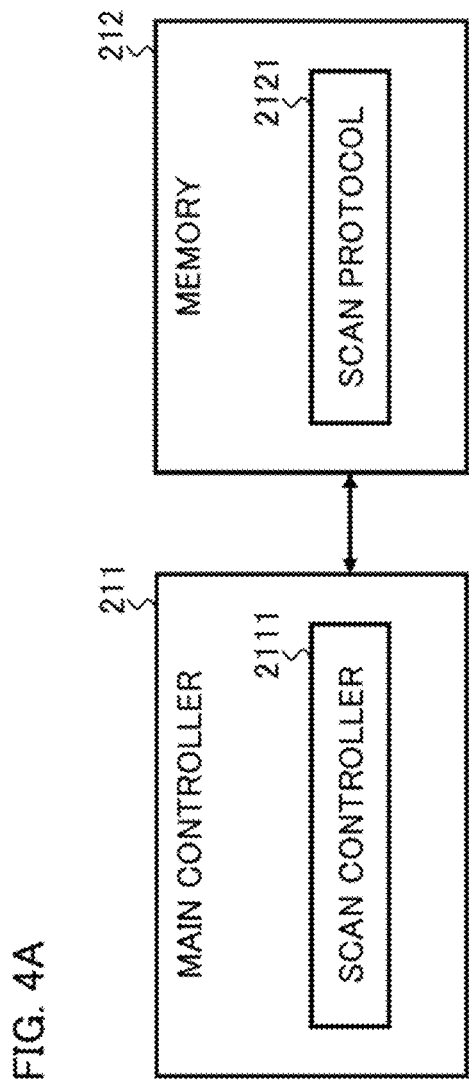

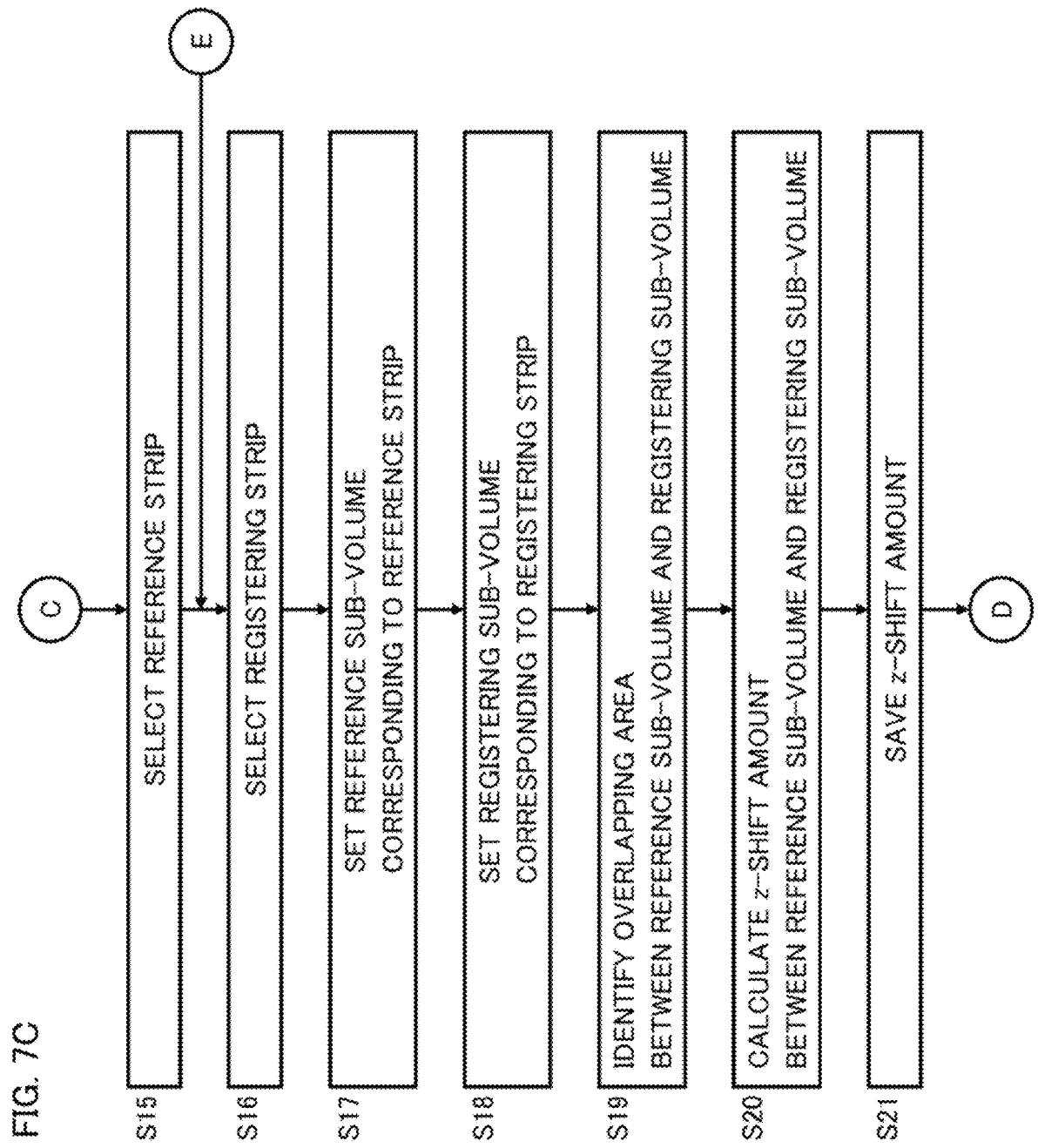

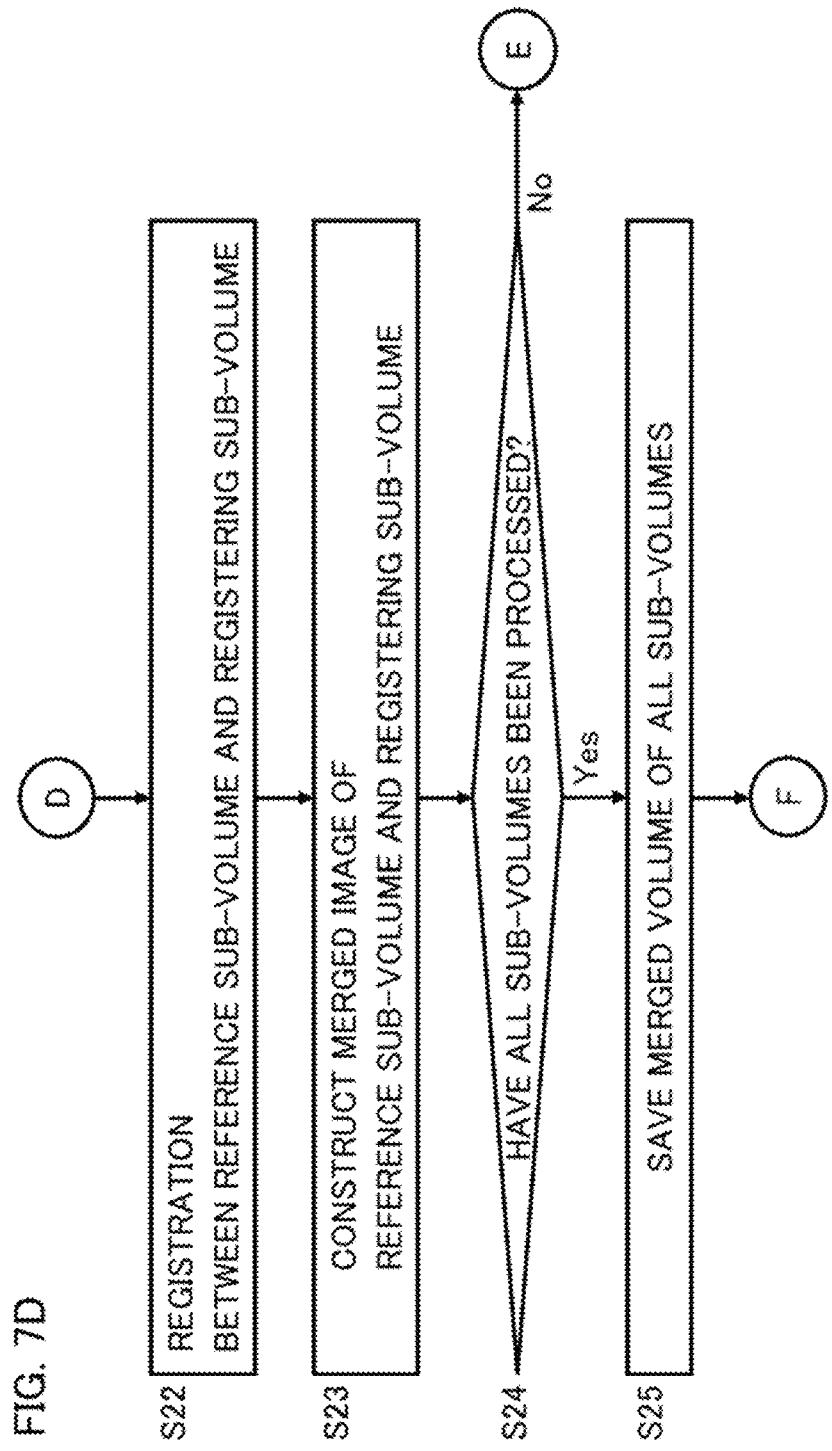

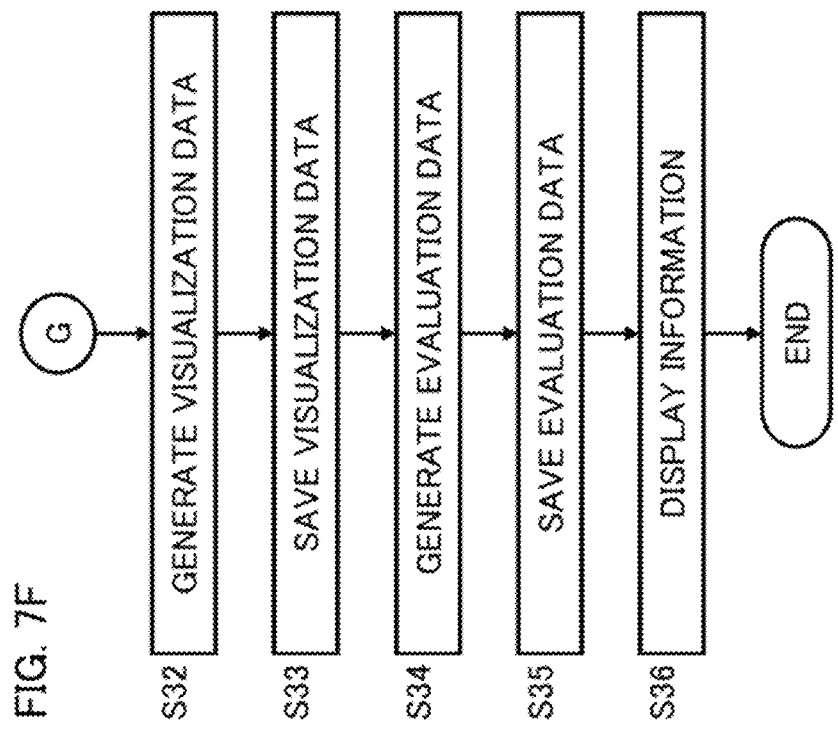

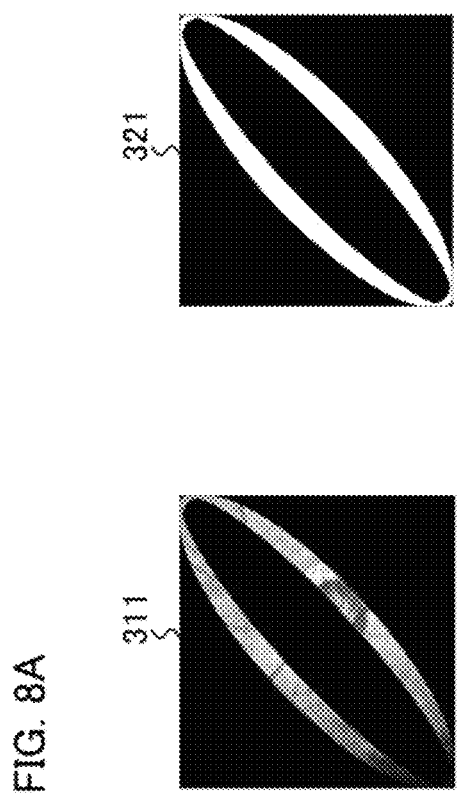

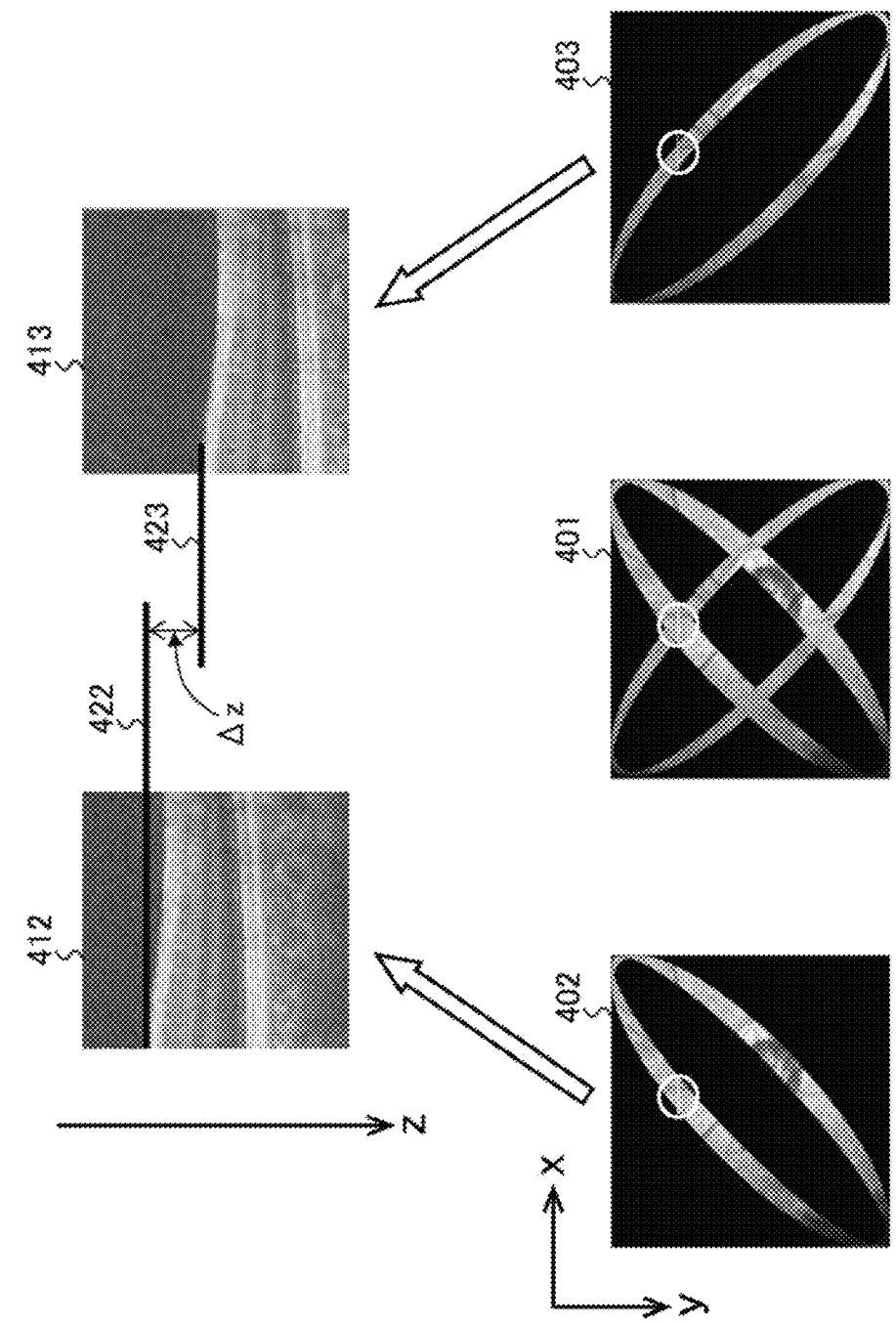

METHOD OF PROCESSING OPHTHALMIC DATA, OPHTHALMIC DATA PROCESSING APPARATUS, AND OPHTHALMIC EXAMINATION APPARATUS

CROSS-REFERENCE TO RELATED APPLICATION

This application is based upon and claims the benefit of priority from Japanese Patent Application No. 2021-031618, filed Mar. 1, 2021; the entire contents of which are incorporated herein by reference.

TECHNICAL FIELD

The present disclosure relates to a method of processing ophthalmic data, an ophthalmic data processing apparatus, and an ophthalmic examination apparatus.

BACKGROUND OF THE INVENTION

Various imaging techniques have been applied in ophthalmology and one of the imaging techniques is scanning imaging. The scanning imaging is a technique of collecting data by projecting beams sequentially onto a plurality of positions of a sample and constructing an image of the sample from the collected data.

Optical coherence tomography (OCT) is an example of scanning imaging using light. OCT is a technique that is capable of measuring and imaging light scattering media at a micrometer level or higher resolution. OCT has been applied to various fields including medical imaging and non-destructive testing. OCT is a technique based on low-coherence interferometry, and typically utilizes probe light (measurement light) in the near-infrared region in order to achieve deep penetration into the sample of a light scattering medium. In the field of ophthalmology, the use of near-infrared light also has advantages such as preventing the subject's eye from following the movement of the measurement light and preventing pupil contraction.

OCT systems has been becoming increasingly popular in ophthalmic diagnostic imaging, and are used not only for two-dimensional imaging but also for three-dimensional imaging, rendering, structural analysis, functional analysis, and other applications. OCT systems have become a powerful tool for ophthalmic diagnosis. In the field of ophthalmology, scanning imaging other than OCT, such as scanning laser ophthalmoscopy (SLO), is also being used. In addition, scanning imaging using light (electromagnetic waves) in wavelengths other than the near-infrared region, or using ultrasound is also known.

There are various kinds of scanning modes used in OCT and SLO. Among various scanning modes, the so-called "Lissajous scanning" for motion artifact correction etc. has recently attracted attention. Lissajous scanning techniques are disclosed in the following documents, for example: Japanese Unexamined Patent Application Publication No. 2016-17915 (Patent document 1); Japanese Unexamined Patent Application Publication No. 2018-68578 (Patent document 2); Japanese Unexamined Patent Application Publication No. 2018-140004 (Patent document 3); Japanese Unexamined Patent Application Publication No. 2018-140049 (Patent document 4); Yiwei Chen, Young-Joo Hong, Shuichi Makita, and Yoshiaki Yasuno, "Three-dimensional eye motion correction by Lissajous scan optical coherence tomography", Biomedical Optics EXPRESS, Vol. 8, No. 3, 1 Mar. 2017, PP. 1783-1802 (Non-patent document 1); Yiwei Chen, Young-Joo Hong, Shuichi Makita, and Yoshiaki Yasuno, "Eye-motion-corrected optical coherence tomography angiography using Lissajous scanning", Biomedical Optics EXPRESS, Vol. 9, No. 3, 1 Mar. 2018, PP. 1111-1129 (Non-patent document 2).

Typically, Lissajous scanning is performed by rapidly moving the measurement light to sequentially draw a plurality of loops (referred to as cycles) of certain sizes, so that the differences between time points of data acquisition from many positions on one cycle can be practically ignored. In addition, since typical Lissajous scanning is capable of performing registration between the cycles by using overlapping areas of different cycles as references, artifacts caused by movement of the sample can be corrected. Focusing on these features, Lissajous scanning is used to address motion artifacts induced by eye movements in the field of ophthalmology.

The technique described in Non-patent document 1 is configured to divide a data set collected by Lissajous scanning into a plurality of sub-volumes, in each of which no relatively significant motion can be considered to exist, and construct an en face projection from each of the sub-volumes. These en face projections are referred to as strips. Performing registration of these strips yields an image with motion artifacts corrected.

Lissajous scanning has a property that any two strips overlap (intersect) in four places. In the image processing described in Non-patent document 1, a strip with the largest dimensions (the largest size) is selected as an initial reference strip, and a plurality of strips ordered by size is sequentially (recursively) registered and merged with the initial reference strip. This registration uses cross-correlation functions to find the relative position between a reference strip and another strip. Since the shapes of the strips are not uniform, correlation calculation of an overlapping area between strips is performed using a mask configured to transform individual strips into images of the same shape such as images of square shape (See Appendix A of Non-patent document 1).

BRIEF SUMMARY OF THE INVENTION

A method of processing ophthalmic data of some embodiment examples includes preparing a data set acquired by applying optical scanning of a two-dimensional pattern to a subject's eye. The two-dimensional pattern includes a series of cycles that intersects each other. The method further includes generating position history data based on the data set. The position history data represents a temporal change in a position of the subject's eye.

BRIEF DESCRIPTION OF THE SEVERAL VIEWS OF THE DRAWING

FIG. 4A illustrates an example of the configuration of an ophthalmic examination apparatus according to the present disclosure.

FIG. 7C illustrates a flowchart of an example of the operation of an ophthalmic examination apparatus according to the present disclosure.

FIG. 7D illustrates a flowchart of an example of the operation of an ophthalmic examination apparatus according to the present disclosure.

FIG. 7F illustrates a flowchart of an example of the operation of an ophthalmic examination apparatus according to the present disclosure.

FIG. 8A illustrates a description of an example of the operation of an ophthalmic examination apparatus according to the present disclosure.

FIG. 9 illustrates a description of an example of the operation of an ophthalmic examination apparatus according to the present disclosure.

DETAILED DESCRIPTION OF THE INVENTION

Figure 1:
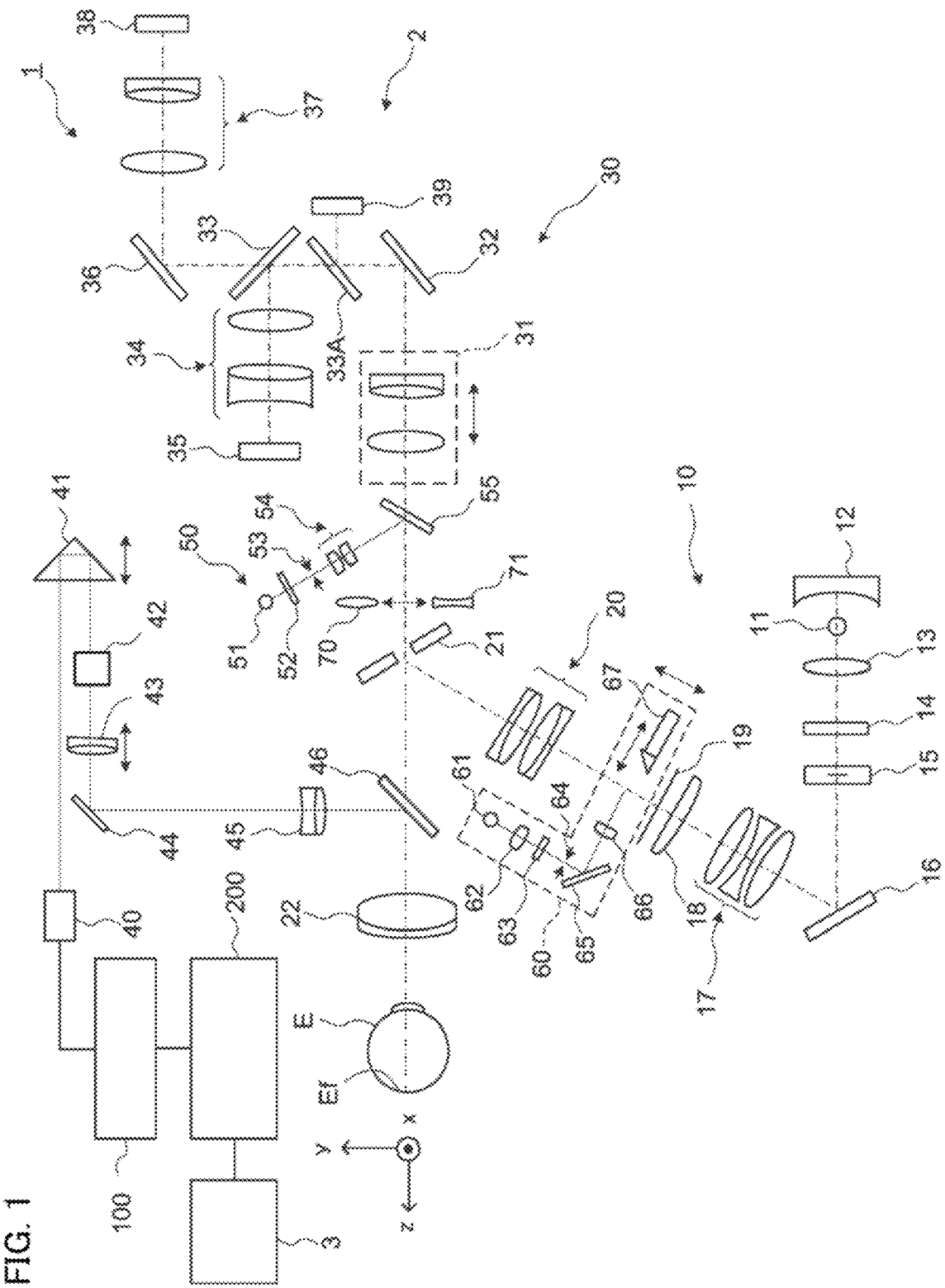
FIG. 1 illustrates an example of the configuration of an ophthalmic examination apparatus according to the present disclosure.

The present disclosure describes several aspect examples of embodiments with reference to the drawings. The aspect examples described in the present disclosure include a method of processing ophthalmic data, an ophthalmic data processing apparatus, a method of controlling an ophthalmic data processing apparatus, an ophthalmic examination apparatus, a method of controlling an ophthalmic examination apparatus, a program, and a recording media. Embodiments are not limited to these aspects, and any applications can be implemented such as any applications to any medical departments other than ophthalmology, any applications to any medical methods or techniques such as diagnostic methods, and any applications to any fields other than medical fields (e.g., biology, non-destructive testing, etc.).

Any matters or items described in the present disclosure and any known technologies or techniques may be incorporated with the embodiment examples. Further, "image data" and an "image" formed based on this image data are not distinguished unless otherwise mentioned. In addition, a "site (part, tissue, etc.)" of a subject's eye and an "image" of this site are not distinguished unless otherwise mentioned.

The ophthalmic examination apparatus of some embodiment examples described below is configured to be capable of measuring and imaging the fundus of a living eye using Fourier domain OCT techniques (especially, swept source OCT techniques). The types of OCT techniques applicable to embodiments are not limited to swept source OCT. Spectral domain OCT or time domain OCT may also be applied to some embodiment examples.

The ophthalmic examination apparatus of some embodiment examples may be capable of employing any scanning modality other than OCT. Some embodiment examples may employ any optical scanning modality such as SLO.

Scanning modalities applicable to the ophthalmic examination apparatus of some embodiment examples may not be optical scanning modalities. Some embodiment examples may employ scanning modalities using electromagnetic waves or scanning modalities using ultrasound waves.

Some embodiment examples may be configured to be capable of performing not only processing of data collected using OCT scanning and/or processing of data collected using SLO scanning but also processing of data acquired by other modalities. The other modalities here may be any kinds of ophthalmic modalities such as fundus cameras, slit lamp microscopes, and ophthalmic surgical microscopes. The ophthalmic examination apparatus of some embodiment examples may have the functions of any of these modalities. The ophthalmic examination apparatus of some embodiment examples may have the stereo alignment function using two or more anterior segment cameras as disclosed in Japanese Unexamined Patent Application Publication No. 2013-248376 (United States Patent Application Publication No. 2015/0085252) and Japanese Unexamined Patent Application Publication No. 2016-49243.

Objects (samples) to which OCT is applied are not limited to eye fundi. The objects (samples) may be any sites of eyes such as anterior segments or vitreous bodies. The configuration and function of some embodiment examples may be applied to measurements or imaging of any sites (tissues, organs, parts) of living bodies other than eyes, or to measurements or imaging of any objects (with motion) other than living bodies or any parts thereof. In other words, the industrial fields of application of some embodiment examples are not limited to fields related to ophthalmology, and may include any fields related to medicine, veterinary medicine, biology, or the like. More generally, the industrial fields of application of some embodiment examples may include any fields related to any objects (samples) with local movements or motions and/or global movements or motions.

The embodiment examples described below includes some aspects of an ophthalmic examination apparatus, some aspects of a method of controlling an ophthalmic examination apparatus, some aspects of an ophthalmic data processing apparatus, some aspects of a method of controlling an ophthalmic data processing apparatus, some aspects of a method of processing ophthalmic data, some aspects of a program, and some aspects of a recording medium. These aspects are merely illustrative examples and are not intended to limit the invention.

<Configuration of Ophthalmic Examination Apparatus>

The ophthalmic examination apparatus 1 shown in FIG. 1 includes the fundus camera unit 2, the OCT unit 100, and the arithmetic and control unit 200. The fundus camera unit 2 is provided with an element group (e.g., optical elements, mechanisms, etc.) for photographing the subject's eye E from the front. The OCT unit 100 includes part of an element group (e.g., optical elements, mechanisms, etc.) for applying OCT scanning to the subject's eye E. Another part of the element group for OCT scanning is provided in the fundus camera unit 2. The arithmetic and control unit 200 includes one or more processors configured and programmed to execute various calculations and controls. In addition to these units, the ophthalmic examination apparatus 1 may also include elements for supporting the face of the subject and an element for switching target sites to which OCT scanning is applied. Examples of the elements for supporting the face of the subject include a chin rest and a forehead rest. Examples of the element for switching target sites to which OCT scanning is applied include a lens unit used to switch the target site from the fundus to the anterior segment.

At least one or more of the functions of the elements described in the present disclosure are implemented by using a circuit configuration (circuitry) or a processing circuit configuration (processing circuitry). The circuitry or the processing circuitry includes any of the followings, all of which are configured and/or programmed to execute at least one or more functions disclosed herein: a general purpose processor, a dedicated processor, an integrated circuit, a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), an existing or conventional circuit configuration or circuitry, and any combination of these. A processor is considered to be processing circuitry or circuitry that includes a transistor and/or another circuitry. In the present disclosure, circuitry, a unit, a means, or a term similar to these is hardware that executes at least one or more functions disclosed herein, or hardware that is programmed to execute at least one or more functions disclosed herein. Hardware may be the hardware disclosed herein, or alternatively, known hardware that is programmed and/or configured to execute at least one or more functions described herein. In the case where the hardware is a processor, which may be considered as a certain type of circuitry, then circuitry, a unit, a means, or a term similar to these is a combination of hardware and software. In this case, the software is used to configure the hardware and/or the processor.

<Fundus Camera Unit 2>

The fundus camera unit 2 is provided with an optical system for photographing the fundus Ef of the subject's eye E. Images of the fundus Ef acquired by the fundus camera unit 2 (referred to as fundus images, fundus photographs, or the like) are front images (en face images) such as observation images and photographed images. An observation image is obtained, for example, by capturing a moving image using near-infrared light, and may be used for alignment, focusing, tracking, and any other operations. A photographed image is a still image obtained using flash light in the visible region or infrared region, for example.

The fundus camera unit 2 includes the illumination optical system 10 and the photographing optical system 30. The illumination optical system 10 projects illumination light onto the subject's eye E. The photographing optical system 30 detects return light of the illumination light from the subject's eye E. Measurement light input from the OCT unit 100 is directed to the subject's eye E through the optical path in the fundus camera unit 2, and return light of this measurement light from the subject's eye E is directed to the OCT unit 100 through the same optical path.

Light emitted by the observation light source 11 of the illumination optical system 10 (referred to as observation illumination light) is reflected by the concave mirror 12, passes through the condenser lens 13, and becomes near-infrared light after passing through the visible cut filter 14. Further, the observation illumination light is once converged at a location near the photographing light source 15, reflected by the mirror 16, and passes through the relay lens system 17, the relay lens 18, the diaphragm 19, and the relay lens system 20. Then, the observation illumination light is reflected on the peripheral part (i.e., the area surrounding the aperture part) of the aperture mirror 21, penetrates the dichroic mirror 46, and refracted by the objective lens 22, thereby illuminating the subject's eye E (the fundus Ef). Return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Furthermore, the return light passes through the half mirror 33A, is reflected by the dichroic mirror 33, and forms an image on the light receiving surface of the image sensor 35 by the imaging lens 34. The image sensor 35 detects the return light at a predetermined frame rate. The photographing optical system 30 is adjusted to be focused on the fundus Ef or the anterior eye segment.

Light emitted by the photographing light source 15 (referred to as photographing illumination light) passes through the same route as the route of the observation illumination light and is projected onto the fundus Ef. Return light of the photographing illumination light from the subject's eye E passes through the same route as the route of the return light of the observation illumination light to the dichroic mirror 33, passes through the dichroic mirror 33, is reflected by the mirror 36, and forms an image on the light receiving surface of the image sensor 38 by the imaging lens 37.

The liquid crystal display (LCD) 39 displays a fixation target (fixation target image). Part of a light beam output from the LCD 39 is reflected by the half mirror 33A and the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef. Varying the display position of the fixation target image on the LCD 39 changes the direction in which the line of sight of the subject's eye E is guided (fixation direction, fixation position). In some aspect examples, a light emitting element array or a combination of a light emitting element and a mechanism for moving this light emitting element may be used in place of a display device such as the LCD 39.

The alignment optical system 50 generates an alignment indicator used for alignment operations of the optical system with respect to the subject's eye E. Alignment light output from the light emitting diode (LED) 51 travels through the diaphragm 52, the diaphragm 53, and the relay lens 54, is reflected by the dichroic mirror 55, passes through the aperture part of the aperture mirror 21, penetrates the dichroic mirror 46, and is projected onto the subject's eye E via the objective lens 22. Return light of the alignment light from the subject's eye E (e.g., corneal reflection light) passes through the same route as the route of the return light of the observation illumination light and is guided to the image sensor 35. Manual alignment and/or automatic alignment may be carried out using an image detected by the image sensor 35 (alignment indicator image).

As in existing or conventional techniques, the alignment indicator image of the present example includes two bright spot images whose positions change depending on alignment states. When the relative position between the subject's eye E and the optical system changes in the xy direction, the two bright spot images are shifted together in the xy direction. When the relative position between the subject's eye E and the optical system changes in the z direction, the relative position (distance) between the two bright spot images changes. When the distance between the subject's eye E and the optical system in the z direction matches with a working distance set in advance, the two bright spot images overlap each other. When the position of the subject's eye E matches with the position of the optical system in the xy direction, the two bright spot images are located within or near a given alignment target. When the distance between the subject's eye E and the optical system in the z direction matches with the working distance as well as the position of the subject's eye E matches with the position of the optical system in the xy direction, the two bright spot images overlap each other and are presented within the alignment target.

For automatic alignment, the data processor 230 detects the positions of the two bright spot images, and the main controller 211 controls the movement mechanism 150 (described later) on the basis of the positional relationship between the two bright spot images and the alignment target. For manual alignment, the main controller 211 displays the two bright spot images together with the observation image of the subject's eye E on the display 241, and the user operates the movement mechanism 150 using the operation device 242 while monitoring the two bright spot images displayed.

The focusing optical system 60 generates a split indicator used for focus adjustment with respect to the subject's eye E. The focusing optical system 60 is moved along the optical path of the illumination optical system 10 in conjunction with the movement of the photography focusing lens 31 along the optical path of the photographing optical system 30. The optical path of the illumination optical system 10 is referred to as the illumination optical path, and the optical path of the photographing optical system 30 is referred to as the photographing optical path. The reflection rod 67 is inserted into and removed from the illumination optical path. The reflective surface of the reflection rod 67 is inserted into the illumination optical path and placed in a slanted position before performing focus adjustment. Focus light emitted from the LED 61 passes through the relay lens 62, is split into two light beams by the split indicator plate 63, and passes through the two-hole diaphragm 64. The focus light, then, is reflected by the mirror 65, is converged on the reflective surface of the reflection rod 67 by the condenser lens 66, and is reflected by the reflective surface.

Further, the focus light travels through the relay lens 20, is reflected by the aperture mirror 21, and penetrates the dichroic mirror 46, thereby being projected onto the subject's eye E via the objective lens 22. Return light of the focus light from the subject's eye E (e.g., fundus reflection light, etc.) passes through the same route as the route of the return light of the alignment light and is guided to the image sensor 35. Manual focusing and/or automatic focusing may be carried out using an image detected by the image sensor 35 (split indicator image).

The diopter correction lenses 70 and 71 can be selectively inserted into the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for fundus photography and the optical path for OCT scanning. This optical path for OCT scanning is referred to as the sample arm. The dichroic mirror 46 reflects light of wavelength bands used for OCT scanning while transmitting light for fundus photography. Listed from the OCT unit 100 side, the sample arm includes the collimator lens unit 40, the retroreflector 41, the dispersion compensation member 42, the OCT focusing lens 43, the optical scanner 44, and the relay lens 45.

The retroreflector 41 is movable in the directions indicated by the arrow in FIG. 1, whereby the length of the sample arm is changed. This change in the sample arm length may be used for any operations such as optical path length correction based on eye axial length and adjustment or regulation of interference conditions or states.

The dispersion compensation member 42, together with the dispersion compensation member 113 (described later) arranged in the reference arm, acts to equalize the dispersion characteristics of the measurement light LS and the dispersion characteristics of the reference light LR with each other.

The OCT focusing lens 43 is moved along the sample arm in order to perform focus adjustment of the sample arm. The movement of the photography focusing lens 31, the movement of the focusing optical system 60, and the movement of the OCT focusing lens 43 may be controlled in an interlocking manner.

The optical scanner 44 is placed substantially at a position optically conjugate with the pupil of the subject's eye E. The optical scanner 44 deflects the measurement light LS guided by the sample arm. The optical scanner 44 of some examples may be a galvanometer scanner that is capable of performing two-dimensional scanning. This galvanometer scanner may include a galvanometer mirror for performing scanning in the x direction and a galvanometer mirror for performing scanning in the y direction.

<OCT Unit 100>

Figure 2:
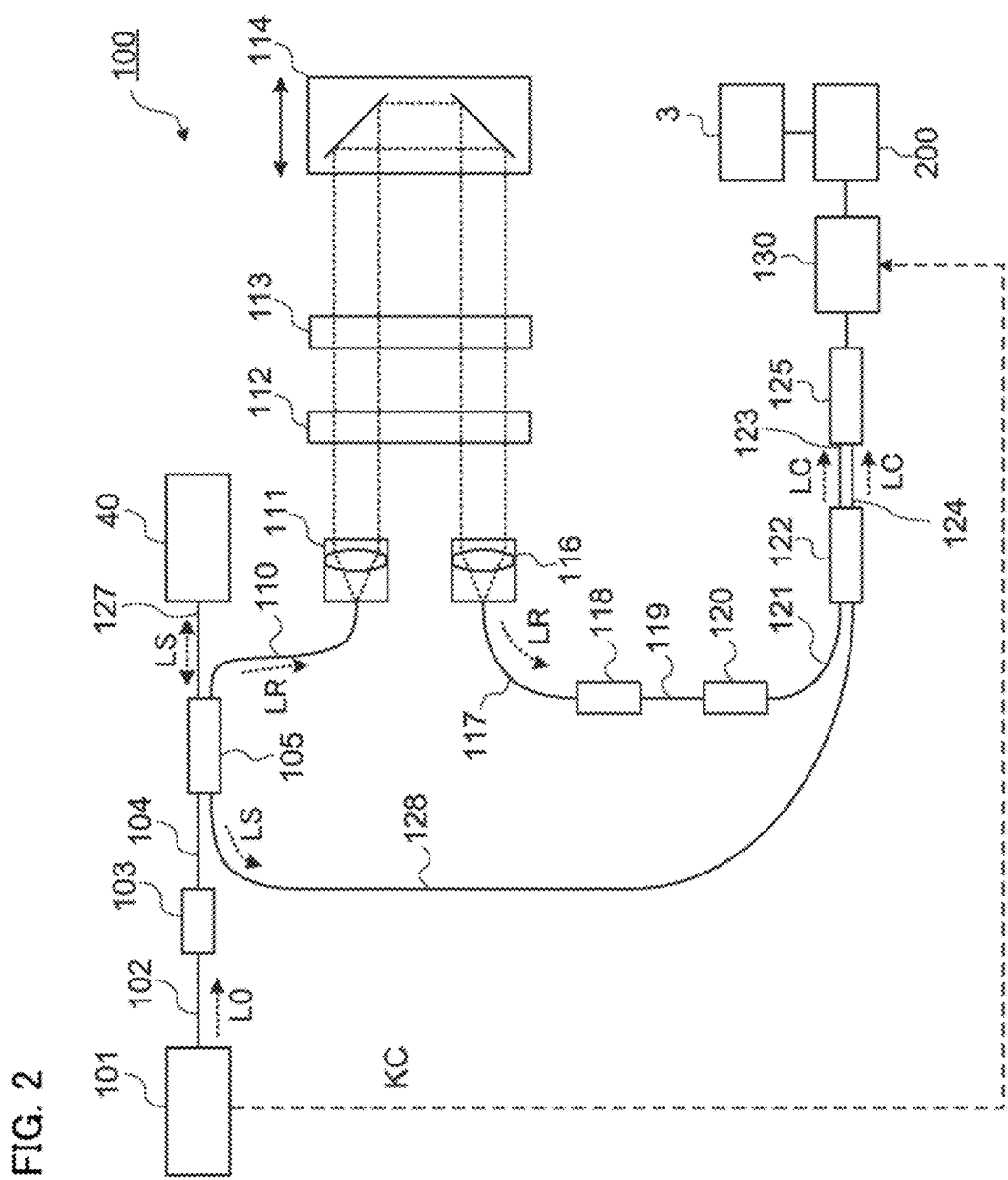
FIG. 2 illustrates an example of the configuration of an ophthalmic examination apparatus according to the present disclosure.
Figure 3:
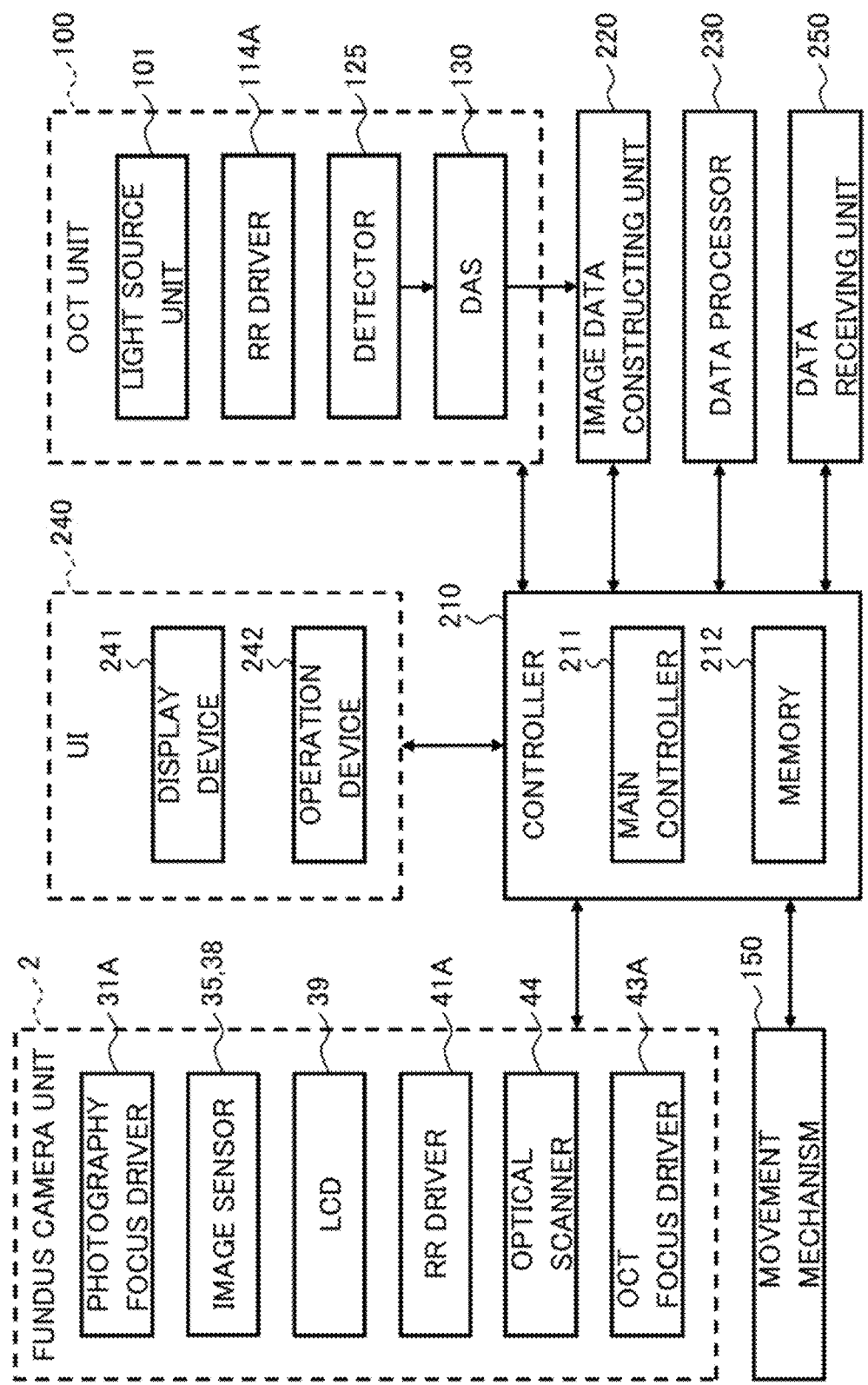
FIG. 3 illustrates an example of the configuration of an ophthalmic examination apparatus according to the present disclosure.

As illustrated in FIG. 2, the OCT unit 100 is provided with an optical system for performing swept source OCT. This optical system includes an interference optical system. This interference optical system is configured to split light emitted from a wavelength tunable light source (wavelength sweeping light source) into measurement light and reference light, superpose return light of the measurement light that has been guided to the subject's eye E by the sample arm on the reference light that has been guided by the reference arm to generate interference light, and detect this interference light. Data obtained by the interference optical system in this way (detection signal) is a signal representing a spectrum of the interference light. This detection signal is sent to the arithmetic and control unit 200.

The light source unit 101 of some examples includes a near-infrared wavelength tunable laser configured to vary the wavelengths of emitted light at high speed at least in the near-infrared wavelength region. The light LO output from the light source unit 101 is guided to the polarization controller 103 through the optical fiber 102, and the polarization state of the light LO is regulated by the polarization controller 103. Further, the light LO is guided to the fiber coupler 105 through the optical fiber 104 and then split into the measurement light LS and the reference light LR. The optical path of the measurement light LS is referred to as the sample arm, and the optical path of the reference light LR is referred to as the reference arm.

The reference light LR is guided through the optical fiber 110 to the collimator 111, is converted into a parallel light beam by the collimator 111, travels through the optical path length correction member 112 and the dispersion compensation member 113, and is guided to the retroreflector 114. The optical path length correction member 112 acts to equalize the optical path length of the reference light LR and the optical path length of the measurement light LS with each other. The dispersion compensation member 113 acts to equalize the dispersion characteristics of the reference light LR and the dispersion characteristics of the measurement light LS with each other, together with the dispersion compensation member 42 provided in the sample arm. The retroreflector 114 is movable along the optical path of the reference light LR that is incident onto the retroreflector 114. With this, the length of the reference arm is changed. This change in the reference arm length may be used for any operations such as optical path length correction based on eye axial length and adjustment or regulation of interference conditions or states.

The reference light LR that has passed through the retroreflector 114 travels through the dispersion compensation member 113 and the optical path length correction member 112, is converted from a parallel light beam to a convergent light beam by the collimator 116, and enters the optical fiber 117. The reference light LR that has entered the optical fiber 117 is guided to the polarization controller 118, and the polarization state of the reference light LR is regulated by the polarization controller 118. Then, the reference light LR is guided to the attenuator 120 through the optical fiber 119, and the light amount of the reference light LR is regulated by the attenuator 120. Subsequently, the reference light LR is guided to the fiber coupler 122 through the optical fiber 121.

Meanwhile, the measurement light LS generated by the fiber coupler 105 is guided through the optical fiber 127 and is converted to a parallel light beam by the collimator lens unit 40. Then, the measurement light LS passes through the retroreflector 41, the dispersion compensation member 42, the OCT focusing lens 43, the optical scanner 44, and the relay lens 45, is reflected by the dichroic mirror 46, is refracted by the objective lens 22, and is projected onto the subject's eye E. The measurement light LS is reflected and scattered at various depth positions of the subject's eye E. Return light of the measurement light LS from the subject's eye E travels along the same route as the outward way in the opposite direction to the fiber coupler 105, and then reaches the fiber coupler 122 through the optical fiber 128.

The fiber coupler 122 superposes the measurement light LS reached here through the optical fiber 128 with the reference light LR reached here through the optical fiber 121 to generate interference light. The fiber coupler 122 splits the interference light generated by the fiber coupler 122 at a predetermined splitting ratio (e.g., 1 to 1) to generate a pair of interference light LC. The pair of interference light LC is guided to the detector 125 through the optical fibers 123 and 124, respectively.

The detector 125 of some examples includes a balanced photo diode. This balanced photodiode includes a pair of photodetectors that detects the pair of the interference light LC respectively. The balanced photodiode outputs a difference signal between a pair of detection signals corresponding to the pair of the interference light LC respectively obtained by the pair of photodetectors. The detector 125 sends this output (this difference signal) to the data acquisition system (DAS) 130.

The clock KC is supplied from the light source unit 101 to the data acquisition system 130. The clock KC is generated in the light source unit 101 in synchronization with the output timings of individual wavelengths varied over a predetermined wavelength range by the wavelength tunable light source. The light source unit 101 of some examples is configured to split the light LO of each output wavelength to generate two pieces of split light, apply an optical delay to one of these two pieces of split light, superpose the resulting two pieces of split light with one another, detect the superposed light, and generate the clock KC based on the detection result of the superposed light. The data acquisition system 130 performs, based on the clock KC, sampling of the detection signal input from the detector 125. The data acquisition system 130 sends the result of this sampling to the arithmetic and control unit 200.

The present configuration example is provided with both an element for changing the sample arm length (e.g., the retroreflector 41) and an element for changing the reference arm length (e.g., the retroreflector 114 or a reference mirror). However, some other embodiments may include only either one of these elements. An element for changing the difference between the sample arm length and the reference arm length (i.e., an element for changing the optical path length difference) is not limited to the elements of the present embodiment, and may be any element such as any optical member or any mechanism.

<Control System and Processing System>

FIG. 3, FIG. 4A, FIG. 4B, FIG. 4C, and FIG. 4D illustrate examples of the configuration of the control system and the processing system of the ophthalmic examination apparatus 1. The arithmetic and control unit 200 of some examples may include the controller 210, the image data constructing unit 220, and the data processor 230. The ophthalmic examination apparatus 1 may include a communication device for performing data communication with external apparatuses and devices. The ophthalmic examination apparatus 1 may include a drive device (reader and/or writer) for reading out data from a recording medium and writing data into a recording medium.

<Controller 210>

The controller 210 performs various kinds of controls. The controller 210 includes the main controller 211 and the memory 212. Further, as shown in FIG. 4A, the main controller 211 of the present embodiment includes the scan controller 2111, and the memory 212 of the present embodiment retains the scan protocol 2121.

<Main controller 211>

The main controller 211 includes one or more processors and controls each unit and each element of the ophthalmic examination apparatus 1 (including the units and elements shown in FIG. 1 to FIG. 4D). The main controller 211 is implemented by cooperation between hardware including the one or more processors and control software. The scan controller 2111 is configured to perform control for OCT scanning applied to a scan area (scan target area) of a predetermined shape and a predetermined size (predetermined dimensions).

The photography focus driver 31A moves the photography focusing lens 31 disposed on the photographing optical path and the focusing optical system 60 disposed on the illumination optical path under control of the main controller 211. The retroreflector driver (RR driver) 41A moves the retroreflector 41 disposed in the sample arm under control of the main controller 211. The OCT focus driver 43A moves the OCT focusing lens 43 disposed in the sample arm under control of the main controller 211. The retroreflector driver (RR driver) 114A moves the retroreflector 114 disposed in the reference arm under control of the main controller 211. Each of the drivers described above includes an actuator such as a pulse motor that operates under control of the main controller 211. The optical scanner 44 operates under control of the main controller 211 (under control of the scan controller 2111).

The movement mechanism 150 of some typical examples is configured to move the fundus camera unit 2 in a three-dimensional manner. The movement mechanism 150 configured in this way includes, for example, the following elements: x stage that can be moved in the ±x directions (i.e., left and right directions); x movement mechanism configured to move the x stage; y stage that can be moved in the ±y directions (i.e., up and down directions); y movement mechanism configured to move the y stage; z stage that can be moved in the ±z directions (i.e., front and back directions, depth direction); and z movement mechanism configured to move the z stage. Each of the x movement mechanism, the y movement mechanism, and the x movement mechanism includes an actuator such as a pulse motor that operates under control of the main controller 211.

<Memory 212>

The memory 212 retains various kinds of data. Examples of data stored in the memory 212 include OCT images, fundus images, subject's eye information, and control information. The subject's eye information includes subject information such as a patient identifier (ID) and a patient's name, identification information for right and left eyes, electronic medical record information, and any information related to subject's eyes. The control information is information related to specific control processes. The control information of the present embodiment includes the scan protocol 2121.

The scan protocol 2121 is a defined set of rules or regulations regarding the contents of control for application of OCT scanning to a scan area of a predetermined shape and a predetermined size. The scan protocol 2121 includes a set of various kinds of control parameters (scan control parameters). The scan protocol 2121 includes protocols for individual scanning modes. The scan protocol 2121 of the present embodiment includes at least a protocol for Lissajous scanning, and may further include protocols for other scanning modes such as a protocol for B-scanning (line scanning), a protocol for cross scanning, a protocol for radial scanning, and a protocol for raster scanning.

The scan control parameters of the present embodiment include at least a parameter representing a content of control for the optical scanner 44. Examples of this parameter include a parameter representing a scanning pattern, a parameter representing a scanning speed, and a parameter representing a scanning interval. The scanning pattern represents the shape of a path or route of scanning, and examples of the scanning pattern include a Lissajous pattern, a line pattern, a cross pattern, a radial pattern, and a raster pattern. The scanning speed is defined, for example, as a repetition rate of A-scans. The scan interval is defined, for example, as an interval (or a distance) between adjacent A-scans, that is, as array intervals (arrangement intervals, disposition intervals) of scan points.

As in the existing or conventional techniques such as those disclosed in Patent documents 1 to 4 and Non-patent documents 1 and 2 mentioned above, "Lissajous scanning" of the present embodiment may not only be Lissajous scanning in a "narrow sense" whose path is a pattern drawn by a locus of points represented and obtained as an ordered pair of two simple harmonic motion perpendicular to each other, but also may be Lissajous scanning in a "broad sense" represented as a predetermined two-dimensional pattern that includes a series of cycles. The pattern of Lissajous scanning in the narrow sense is referred to as a Lissajous pattern, a Lissajous figure, a Lissajous curve, a Lissajous function, or a Bowditch curve.

The optical scanner 44 of the present embodiment may include a first galvanometer mirror and a second galvanometer mirror, for example. The first galvanometer mirror deflects the measurement light LS in the x direction and the second galvanometer mirror deflects the measurement light LS in the y direction. Lissajous scanning can be implemented by simultaneously performing the following two control processes: a process of controlling the first galvanometer mirror to iterate deflection direction change in the x direction with the first period; and a process of controlling the second galvanometer mirror to iterate deflection direction change in the y direction with the second period. The first period and the second period are different from each other.

In some examples, Lissajous scanning of the present embodiment is not limited to scanning of a Lissajous pattern in the narrow sense performed using a combination of two sine waves. Examples of Lissajous scanning of the present embodiment may include scanning of a pattern generated by adding a specific term (e.g., a polynomial of an odd order) to a Lissajous pattern in the narrow sense, and scanning of a pattern based on a triangular wave.

A "cycle" generally means an object composed of a plurality of sampling points and having a certain length. A cycle of the present embodiment may be a closed curve or a nearly closed curve (substantially closed curve, almost closed curve, practically closed curve), for example. In other words, the start and end points of a cycle of the present embodiment may coincide or substantially coincide with each other.

In some typical examples, the scan protocol 2121 is generated based on a Lissajous function. As shown in the equations (9) and (10) of Non-patent document 1, a Lissajous function is expressed, for example, by the following parametric equation system: $x(t_i)=A \cos(2\pi(f_A/n)t_i)$, $y(t_i)=A \cos(2\pi(f_A(n-2)/n^2)t_i)$.

Here, "x" denotes the horizontal axis of the two-dimensional coordinate system in which the Lissajous curve is defined, and "y" denotes the vertical axis. Further, "$t_i$" denotes the acquisition time point of the i-th A-line in the Lissajous scanning, "A" denotes the scan area (amplitude), "$f_A$" denotes the acquisition rate of the A-lines (A-scan speed, A-scan repetition rate), and "n" denotes the number of A-lines in each cycle in the x direction (the horizontal axis direction).

Figure 5:
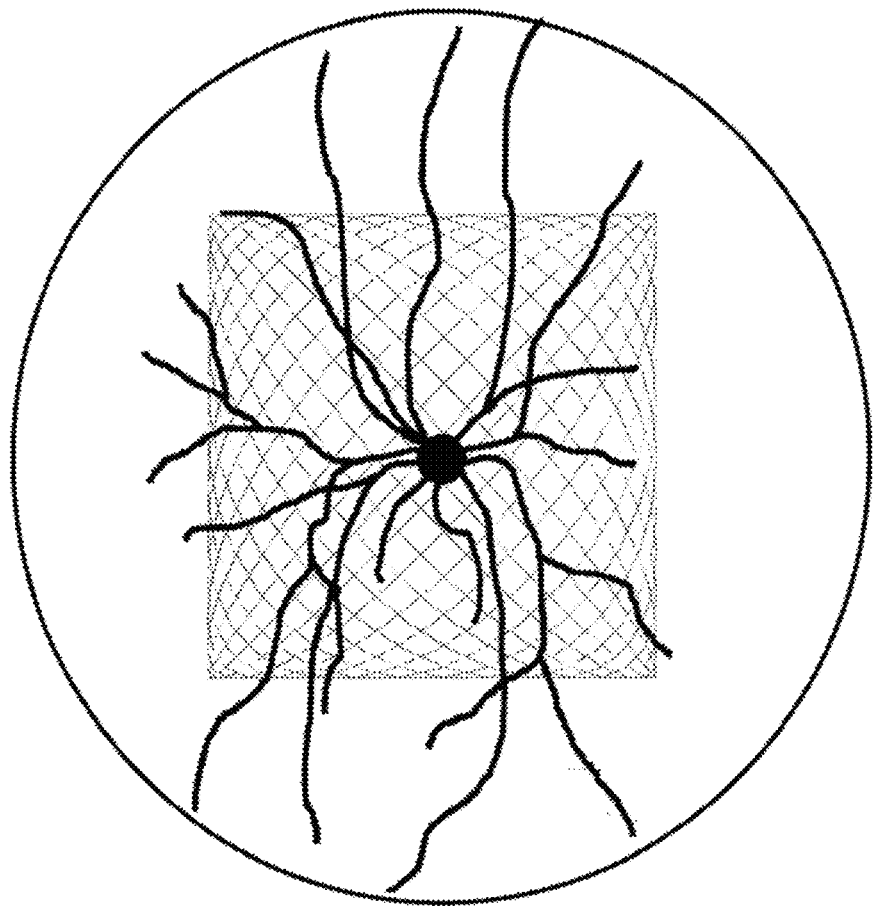
FIG. 5 illustrates an example of the pattern of a Lissajous scan performed by an ophthalmic examination apparatus according to the present disclosure.

FIG. 5 shows an example of a distribution of scan lines of the above example of Lissajous scanning, in other words, an example of a scan pattern of the above example of Lissajous scanning.

Any cycle pair (a pair of cycles) included in Lissajous scanning (of the narrow sense or the broad sense) crosses (intersects) each other at one or more points (particularly at two or more points). The intersections of cycles make it possible to carry out registration between a pair of data acquired from any pair of cycles in the Lissajous scanning, which makes it possible to implement the image construction technique and the motion artifact correction technique disclosed in Non-patent document 1 or 2. Unless otherwise mentioned, described in the following are cases in which the technique of Non-patent document 1 is applied.

The control information stored in the memory 212 is not limited to the above examples. For example, the control information may include information for performing focus control. This information is referred to as a focus control parameter.

The focus control parameter represents a content of control applied to the OCT focus driver 43A. Examples of the focus control parameter include a parameter representing a focal position of the sample arm, a parameter representing a movement speed of a focal position of the sample arm, and a parameter representing a movement acceleration of a focal position of the sample arm. The parameter representing the focal position of some examples may be a parameter that represents a position of the OCT focusing lens 43. The parameter representing the movement speed of the focal position of some examples may be a parameter that represents a movement speed of the OCT focusing lens 43. The parameter representing the movement acceleration of the focal position of some examples may be a parameter that represents a movement acceleration of the OCT focusing lens 43. The movement speed may or may not be constant. The movement acceleration may or may not be constant.

Using any of the focus control parameters, it becomes possible to carry out focus adjustment in accordance with the conditions or states of the fundus Ef such as the shape and the aberration distribution of the fundus Ef. The shape of the fundus Ef of some typical examples is a concave shape with a deep central part and a shallow peripheral part. The focus control of the present example may be executed in an interlocking manner with the scan control, that is, iteration control (repetition control) of Lissajous scanning. This interlocking control makes it possible to provide a high quality image with motion artifacts corrected and in focus over the entire scan area.

<Scan Controller 2111>

The scan controller 2111 controls at least the optical scanner 44 based on the scan protocol 2121. The scan controller 2111 may further perform control of the light source unit 101 in an interlocking manner with the control of the optical scanner 44 based on the scan protocol 2121. The scan controller 2111 is implemented by cooperation between hardware including one or more processors and scan control software including the scan protocol 2121.

<Image Data Constructing Unit 220>

The image data constructing unit 220 includes one or more processors and constructs OCT image data of the fundus Ef based on a signal (sampling data) input from the data acquisition system 130. This OCT image data construction process includes noise elimination (noise reduction), filtering, fast Fourier transform (FFT), and other processes, as in existing or conventional Fourier domain OCT techniques (existing or conventional swept source OCT techniques). In the cases of employing any other types of OCT techniques, the image data constructing unit 220 executes, for constructing OCT image data, known processes in accordance with the OCT technique employed.

The image data constructing unit 220 of some examples is configured to perform at least the process of constructing a set of image data corresponding to individual scan points (individual A-lines) from the sampling data. Image data corresponding to each scan point (each A-line) is referred to as A-scan image data. In some examples, image data constructed by the image data constructing unit 220 may be data prior to the image construction process (pre-imaged data). Examples of the pre-imaged data include a signal profile along the depth direction (z direction, optical axis direction, axial direction, A-line direction) such as a reflection profile or a scattering profile.

As described above, the present embodiment applies Lissajous scanning to the fundus Ef. By collaborating with the data processor 230, the image data constructing unit 220 constructs three-dimensional image data of the fundus Ef, for example, by applying the image construction technique and the motion artifact correction technique described in Non-patent document 1 or 2, to a data set obtained through the data acquisition performed using Lissajous scanning and the sampling performed by the data acquisition system 130.

The image data constructing unit 220 and/or the data processor 230 may be configured to construct an image to be displayed, by applying a rendering process to three-dimensional image data. Examples of applicable rendering techniques include volume rendering, surface rendering, maximum intensity projection (MIP), minimum intensity projection (MinIP), and multi planar reconstruction (MPR).

The image data constructing unit 220 and/or the data processor 230 may construct an OCT front image (en face OCT image) based on three-dimensional image data. For example, the image data constructing unit 220 and/or the data processor 230 may construct projection data of three-dimensional image data by projecting the three-dimensional image data in the z direction (A-line direction, optical axis direction, axial direction, depth direction). The image data constructing unit 220 and/or the data processor 230 may construct a shadowgram of three-dimensional image data by projecting partial three-dimensional image data, which is part of the three-dimensional image data, in the z direction. This partial three-dimensional image data may be obtained, for example, by using any segmentation techniques. Segmentation is a process of identifying a partial region of an image. The present example may be configured to perform segmentation to identify an image region corresponding to one or more tissues or sites of the fundus Ef.

Not limited to the shadowgram construction process, segmentation of some embodiments may employ any known techniques such as thresholding, edge detection, filtering, or machine learning (e.g., semantic segmentation).

The ophthalmic examination apparatus 1 may be capable of performing OCT angiography. OCT angiography is an imaging technique of constructing an image in which blood vessels are emphasized (see, for example, Non-patent document 2, and Japanese Unexamined Patent Application Publication (Translation of PCT Application) No. 2015-515894). Generally, tissues of eye fundus (structure of eye fundus) do not change within a short period of time while blood flows inside blood vessels change within a short period of time. OCT angiography emphasizes, as blood flow signals, parts where such temporal changes exist, thereby generating an image. OCT angiography is also referred to as OCT motion contrast imaging. Images acquired by OCT angiography are referred to as blood vessel enhanced images, angiographic images, angiograms, motion contrast images, or the like.

In the case where OCT angiography can be performed, the ophthalmic examination apparatus 1 repeats scanning of the same region of the fundus Ef a predetermined number of times. For example, the ophthalmic examination apparatus 1 repetitively performs the above-described scan control (repetitive control of Lissajous scanning) a predetermined number of times. This scan control allows the data acquisition system 130 to acquire a plurality of pieces of three-dimensional data (time-series three-dimensional data set) from the region to which the Lissajous scanning is applied. The image data constructing unit 220 and/or the data processor 230 may construct a motion contrast image from this three-dimensional data set. This motion contrast image is an angiographic image in which the temporal changes in interference signals caused by blood flows in the fundus Ef are emphasized. This angiographic image is three-dimensional angiographic image data that represents a three-dimensional distribution of blood vessels in the fundus Ef.

The image data constructing unit 220 and/or the data processor 230 may be configured to construct two-dimensional angiographic image data and/or pseudo three-dimensional angiographic image data from the three-dimensional angiographic image data. In some examples, the image data constructing unit 220 and/or the data processor 230 may be configured to apply multi planar reconstruction to the three-dimensional angiographic image data to construct two-dimensional angiographic image data representing a freely selected cross section of the fundus Ef. In some examples, the image data constructing unit 220 and/or the data processor 230 may be configured to construct en face angiographic image data of the fundus Ef by applying the above-described projection image construction or the above-described shadowgram construction to the three-dimensional angiographic image data.

In the present embodiment, the image data constructing unit 220 and/or the data processor 230 construct a plurality of strips from data collected by the data acquisition system 130. As described in Non-patent document 1, the image data constructing unit 220 and/or the data processor 230 partitions a volume (three-dimensional data) collected by Lissajous scanning into a plurality of sub-volumes in each of which relatively large motion is not involved, and constructs en face projections for individual sub-volumes. Each of these en face projections is a strip. By applying a registration process and a merging process to the plurality of strips created in this way, an image with motion artifacts corrected can be obtained. As described below, the present example performs the registration process and the merging process by the data processor 230.

The image data constructing unit 220 is implemented by cooperation between hardware including one or more processors and image constructing software. In some aspect examples, the image data constructing unit 220 and the data processor 230 may be configured as an integrated unit.

<Data Processor 230>

The data processor 230 includes one or more processors and perform various kinds of data processing on an image of the subject's eye E. The data processor 230 of some examples is implemented by cooperation between hardware including the processor(s) and data processing software.

The data processor 230 may be configured to perform position matching (registration) between two images acquired for the fundus Ef. The data processor 230 of some examples may be configured to perform registration between three-dimensional image data acquired using an OCT technique and an en face image acquired by the fundus camera unit 2. The data processor 230 of some examples may be configured to perform registration between two OCT images acquired using an OCT technique(s). The data processor 230 of some examples may be configured to perform registration between two en face images acquired by the fundus camera unit 2. The data processor 230 of some examples may be configured to apply registration to resulting data of analysis performed on an OCT image(s), resulting data of analysis performed on an en face image(s), and/or other analysis results. These registration processes can be performed using freely selected known techniques such as feature point extraction, affine transformation, and/or other image processing techniques.

Further, the data processor 230 is configured to process a data set obtained using Lissajous scanning. As described above, the image data constructing unit 220 of some examples is configured to construct a plurality of strips from data collected by Lissajous scanning. In this case, the data processor 230 of some examples is configured to apply registration and merging process to these strips to construct an image in which motion artifacts are corrected.

As a property of Lissajous scanning, any two strips have their overlapping area. As in the technique described in Non-patent document 1, the data processor 230 is configured to perform registration between strips using the overlapping area between these strips. First, the data processor 230 performs ordering (sequencing, arrangement) of the plurality of strips constructed by the image data constructing unit 220 based on the sizes (e.g., areas) of these strips (thereby, the first to N-th strips are defined), and designates the first strip with the largest size as the initial reference strip. Next, the data processor 230 performs registration between the first strip and the second strip using the first strip as a reference, and merges (synthesizes, combines) the first strip and the second strip together. Then, the data processor 230 performs registration between the resulting merged strip (the strip created by the merging of the first strip and the second strip) and the third strip using this merged strip as a reference, and merges this merged strip and the third strip together. The data processor 230 repeats such registration and such a merging process sequentially in the above-described order to perform position matching and merging of the first to N-th strips, thereby creating an image with motion artifacts corrected.

The registration of the present example uses cross-correlation functions to calculate the relative position between a reference strip and another strip. Since strips have various shapes, the present example performs correlation calculations between strips using masks (mask images) that convert the strips to images of the same outer shape (e.g., square shape), as in Appendix A of Non-patent document 1.

As mentioned above, since strips are intensity images of a predetermined gradations (shades, tones) and mask images are binary images, the differences between the absolute values of the pixel values of the strips and the absolute values of the pixel values of the masks may become large. As a result, the effect of the masks in the correlation calculations using the strips and the masks may be ignored, and accurate correlation coefficients may not be obtained. In particular, when a single-precision floating-point format calculation (float type calculation) is used to calculate correlation coefficients between strips from the viewpoint of cost, etc., this problem becomes more serious and severe due to the effect of rounding errors (round-off errors) caused by the small number of effective digits (significant digits).

Figure 4B:
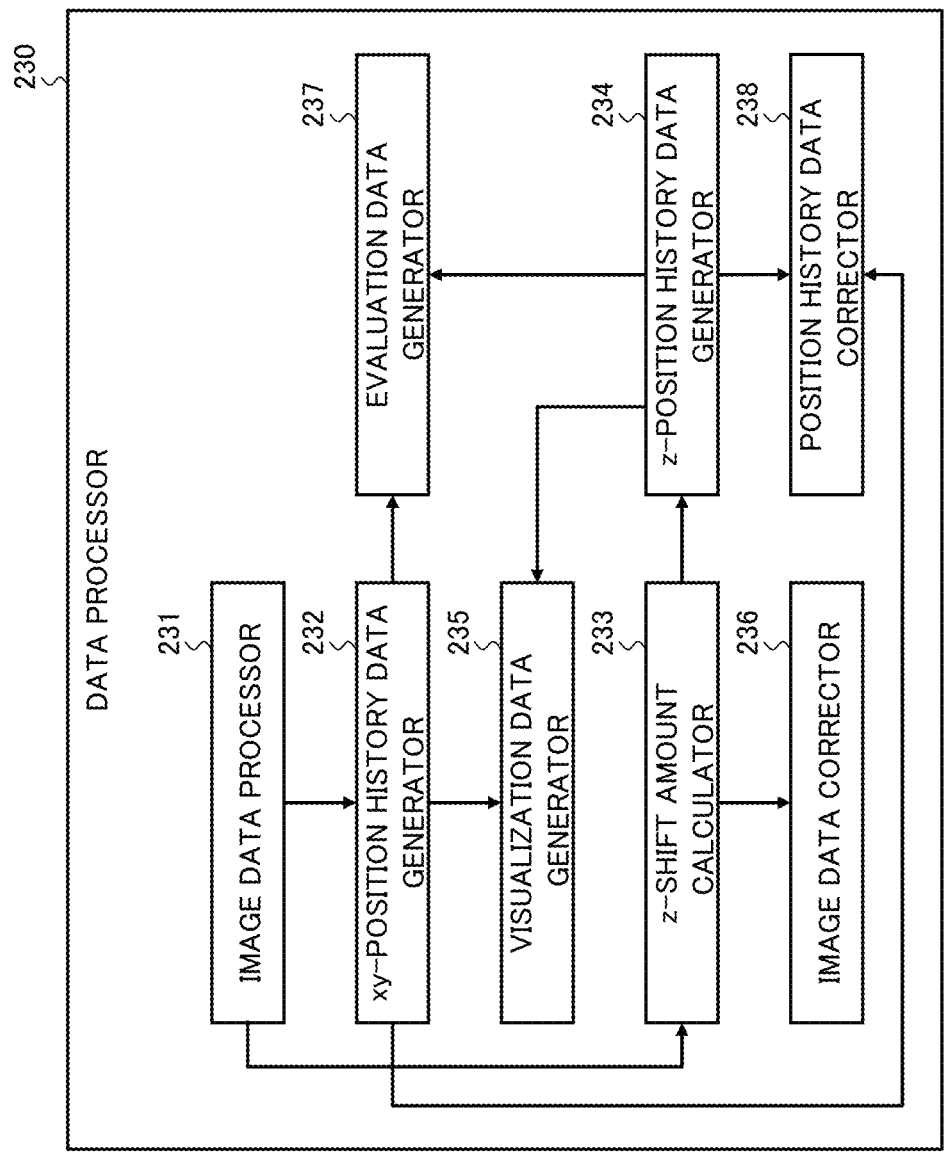
FIG. 4B illustrates an example of the configuration of an ophthalmic examination apparatus according to the present disclosure.
Figure 4C:
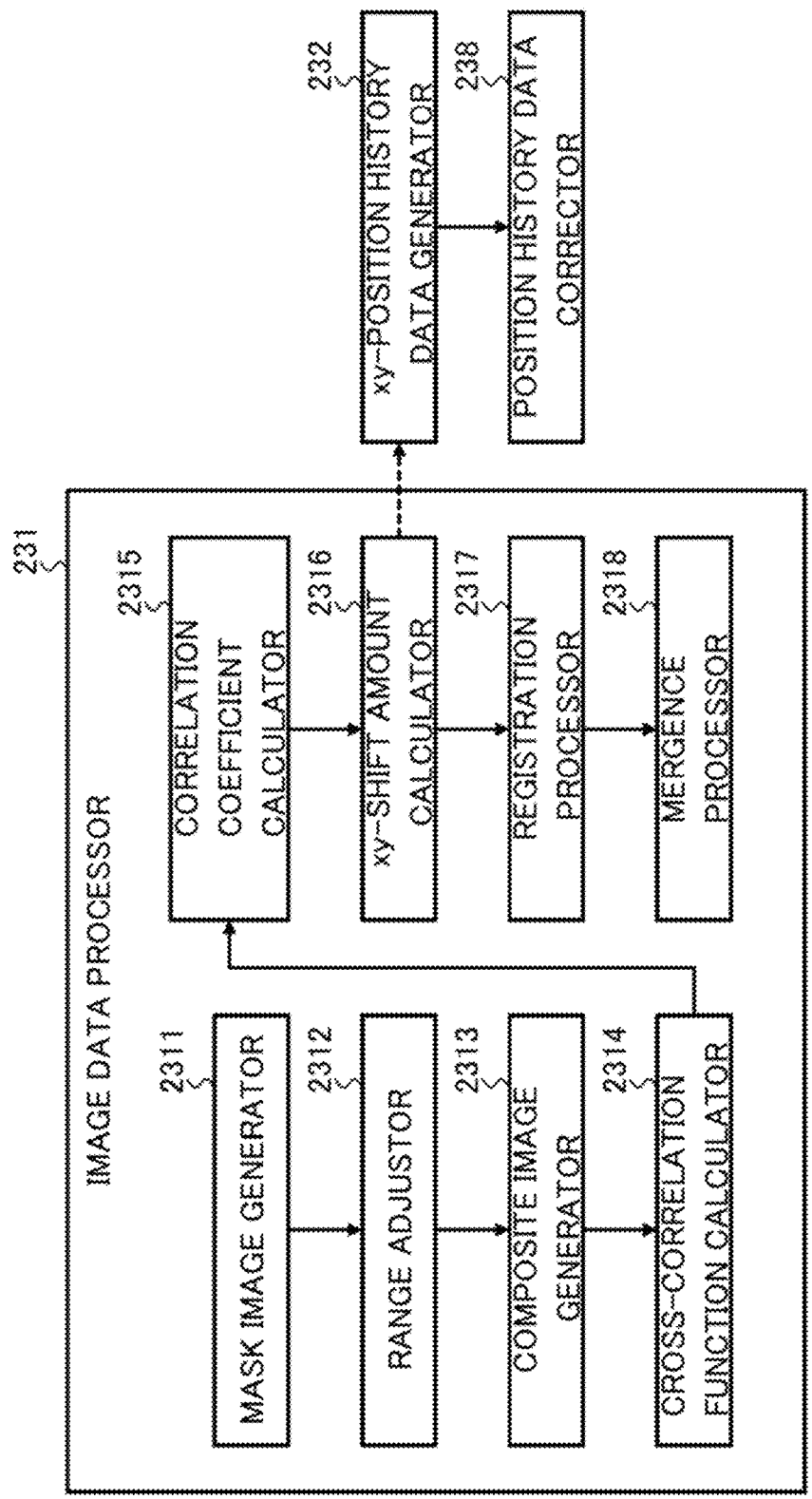
FIG. 4C illustrates an example of the configuration of an ophthalmic examination apparatus according to the present disclosure.
Figure 4D:
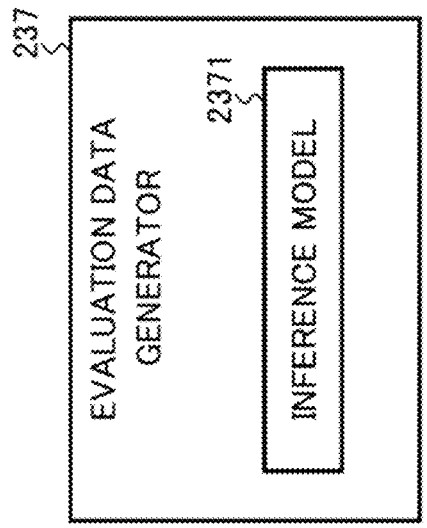
FIG. 4D illustrates an example of the configuration of an ophthalmic examination apparatus according to the present disclosure.

In the present embodiment, the data processor 230 with the configurations shown in FIG. 4B to FIG. 4D is employed to address the rounding error problem and also to perform detection and evaluation of motions of the subject's eye E.

As shown in FIG. 4B, the data processor 230 of the present example includes the image data processor 231, the xy-position history data generator 232, the z-shift amount calculator 233, the z-position history data generator 234, the visualization data generator 235, the image data corrector 236, the evaluation data generator 237, and the position history data corrector 238.

<Image Data Processor 231>

The image data processor 231 is configured to process image data constructed by the image data constructing unit 220. As shown in FIG. 4C, the image data processor 231 includes the mask image generator 2311, the range adjustor 2312, the composite image generator 2313, the cross-correlation function calculator 2314, the correlation coefficient calculator 2315, the xy-shift amount calculator 2316, the registration processor 2317, and the mergence processor 2318. The example described below performs a process of selecting any two strips, a process of designating one of the selected two strips as a reference strip, and a process of performing registration of the other strip (referred to as a registering strip) against this reference strip.

<Mask Image Generator 2311>

The mask image generator 2311 is configured to generate a reference mask image for the reference strip and a registering mask image for the registering strip. Some examples of mask images will be described below; however, mask images according to embodiments are not limited to these examples.

In some examples, the outer shape (contour shape) of a mask image may be a rectangular shape, and may typically be a square shape. The shape of a reference mask image and the shape of a registering mask image may be the same. The dimensions of a reference mask image and the dimensions of a registering mask image may be the same.

In some examples, the range of pixel values of mask images may be set to be included in the closed interval [0, 1]. Mask images of some typical examples may be binary images with pixel values of "0" or "1". As a concrete example, the mask image is a binary image in which the values of pixels in a region corresponding to a domain (defined area) of a strip are "1" and the values of other pixels are "0". In other words, as shown in the expression (20) of Non-patent document 1, the pixel values of an example mask image have values of "1" within the image area of a corresponding strip and values of "0" for other areas.

<Range Adjustor 2312>

The range adjustor 2312 is configured to perform, based on a pixel value range of a reference mask image and a pixel value range of a registering mask image, adjustment between a pixel value range of a reference strip and a pixel value range of a registering strip. The range adjustor 2312 of some typical examples is configured to perform adjustment between a pixel value range of a reference strip and a pixel value range of a registering strip in such a manner as to reduce the difference between a pixel value range of a strip and a pixel value range of a mask image.

More generally, the range adjustor 2312 performs relative adjustment between a pixel value range of a reference strip, a pixel value range of a registering strip, and pixel value ranges of mask images. In some typical examples, a reference mask image applied to a reference strip and a registering mask image applied to a registering strip are different from one another, and the range adjustor 2312 performs relative adjustment between a pixel value range of this reference strip, a pixel value range of this registering strip, a pixel value range of this reference mask image, and a pixel value range of this registering strip.

The range adjuster 2312 may be configured to perform the following two adjustment processes: relative adjustment between a pixel value range of a reference strip and a pixel value range of a reference mask image in such a manner as to reduce the difference between the pixel value range of the reference strip and the pixel value range of the reference mask image; and relative adjustment between a pixel value range of a registering strip and a pixel value range of a registering mask image in such a manner as to reduce the difference between the pixel value range of the registering strip and the pixel value range of the registering mask image.

The range adjuster 2312 may be configured to perform adjustment between a pixel value range of a strip and a pixel value range of a mask image in such a manner as to equalize (match) the pixel value range of one of the strip and the mask image with the pixel value range of the other. In some examples, the range adjuster 2312 may be configured to perform the following two adjustment processes: relative adjustment between a pixel value range of a reference strip and a pixel value range of a reference mask image in such a manner as to equalize the pixel value range of the reference strip and the pixel value range of the reference mask image with one another; and relative adjustment between a pixel value range of a registering strip and a pixel value range of a registering mask image in such a manner as to equalize the pixel value range of the registering strip and the pixel value range of the registering mask image with one another.

In some examples, the range adjustor 2312 may be configured to perform normalization of a pixel value range of a strip based on a pixel value range of a mask image. Some examples of this normalization process will be described below; however, normalization techniques are not limited to these examples.

The first example of the normalization will be described. In the case where a pixel value range of a mask image is contained in the closed interval [0, 1], the range adjustor 2312 of the present example divides the values of individual pixels of a strip by the maximum value of the pixel values of this strip. In order to do this, the range adjustor 2312 of the present example first compares the values of all pixels of a strip to identify the maximum value (maximum pixel value), and then divides the value of each of the pixels of the strip by the maximum pixel value identified. As a result, the pixel value range of the strip becomes the closed interval [0, 1], which is the same as the pixel value range of the mask image.

The second example of the normalization will be described. In the case where a pixel value range of a mask image is contained in the closed interval [0, 1], the range adjustor 2312 of the present example divides the values of individual pixels of a strip by the maximum value of the pixel value range of this strip. The pixel value range of a strip is set in advance, and the range adjustor 2312 of the present example divides the values of individual pixels of the strip by the upper limit value (upper bound value) of the pixel value range of the strip. According to the present example, the pixel value range of a strip is matched to the same closed interval [0, 1] as the pixel value range of a mask image.

The process performed by the range adjustor 2312 can reduce the difference between the absolute value of a pixel value of a strip and the absolute value of a pixel value of a mask. As a result, the effect of masks in the correlation calculations using strips and masks may not be ignored. This makes it possible to accurately perform correlation coefficient calculation. In particular, the effect of rounding errors (round-off errors) caused by the small number of effective digits (significant digits) can be eliminated (cancelled) or reduced when a single-precision floating-point format calculation (float type calculation) is used in correlation coefficient calculation.

The present disclosure mainly describes an example where only a pixel value range of a strip is changed. However, some examples may change only a pixel value range of a mask image, and some other examples may change both a pixel value range of a strip and a pixel value range of a mask image.

<Composite Image Generator 2313>

For strips and mask images to which the pixel value range adjustment process is applied by the range adjustor 2312, the composite image generator 2313 generates a composite image by combining a mask image with a reference strip, and generates another composite image by combining a mask image with a registering strip. In some typical examples, the composite image generator 2313 synthesizes a reference strip and a reference mask image to generate a reference composite image, and synthesizes a registering strip and a registering mask image to generate a registering composite image.

The process of synthesizing a strip and a mask image may be performed in the same manner as in Non-patent document 1. However, unlike the technique of Non-patent document 1, the present embodiment performs pixel value range adjustment in such a manner as to reduce the difference between a pixel value range of a strip and a pixel value range of a mask image. In some typical examples, a pixel value range of a reference strip and a pixel value range of a registering strip are normalized in such a manner that pixel value ranges of the reference strip and the registering strip are matched with pixel value ranges of a reference mask image and a registering mask image.

For example, in the same manner as expression (19) in Non-patent document 1, the composite image generator 2313 may be configured to embed a strip with its pixel value range normalized into an image of the same dimensions and the same shape as a mask image.

Then, the composite image generator 2313 may generate a composite image of the mask image and the image into which the strip is embedded. This composite image corresponds to "f'(r)m$_f$(r)" in Non-patent document 1 (see the second line of page 1800, etc. of Non-patent document 1). However, as mentioned above, the values of the strip embedded image are different from those of expression (19) in Non-patent document 1.

<Cross-Correlation Function Calculator 2314>

The cross-correlation function calculator 2314 calculates a plurality of cross-correlation functions based on two composite images generated by the composite image generator 2313. The cross-correlation function calculation is performed in the same way as in Non-patent document 1. For example, the cross-correlation function calculator 2314 calculates the six cross-correlation functions (image cross-correlation) in the equation (33) of Non-patent document 1, based on a reference composite image generated from a reference strip and a reference mask image as well as a registering composite image generated from a registering strip and a registering mask image.

<Correlation Coefficient Calculator 2315>

The correlation coefficient calculator 2315 calculates the correlation coefficient based on the plurality of cross-correlation functions calculated by the cross-correlation function calculator 2314. This calculation follows the equation (33) in Non-patent document 1.

<Xy-Shift Amount Calculator 2316>

The xy-shift amount calculator 2316 calculates the amount of a shift (amount of a positional difference) in the xy direction (lateral direction) between a reference strip and a registering strip, based on the correlation coefficients calculated by the correlation coefficient calculator 2315.

In some examples, the calculation for determining an xy-shift amount (xy-directional shift amount) includes calculation corresponding to "rough lateral motion correction" described in Non-patent document 1 (see page 1787), and the xy-shift amount calculator 2316 is configured to estimate an xy-shift amount by finding the maximum value of the cross-correlation function.

Further, the xy-shift amount calculator 2316 may be configured to execute calculation corresponding to "fine lateral motion correction" described in Non-patent document 1 (see page 1789) for determining a small shift amount in the lateral direction caused by eye movements such as slow drift or tremor.

<Registration Processor 2317>

The registration processor 2317 performs registration in the lateral direction based on the shift amount in the lateral direction calculated by the xy-shift amount calculator 2316. In some examples, this lateral registration includes the process corresponding to "rough lateral motion correction" described in Non-patent document 1 (see page 1787). The registration processor 2317 may perform registration between a reference strip and a registering strip in such a manner as to eliminate (cancel) or reduce the shift amount in the lateral direction calculated by the xy-shift amount calculator 2316.

In the case where the xy-shift amount calculator 2316 performs calculation corresponding to "fine lateral motion correction" of Non-patent document 1 (see page 1789), the registration processor 2317 may perform registration corresponding to "fine lateral motion correction" of Non-patent document 1 (see page 1789) to reject (remove, reduce) a small motion artifact in the lateral direction between a reference strip and a registering strip.

Data of the lateral shift amount calculated by the xy-shift amount calculator 2316 is sent to the xy-position history data generator 232.

<Mergence Processor 2318>

The mergence processor 2318 constructs a merged image of a reference strip and a registering strip whose relative position has been adjusted by the registration processor 2317. This process is performed in the same manner as the technique described in Non-patent document 1.

As mentioned above, the image data processor 231 sequentially performs the above-described series of processes in the order determined based on the sizes of the plurality of strips constructed by the image data constructing unit 220. This generates, from the plurality of strips constructed by the image data constructing unit 220, a merged image with lateral motion artifacts corrected. In some typical examples, this merged image is an image of the entire area to which Lissajous scanning has been applied.

As described above, the plurality of strips is a plurality of en face projection images created from a plurality of sub-volumes obtained by partitioning a volume (three-dimensional data) collected by Lissajous scanning. Therefore, a merged image constructed from the plurality of strips by the image data processor 231 gives a plurality of sub-volumes whose lateral positions have been adjusted (and a merged image of the plurality of sub-volumes). In the present example, registration and a merging process in the depth direction perpendicular to the lateral direction are executed by the z-shift amount calculator 233 and the image data corrector 236 (described later).

<Xy-Position History Data Generator 232>

While the above-described series of processes is being executed in accordance with the order determined based on the sizes of the plurality of strips constructed by the image data constructing unit 220, the xy-shift amount calculator 2316 performs sequential calculations of lateral shift amounts between individual pairs of strips (a plurality of pairs of a reference strip and a registering strip) that have been sequentially defined. The xy-position history data generator 232 collects a plurality of pieces of shift amount data sequentially calculated by the xy-shift amount calculator 2316. With this, the xy-position history data generator 232 acquires a set of lateral shift amounts between the plurality of strips.

The xy-position history data generator 232 sequences the collected shift amounts in the acquired set, based on a scan order corresponding to the plurality of strips. In other words, the xy-position history data generator 232 sequences the collected shift amounts in the acquired set in the time series order (chronological order, time course, time axis, scan order). This generates an ordered set from the acquired set of shift amounts. As a result, data representing lateral movements of the subject's eye E during Lissajous scanning is obtained. That is, data representing a history (record) of lateral positions of the subject's eye E is obtained. This data is referred to as xy-position history data in the present disclosure.

The "time" in the present example is not limited to that expressed in parameters or units related to time (e.g., microseconds), but may be expressed in any parameters or units that are equivalent (mutually convertible) to parameters or units related to time. For example, the order of Lissajous scanning (the scan order corresponding to individual cycles) is equivalent to parameters or units related to time if scan intervals are known such as the cases in which scan intervals are fixed or constant.

<Z-Shift Amount Calculator 233>

The z-shift amount calculator 233 calculates a shift amount in the z direction (A-line direction, optical axis direction, depth direction) between a plurality of sub-volumes obtained by partitioning a volume collected by Lissajous scanning. That is, the z-shift amount calculator 233 calculates a shift amount in the z direction between a plurality of sub-volumes from which a plurality of strips is constructed.

The present example is configured to perform position adjustment in the z direction by the z-shift amount calculator 233 and the image data corrector 236 after the image data processor 231 performs position adjustment in the xy direction (lateral direction). In other words, the z-shift amount calculator 233 of the present example is configured to calculate a shift amount in the z direction using data acquired by the image data processor 231 such as xy-shift amount data or a merged image.

Some examples of processes executed by the z-shift amount calculator 233 will be described. Like a pair of strips (a pair of a reference strip and a registering strip) processed in the above-described xy-shift amount calculation, a pair of sub-volumes is processed in z-shift amount calculation. A sub-volume pair may consist of two sub-volumes corresponding to a reference strip and a registering strip considered in the xy-shift amount calculation. A sub-volume corresponding to a reference strip is referred to as a reference sub-volume, and a sub-volume corresponding to a registering strip is referred to as a registering sub-volume.

Based on a result of registration in the xy direction between corresponding reference strip and registering strip, the positions in the xy direction of a reference sub-volume and a registering sub-volume are adjusted. As mentioned above, any two strips of Lissajous scanning overlap (intersect) at four places, and therefore any two sub-volumes also overlap (intersect) at four places.

The z-shift amount calculator 233 first identifies an overlapping area (common area) between a reference sub-volume and a registering sub-volume whose xy positions have been adjusted. Each overlapping area is three-dimensional image data.

Next, the z-shift amount calculator 233 sets a cross section in the identified overlapping area. This cross section is, for example, a plane spanned (defined) by the z axis and any axis in the xy plane. This axis in the xy plane may be any of the x axis, the y axis, and an axis oblique to both the x axis and the y axis. A cross section set by the z-shift amount calculator 233 is not limited to a plane. A cross section set by the z-shift amount calculator 233 may be of any shape such as a curved surface.

Next, the z-shift amount calculator 233 constructs an image of the cross section set in the above way from the reference sub-volume, and constructs another image of the same cross section from the registering sub-volume. The cross sectional image constructed from the reference sub-volume is referred to as a reference cross sectional image, and the cross sectional image constructed from the registering sub-volume is referred to as a registering cross sectional image. The reference cross sectional image and the registering cross sectional image represent the same cross section in the overlapping area of the reference sub-volume and the registering sub-volume. Here, registration in the xy direction has already been applied to the reference sub-volume and the registering sub-volume.

Next, the z-shift amount calculator 233 analyzes the reference cross sectional image to identify an image of a predetermined site of the subject's eye E, and analyzes the registering cross sectional image to identify an image of the same site. This site of the subject's eye E may be any site of an eye. For example, this site of the subject's eye E may be the surface of the fundus Ef (e.g., retinal surface, internal limiting membrane, the boundary between retina and vitreous body). If an artificial object has been implanted in the subject's eye E, an image of this artificial object may be identified by the z-shift amount calculator 233. In some examples, the analysis of identifying an image of a predetermined site of the subject's eye E may include segmentation.

Next, the z-shift amount calculator 233 calculates a z coordinate of the image of the predetermined site (referred to as a reference image) identified from the reference cross sectional image, and calculates a z coordinate of the image of the predetermined site (referred to as a registering image) identified from the registering cross sectional image. In some typical examples, each of these images of the predetermined site consists of a plurality of pixels (picture elements), and the z coordinates of these pixels are not the same. For example, the global shape of the retinal surface is generally of a curved shape convex toward the +z direction, and images of any local areas (e.g., reference image and registering image) are generally at least partially angled against the z axis. The z-shift amount calculator 233 may be configured to calculate a z coordinate of an image of a predetermined site based on at least one pixel of the group of pixels of this image. For example, the z-shift amount calculator 233 may calculate a statistic of z coordinates from this group of pixels and use this statistic as a z coordinate of this image. This statistic may be any representative value (summary statistic, descriptive statistics value) such as maximum value, minimum value, mean value, median value, mode, or quantile. In the case where an image of a predetermined site consists of a single pixel, the z coordinate of this pixel can be used as the z coordinate of this predetermined site.

Next, the z-shift amount calculator 233 calculates the difference between the z coordinate of the reference image and the z coordinate of the registering image, that is, calculates the shift amount in the z direction. Some aspect examples may be configured to execute processing control to perform the correction process by the image data corrector 236 when the z-shift amount exceeds a threshold value. This threshold value may be, for example, zero or a positive value, and may be a predetermined fixed value or a variable value.

In the above example, a z-shift amount is obtained by constructing a two-dimensional image data (cross sectional image) from three-dimensional image data (sub-volume). In some cases, however, a z-shift amount may be obtained from three-dimensional image data without two-dimensional image data construction. In this case, the same process that is applied to a pair of a reference cross sectional image and a registering cross sectional image, may be performed on a pair of a reference sub-volume and a registering sub-volume.

In the above example, a z-shift amount is obtained by constructing a two-dimensional image data (cross sectional image) from three-dimensional image data (sub-volume) and by identifying an image of a predetermined site from this two-dimensional image data. In some cases, however, a z-shift amount may be obtained by identifying an image of a predetermined site from three-dimensional image data and by constructing two-dimensional image data of this identified image of the predetermined site.

The z-shift amount calculator 233 may be configured to calculate a z-shift amount between a reference sub-volume and a registering sub-volume based on correlation coefficients calculated on the basis of the pair of the reference sub-volume and the registering sub-volume, such as based on the correlation coefficients calculated by the correlation coefficient calculator 2315. Techniques of the z-shift amount calculation are not limited to the technique described above as an example. Techniques of the z-shift amount calculation may be any techniques applicable to a pair of a reference sub-volume and a registering sub-volume, or any techniques applicable to a pair of any other objects.

<Z-Position History Data Generator 234>

As described above, the z-shift amount calculator 233 sequentially calculates the z-shift amounts between pairs of sub-volumes (e.g., a plurality of pairs of a reference sub-volume and a registering sub-volume) that are sequentially formed from a plurality of sub-volumes obtained by dividing a volume collected by Lissajous scanning. The z-position history data generator 234 then collects a plurality of pieces of shift amount data sequentially calculated by the z-shift amount calculator 233. In this way, the z-position history data generator 234 acquires a set of z-shift amounts between the plurality of sub-volumes obtained by partitioning the volume collected by Lissajous scanning.

The z-position history data generator 234 sequences z-shift amounts in the formed set of the z-shift amounts in accordance with the scan order corresponding to the plurality of sub-volumes. In other words, the z-position history data generator 234 sequences the collected z-shift amounts in the formed set in the time series order (chronological order, time course, time axis, scan order). This generates an ordered set of the collected z-shift amounts. As a result, data representing movements in the z direction of the subject's eye E during Lissajous scanning is obtained. That is, data representing a history (record) of z-positions (positions in the z direction) of the subject's eye E is obtained. This data is referred to as z-position history data in the present disclosure.

The present aspect example is configured to combine the xy-position history data acquired by the xy-position history data generator 232 and the z-position history data acquired by the z-position history data generator 234. With this, the present aspect example obtains data representing three-dimensional movements of the subject's eye E during Lissajous scanning, that is, data representing a history (record) of three-dimensional positions (positions in the xyz directions) of the subject's eye E.

The position history data generated by the xy-position history data generator 232 and the z-position history data generator 234 is data in which time information and position information are associated with each other. As can be seen from the method of generating the position history data described above, the position information in the position history data may include a displacement represented based on a certain time point. The reference time point for the representation of the position information may be, for example, the initial time point of the period during Lissajous scanning has been executed.

In some aspect examples, an ordinal numbers (ordinal numerals, order, sequence) m=1, 2, ..., M (here, "M" is an integer equal to or greater than 2) in accordance with a scan order (i.e., chronological order) may be assigned to a plurality of sub-volumes (or, a plurality of strips based on these sub-volumes) obtained by dividing a volume acquired by Lissajous scanning. Then, the positional history data can be represented as the set $\{(\Delta x_m, \Delta y_m, \Delta z_m, t_m): m=1, 2, ..., M\}$.

Here, $t_m$ represents time (time point), $\Delta x_m$ represents the displacement in the x direction of the subject's eye E at the time point $t_m$, $\Delta y_m$ represents the displacement in the y direction of the subject's eye E at the time point $t_m$, and $\Delta z_m$ represents the displacement in the z direction of the subject's eye E at the time point $t_m$. For example, $\Delta x_1$, $\Delta y_1$ and $\Delta z_1$ are all zero, $\Delta x_m$ (m=2 to M) is the displacement in the x direction of the subject's eye E occurred during the period of time from the time point $t_{m-1}$ to the time point $t_m$, $\Delta y_m$ (m=2 to M) is the displacement in the y direction of the subject's eye E occurred during the period of time from the time point $t_{m-1}$ to the time point $t_m$, and $\Delta z_m$ (m=2 to M) is the displacement in the z direction of the subject's eye E occurred during the period of time from the time point $t_{m-1}$ to the time point $t_m$.

In some other aspect examples, the position history data may be data in which time information and three-dimensional coordinates are associated with each other, which is formed by applying a recursive process to the position history data example $\{(\Delta x_m, \Delta y_m, \Delta z_m, t_m): m=1, 2, ..., M\}$ described above. In this position history data, the x coordinate $x_m$ at the time point $t_m$ may be defined by $x_m = \Delta x_1 + ... + \Delta x_m$ (m=1 to M). In the same manner, the y coordinate $y_m$ at the time point $t_m$ may be defined by $y_m = \Delta y_1 + ... + \Delta y_m$, and the z coordinate $z_m$ at the time point $t_m$ may be defined by $z_m = \Delta z_1 + ... + \Delta z_m$. The ordered set $\{(x_m, y_m, z_m, t_m): m=1, 2, \ldots, M\}$ formed in this way provides an example of the position history data.

The aspects of the position history data are not limited to the above examples. For example, the position information is not limited to three-dimensional coordinates, but may be one-dimensional coordinates or two-dimensional coordinates. Also, the position history data is not limited to discrete data, but may be continuous data. Several aspects of position history data will be provided by the visualization data generator 235 described below.

<Visualization Data Generator 235>

The visualization data generator 235 generates visualization data of time series changes in the position of the subject's eye E, based on the position history data generated by the xy-position history data generator 232 and the z-position history data generator 234. The visualization data can be used to present the time-series changes in the position of the subject's eye E as visual information (that is, can be used for visualization). The visual information presented based on the visualization data may also be referred to as visualization data.

Graph data is an example of the visualization data generated by the visualization data generator 235. The graph data can be used to present visual information in the form of a graph representing the time series changes in the position of the subject's eye E. In some aspect examples, the graph may be any mathematical diagram or any statistical chart, such as a line graph, regression curve graph, bar graph, or heat map. Some examples of the graph data will be described below.

First, the graph data of the first example (first graph data) will be described. The first graph data represents the time series change of a predetermined directional component of the position of the subject's eye E defined by a predetermined coordinate system.

The first graph data of some aspect examples may be generated based on the xy-position history data generated by the xy-position history data generator 232 and the z-position history data generated by the z-position history data generator 234. For example, the first graph data may include one or more of the followings: graph data representing time series changes in the x-directional component of the position of the subject's eye E defined in the xyz coordinate system; graph data representing time series changes in the y-directional component of the position of the subject's eye E defined in the xyz coordinate system; and graph data representing time series changes in the z-directional component of the position of the subject's eye E defined in the xyz coordinate system.

The first graph data of some aspect examples may be generated based on the xy-position history data generated by the xy-position history data generator 232. The first graph data of this type may include, for example, one or both of the followings: graph data representing time series changes in the x-directional component of the position of the subject's eye E defined in the xy coordinate system; and graph data representing time series changes in the y-directional component of the position of the subject's eye E defined in the xy coordinate system.

The first graph data of some aspect examples may be generated based on the z-position history data generated by the z-position history data generator 234. The first graph data of this type may include, for example, graph data representing time series changes in the z-directional component of the position of the subject's eye E defined by the z coordinate system (i.e., defined by the z coordinate axis).

Graph data representing the time series changes in the x-directional component (first graph data) may be defined, for example, by a two-dimensional orthogonal coordinate system having the time axis (t) and the x axis (x). Using the coordinate description method described above, the graph data representing the time series changes in the x-directional component (the first graph data) may be graph data representing the ordered set $\{(t_m, \Delta x_m): m=1, 2, \ldots, M\}$, or graph data representing the ordered set $\{(t_m, x_m): m=1, 2, \ldots, M\}$. The same may be applied to graph data representing time series changes in the y-directional component and/or graph data representing time series changes in the z-directional component.

The first graph data may be formed by projecting time series changes in the three-dimensional position (x coordinate, y coordinate, and z coordinate) of the subject's eye E in (along) a predetermined direction (e.g., x direction, y direction, or z direction). The projection direction in this process is not limited to the x direction, the y direction, and the z direction. The projection direction may be any direction that is angled against all of the x direction, the y direction, and the z direction.

Next, the second example of graph data (second graph data) will be described. The second graph data represents time series changes in the two-dimensional position of the subject's eye E defined by a predetermined two-dimensional coordinate system.

The second graph data in some aspect examples may be generated based on the xy-position history data generated by the xy-position history data generator 232 and the z-position history data generated by the z-position history data generator 234. For example, the second graph data may include one or more of the followings: graph data representing the time series changes in a two-dimensional position (x coordinate and y coordinate) of the subject's eye E defined by the xy coordinate system; graph data representing the time series changes in a two-dimensional position (y coordinate and z coordinate) of the subject's eye E defined by the yz coordinate system; and graph data representing the time series changes in a two-dimensional position (z coordinate and x coordinate) of the subject's eye E defined by the zx coordinate system.

The second graph data of some aspect examples may be generated based on the xy-position history data generated by the xy-position history data generator 232, and may include, for example, graph data representing time series changes in a two-dimensional position (x-coordinate and y-coordinate) of the subject's eye E defined by the xy coordinate system.

The second graph data may be formed by projecting time series changes in the three-dimensional position (x coordinate, y coordinate, and z coordinate) of the subject's eye E onto a predetermined plane (e.g., xy plane, yz plane, or zx plane). The projection plane in this process is not limited to the xy plane, the yz plane, and the zx plane. The projection plane may be a plane of any orientation that is angled against all of the xy plane, the yz plane, and the zx plane.

Next, the third example of graph data (third graph data) will be described. The third graph data represents time series changes in the three-dimensional position of the subject's eye E defined by a three-dimensional coordinate system.

The third graph data of some aspect examples may be generated based on the xy-position history data generated by the xy-position history data generator 232 and the z-position history data generated by the z-position history data generator 234. For example, the third graph data may include graph data representing time series changes in the three-dimensional position (x coordinate, y coordinate, and z coordinate) of the subject's eye E defined by the xyz coordinate system.

Next, the fourth example of graph data (fourth graph data) will be described. The fourth graph data represents time series changes in the velocity of the motion of the subject's eye E.

The velocity of the motion of the subject's eye E may include velocity in three-dimensional space defined by a three-dimensional coordinate system, velocity in two-dimensional space, and velocity in one-dimensional space. In some aspect examples, the velocity $v_m$ at the time point $t_m$ may include three-dimensional velocity calculated using the formula $(\Delta x_m^2 + \Delta y_m^2 + \Delta z_m^2)^{1/2}/(t_m - t_{m-1})$ or the formula $(\Delta x_{m+1}^2 + \Delta y_{m+1}^2 + \Delta z_{m+1}^2)^{1/2}/(t_{m+1} - t_m)$. In some aspect examples, the velocity $v_m$ at the time point $t_m$ may include one or more of the followings: two-dimensional velocity (velocity in the xy plane) calculated using the formula $(\Delta x_m^2 + \Delta y_m^2)^{1/2}/(t_m - t_{m-1})$ or the formula $(\Delta x_{m+1}^2 + \Delta y_{m+1}^2)^{1/2}/(t_{m+1} - t_m)$; two-dimensional velocity (velocity in the yz plane) calculated using the formula $(\Delta y_m^2 + \Delta z_m^2)^{1/2}/(t_m - t_{m-1})$ or the formula $(\Delta y_{m+1}^2 + \Delta z_{m+1}^2)^{1/2}/(t_{m+1} - t_m)$; and two-dimensional velocity (velocity in the zx plane) calculated using the formula $(\Delta z_m^2 + \Delta x_m^2)^{1/2}/(t_m - t_{m-1})$ or the formula $(\Delta z_{m+1}^2 + \Delta x_{m+1}^2)^{1/2}/(t_{m+1} - t_m)$ In some aspect examples, the velocity $v_m$ at the time point $t_m$ may include one or more of the followings: one-dimensional velocity (velocity in the x direction) calculated using the formula $\Delta x_m/(t_m - t_{m-1})$ or the formula $\Delta x_{m+1}/(t_{m+1} - t_m)$; one-dimensional velocity (velocity in the y direction) calculated using the formula $\Delta y_m/(t_m - t_{m-1})$ or the formula $\Delta y_{m+1}/(t_{m+1} - t_m)$; and one-dimensional velocity (velocity in the z direction) calculated using the formula $\Delta z_m/(t_m - t_{m-1})$ or the formula $\Delta z_{m+1}/(t_{m+1} - t_m)$.

The fourth graph data representing time series changes in one-dimensional velocity is not limited to graph data corresponding to the x direction, graph data corresponding to the y direction, or graph data corresponding to the z direction. The fourth graph data representing time series changes in one-dimensional velocity may be graph data representing time series changes in the velocity of the motion of the subject's eye E in any direction that is oblique to all of the x direction, the y direction, and the z direction.

Similarly, the fourth graph data representing time series changes in two-dimensional velocity is not limited to graph data corresponding to the xy plane, graph data corresponding to the yz plane, or graph data corresponding to the zx plane. The fourth graph data representing time series changes in two-dimensional velocity may be graph data representing time series changes in the velocity of the motion of the subject's eye E in a plane of any orientation that is oblique to all of the xy plane, the yz plane, and the zx plane.

The coordinate system used for graph data generation is not limited to the xyz coordinate system or a coordinate system that is part of the xyz coordinate system. The coordinate system used for graph data generation may be any coordinate system that can be used to represent the position of the subject's eye E.

Specific examples of graph data will be described later.

Visualization data is not limited to graph data of the above-described aspects. Visualization data may be any data for performing visualization based on the xy-position history data and/or the z-position history data.

In some examples, the visualization data generator 235 may be configured to generate visualization data representing a frequency component(s) of the motion of the subject's eye E (frequency component(s) of eye movement). As described in Japanese Unexamined Patent Application Publication No. 2007-130403 (United States Patent Application Publication No. 2010/0142780) and "Heartbeat-Induced Axial Motion Artifacts in Optical Coherence Tomography Measurements of the Retina" (Roy de Kinkelder, et al., IOVS, May 2011, Vol. 52, No. 6, pp. 3908-3913), it is known that there exists a pulse-shaped (almost periodic) motion artifact in the depth direction (z direction) caused by heartbeat. Visualization data of this pulse-shaped motion artifact may be data representing time series changes in z-shift amounts, such as graph data defined by the time axis and the z axis.

The ophthalmic examination apparatus 1 may be configured to extract motion artifacts caused by heartbeat from z-position history data (or, from three-dimensional position history data generated by combining xy-position history data and z-position history data), and to evaluate this heartbeat-induced motion artifacts. This makes it possible to obtain heartbeat-induced motion data of the subject's eye E with a high degree of accuracy. The ophthalmic examination apparatus 1 may also be capable of removing the heartbeat-induced motion artifacts from the z-position history data or the three-dimensional position history data. This makes it possible to obtain motion data of the subject's eye E with the influence of heartbeat removed. By using Lissajous scanning to generate the data described above, it is considered that it becomes possible to perform evaluation of heartbeat-induced motion artifacts and evaluation of eye movements such as nystagmus with a higher degree of accuracy than existing or conventional techniques.

<Image Data Corrector 236>

The image data corrector 236 is configured to apply position adjustment in the z direction based on the z-shift amount obtained by the z-shift amount calculator 233 (the set of z-shift amounts collected by the z-position history data generator 234), to the plurality of sub-volumes whose positions in the xy direction have been adjusted by the image data processor 231.

As in the registration processor 2317 that performs registration based on an xy-shift amount, the image data corrector 236 performs registration between a reference sub-volume and a registering sub-volume in such a manner as to eliminate (cancel) or reduce a corresponding z-shift amount obtained by the z-shift amount calculator 233.

As mentioned above, the image data corrector 236 of some examples may be controlled to perform registration between a reference sub-volume and a registering sub-volume only if a corresponding z-shift amount exceeds a threshold value.

Image data obtained as a result of the position adjustment performed by the image data corrector 236, is a group of sub-volumes that have already been registered in all of the x direction, they direction, and the z direction, that is, a group of sub-volumes whose positions have already been adjusted in all of the x direction, the y direction, and the z direction. In other words, image data obtained as a result of the position adjustment performed by the image data corrector 236, is a group of sub-volumes that have undergone three-dimensional registration. A group of sub-volumes prior to application of this three-dimensional registration is a volume collected by Lissajous scanning. The data processor 230 recombines the sub-volumes obtained by the three-dimensional registration. This yields a volume to which the three-dimensional registration has been applied.

This three-dimensionally registered data set may be used for any processes or any operations, such as image processing, post-processing, analysis, evaluation, visualization, and rendering. This makes it possible to perform desired processes or operations using the three-dimensional data set with motion artifacts corrected with higher accuracy and precision than existing or conventional techniques.

The z-shift amount calculator 233 and the image data corrector 236 may be configured to remove or reduce motion artifacts in the z direction by performing registration corresponding to the axial motion correction (rough axial motion correction and/or fine axial motion correction) of Non-patent document 1 (see pages 1789 to 1790).

<Evaluation Data Generator 237>

The evaluation data generator 237 is configured to generate evaluation data based on the xy-position history data generated by the xy-position history data generator 232 and/or the z-position history data generated by the z-position history data generator 234.

The evaluation data may be any data on one or more freely selected evaluation items that can be used in the field of ophthalmology and/or any other fields. While some examples of the evaluation data and some examples of processing executable by the evaluation data generator 237 will be described below, the aspects or kinds of the evaluation data and the contents of the processing performed by the evaluation data generator 237 are not limited to the following examples.

The evaluation data generator 237 may be configured to generate evaluation data on the reliability (confidence) of a predetermined process. This evaluation data is referred to as reliability evaluation data. The reliability evaluation data of some examples includes one or more of the followings: evaluation data on the reliability of a process itself that is to be evaluated; evaluation data on the reliability of one or more processes (one or more sub-processes) included in a process to be evaluated; evaluation data on the reliability of a process that includes a process to be evaluated as its sub-process; evaluation data on the reliability of a result (output) of a process to be evaluated; and evaluation data on the reliability of an input to a process to be evaluated.

In the present disclosure, reliability refers to a property (or ability) or probability that a process to be evaluated can perform a predetermined required function (role) under a given condition. This reliability is also referred to as a degree of confidence, credibility, or the like. Reliability evaluation data may include one or more of information representing the presence or absence of reliability, information representing the degree of reliability, and quantified information of reliability.

In some aspect examples, reliability evaluation data may include reliability evaluation data of motion artifact correction. In the present aspect example, reliability evaluation data may include reliability evaluation data of motion artifact correction in the xy direction performed by the image data processor 231, and may include reliability evaluation data of motion artifact correction in the z direction performed by the z-shift amount calculator 233 and the image data corrector 236.

As mentioned above, the image data constructing unit 220 constructs a plurality of pieces of image data (e.g., a plurality of sub-volumes, a plurality of strips) based on a data set collected by Lissajous scanning. The image data processor 231 functions as a position correcting processor and performs relative position correction (motion artifact correction in the xy direction) between the plurality of pieces of image data. The z-shift amount calculator 233 and the image data corrector 236 also function as a position correcting processor and perform relative position correction (motion artifact correction in the z-direction) between the plurality of pieces of image data. The evaluation data generator 237 of the present example is configured to generate any one or both of the followings: reliability evaluation data of motion artifact correction in the xy direction; and reliability evaluation data of motion artifact correction in the z direction.

Machine learning may be used to generate reliability evaluation data. For example, as shown in FIG. 4D, the evaluation data generator 237 may include the inference model 2371. The inference model 2371 is trained in advance by machine learning using training data. The method of this machine learning may be freely selected from among known techniques, and may include one or more of supervised learning, unsupervised learning, reinforcement learning, and other techniques.

In some examples, the training data may include a set of position history data collected using the same or similar process as or to the process executed by the data processor 230. This position history data is data representing time series changes in the position of an eye. The training data may include a set of processed data generated by processing such position history data. This processed data may be of a type that can be generated by the data processor 230, and may include, for example, any of the various kinds of visualization data described above. In the case where supervised learning is used, the training data may further include, for example, labels assigned to individual pieces of position history data and/or individual pieces of processed data. Each of the labels is data representing reliability (reliability level, confidence, confidence level), and may include, for example, one or more of the followings: a label representing "success" of motion artifact correction (Lissajous scanning, photography, imaging); a label representing "failure" of motion artifact correction (Lissajous scanning, photography, imaging); and a label representing "success probability (numerical value, numerical data)".

Input (input data) to the inference model 2371 includes position history data and/or processed data, such as visualization data, generated by the data processor 230. Output (output data) from the inference model 2371 in response to the input data, includes reliability. In some examples, the reliability output from the inference model 2371 may be information representing one or more of "success", "failure", and "success probability (numerical value)" of motion artifact correction (Lissajous scanning, photography, imaging).

In the present aspect example, input data to the inference model 2371 at least includes one or more of the followings: the xy-position history data of the subject's eye E generated by the xy-position history data generator 232; the z-position history data of the subject's eye E generated by the z-position history data generator 234; and the visualization data generated by the visualization data generator 235. The inference model 2371 may generate reliability evaluation data of motion artifact correction (relative position correction) based on this input data.

In this way, the evaluation data generator 237 generates reliability evaluation data of motion artifact correction based on characteristics of the subject's eye E during the period of time while Lissajous scanning was being performed on the subject's eye E, such as characteristics of shifts in the x direction, characteristics of shifts in the y direction, and/or characteristics of shifts in the z direction. These shift characteristics may be any kinds of characteristics related to movements (shifts) of the subject's eye E. For example, the shift characteristics may include one or more of the followings: shift amounts; a statistical value of shift amounts (e.g., maximum value, minimum value, average value, standard deviation); a time series change in shift amounts; a parameter value of a graph of a time series change in shift amounts (e.g., frequency, amplitude); shift velocity; a statistical value of shift velocity; a time series change in shift velocity; and a parameter value of a graph of a time series change in shift velocity.

The data input to the inference model 2371 is not limited to shift characteristics of the subject's eye E. In some examples, data related to blinks (blink data) of the subject's eye E may be input to the inference model 2371 together with shift characteristics. The blink data of some examples includes any parameter(s) of blinks of the subject's eye E during the period of time while Lissajous scanning was being performed on the subject's eye E, such as the presence or absence of blinks, the number of times of blinks, the frequency of blinks, and time points of blinks. The blink data of some examples may include data calculated by integrating a predetermined parameter over at least part of the period of time while Lissajous scanning was being applied to the subject's eye E.

In the case where training data also includes data of a given item related to eyes, such as blink data, the inference model 2371 trained using this training data is configured to receive any one or both of position history data and processed data of this position history data and receive any one or both of data of this item and processed data of this data as inputs, and generate data of reliability level as an output.

The ophthalmic examination apparatus 1 of the present example has the function of obtaining data on the above-mentioned item concerning the subject's eye E. The ophthalmic examination apparatus 1 may be configured to generate data on the item by conducting examination on the subject's eye E. For example, the ophthalmic examination apparatus 1 may be configured to generate blink data by executing analysis of an observation image obtained by the fundus camera unit 2. In some other examples, the ophthalmic examination apparatus 1 may be configured to generate blink data by executing analysis of a moving image obtained by the above-described two or more anterior segment cameras used for stereo alignment. Similarly, in the case where data on an item other than blink is generated, the ophthalmic examination apparatus 1 may generate data on this item by conducting acquisition and analysis of an image of the subject's eye E. On the other hand, the ophthalmic examination apparatus 1 of some examples may be configured to receive data of the subject's eye E on a predetermined item, from an external source. For example, the ophthalmic examination apparatus 1 may have a component (element, part, unit, device) configured to acquire data on a predetermined item for the subject's eye E from external equipment such as a computer, storage device, recording medium, information system, or any other equipment. Examples of this component is the data receiving unit 250 described later. The ophthalmic examination apparatus 1 of the present example may be configured to process the generated or received data on a predetermined item of the subject's eye E, to generate new data (another data, processed data).

The evaluation data generator 237 of the present example feeds, into the inference model 2371, one or both of data of a predetermined item of the subject's eye E and its processed data, as well as one or both of position history data of the subject's eye E and its processed data (e.g., visualization data) generated by the data processor 230. The inference model 2371 then generates reliability evaluation data for motion artifact correction based on the input data.

Several examples of the inference model 2371 will be described. The first example of the inference model 2371 includes a feature extractor and a support vector machine (SVM). The feature extractor is configured to extract features from input data. The support vector machine is configured to receive the extracted features as input and generate reliability evaluation data as output.

The feature extractor of some examples may be configured by using any known feature engineering techniques. The support vector machine is a pattern recognition model using supervised learning techniques. The support vector machine is a technique of configuring a two-class pattern discriminator using linear input elements, and executes learning of the parameters of the linear input elements by using, as a criterion (the hyperplane separation theorem), the process of finding the maximum-margin hyperplane (optimally separating hyperplane) that maximizes the distance between training data (training samples) and each data point. The support vector machine of the present example performs inference (e.g., classification, regression, etc.) based on the feature extracted by the feature extractor.

The evaluation data generator 237 with the inference model 2371 configured in this manner is capable of determining, as a feature, any parameters of the motion of the subject's eye E such as the amplitude and frequency of the motion of the subject's eye E by, for example, applying frequency analysis to the position history data and/or the visualization data generated by the data processor 230. The evaluation data generator 237 in the present example is capable of determining, as a feature, the total blinking time of the subject's eye E during the period of time while Lissajous scanning was being performed, based on the blink data. By inputting such a feature(s) into the support vector machine, the evaluation data generator 237 in the present example is capable of classifying (identifying, discriminating, judging) whether the motion artifact correction (Lissajous scanning, photography) was performed successfully or unsuccessfully, and also calculating the success probability (reliability) of the motion artifact correction (Lissajous scanning, photography).

The second example of the inference model 2371 includes a neural network (NN) that generates reliability evaluation data from input data. The neural network of the present example may be a trained convolutional neural network (CNN) that has been trained using the same kind of data set as input data. Here, the input data may include, for example, position history data, visualization data, blink data, or any other kinds of data. In addition, the data set used for the training of the convolutional neural network may be accompanied by labels such as successful Lissajous scanning, unsuccessful Lissajous scanning, success probability of Lissajous scanning (reliability of Lissajous scanning).

Several examples of the convolutional neural network will be described. Data of a predetermined kind (e.g., position history data, visualization data, blink data) is input to an input layer of the convolutional neural network. This input data is typically an image. Behind the input layer, a plurality of pairs of a convolutional layer and a pooling layer is disposed. The number of these pairs may be freely determined. In the convolutional layer, a convolution operation is performed to detect or extract a feature (e.g., contour) from the input image. This convolution operation is a multiply-accumulate operation (a multiply-add operation, a product-sum operation) on the input image. This multiply-accumulate operation is performed with a filter function (a weight coefficient, a filter kernel) having the same dimension as the input image. In the convolutional layer, the convolution operation is applied to individual parts (individual sections, individual portions) of the input image. More specifically, the convolutional layer is configured to calculate a product by multiplying the value of each pixel in a partial image, to which the filter function has been applied, by the value (weight) of the filter function corresponding to this pixel, and then calculate the sum of the products over a plurality of pixels in this partial image. The sum of products obtained in this way is substituted for the corresponding pixel in an image to be output from the convolutional layer. By repetitively performing such multiply-accumulate operation in parallel with moving sites (parts) to which the filter function is applied (that is, in parallel with changing or switching partial images of the input image), a result of the convolution operation for the entire input image is obtained. The convolution operation performed in this way gives a large number of images in which various features have been extracted using a large number of weight coefficients. This means that a large number of filtered images, such as smoothed images and edge images, are obtained. The large number of images generated by the convolutional layer are referred to as feature maps (or activation maps). The pooling layer executes data compression (e.g., data thinning) of the feature maps generated by the convolutional layer arranged at the immediately preceding position. More specifically, the pooling layer calculates statistical values in predetermined neighboring pixels of a predetermined pixel of interest in an input feature map at each predetermined pixel intervals, and outputs an image having a size smaller than the input feature map. The statistical values applied to the pooling operation may be maximum values (max pooling) or average values (average pooling), for example. The value of the pixel intervals applied to the pooling operation is referred to as a stride. In general, a convolutional neural network extracts many features from an input image by executing processing using a plurality of pairs of a convolutional layer and a pooling layer. A fully connected layer is arranged behind the last pair of a convolutional layer and a pooling layer. The number of fully connected layers may be freely determined. The fully connected layer executes inference processing such as classification or regression using the features compressed by convolution and pooling. An output layer is arranged behind the last fully connected layer. The output layer gives an output result. Some aspect examples may employ a convolutional neural network including no fully connected layer. Some aspect examples may include a support vector machine, a recurrent neural network (RNN), or any other models.

The evaluation data generator 237 with the inference model 2371 configured in this manner is capable of classifying (identifying, discriminating, judging) whether the motion artifact correction (Lissajous scanning, photography) was performed successfully or unsuccessfully, and also calculating the success probability (reliability) of the motion artifact correction (Lissajous scanning, photography), based on position history data, visualization data, blink data, and/or any other data generated by the data processor 230.

The evaluation data generator 237 may be configured to generate evaluation data for individual parts of image data. This image data may be any image data constructed from a data set collected by Lissajous scanning, and examples of this image data include image data constructed by the image data constructing unit 220, image data constructed by the image data processor 231 (e.g., image data constructed by the mergence processor 2318), or image data constructed by the image data corrector 236.

In some examples, the evaluation data generator 237 may be configured to perform the process of partitioning image data into a plurality of partial regions and the process of generating evaluation data for each of the partial regions. The ophthalmic examination apparatus 1 of the present example may be configured to assign a display parameter to each of the partial regions based on corresponding evaluation data. This process may be executed by the main controller 211. This display parameter may be, for example, a color parameter corresponding to the magnitude of the degree of reliability. The main controller 211 may be configured to display a heat map of the degree of reliability, based on the color parameters assigned to individual partial regions. The heat map may be superimposed on an image of the subject's eye E, or the heat map may be synthesized with an image of the subject's eye E. These display modes provide visualization of the degrees of reliability (that is, distribution of the degrees of reliability) of individual parts of an image.

The process of displaying a heat map is also effective in wide angle photography (wide angle imaging, panoramic photography, panoramic imaging, montage photography, montage imaging). Wide angle photography is a photographing technique of applying scanning (Lissajous scanning) sequentially to a plurality of different regions of the subject's eye E, constructing a plurality of pieces of image data based on a plurality of data sets respectively collected from the plurality of regions, and synthesizing the plurality of pieces of image data into a panoramic image. Wide angle photography is achieved, for example, by moving (changing) scan target area by moving (changing) a position of fixation for the subject's eye E. The evaluation data generator 237 generates evaluation data for each of the plurality of pieces of image data corresponding to the plurality of regions. The main controller 211 assigns a display parameter (color parameter) to each image data based on a corresponding evaluation data. The main controller 211 displays a heat map representing the degrees of reliability for individual pieces of image data based on the color parameters assigned to the individual pieces of image data. The heat map may be superimposed on a panoramic image, or the heat map may be synthesized with a panoramic image. Displaying a heat map allows the degrees of reliability of individual pieces of photography (individual pieces of scanning) conducted in wide angle photography to be visualized.

The method of generating evaluation data that takes into account data other than position history data, is not limited to the methods using machine learning. For example, in some aspect examples, the evaluation data generator 237 may be configured to generate evaluation data using any method based on position history data and data on a given item. The data for the given item may include data generated by the ophthalmic examination apparatus 1 and/or data received by the data receiving unit 250.

Some application examples of evaluation using the ophthalmic examination apparatus 1 will be described. Using position history data, visualization data, and/or other kinds of data as a biomarker(s) of eye movements makes it possible to detect and evaluate neuropathy (neurological disorders), such as nystagmus, induced by Alzheimer's disease, Parkinson's disease, or other diseases. For example, evaluation of Alzheimer's disease may be implemented by using position history data and/or visualization data as biomarkers for amyloid beta (Aβ) and by combining these biomarkers with information on thinning of retinal nerve fiber layer (RNFL) obtained from analysis of OCT image data of eye fundus (e.g., B-scan image data of eye fundus, three dimensional image data of eye fundus). Here, the information on thinning of retinal nerve fiber layer may be an RNFL thickness distribution.

There are other diseases for which position history data and visualization data may be used as biomarkers of eye movements. For example, carotid cavernous fistula is a disease caused by a basilar skull fracture or rupture of aneurysm, and presents with pulsating exophthalmos, pulsating noise in orbit, hyperemia of conjunctiva, external ophthalmoplegia, visual impairment, diplopia, increased intraocular pressure, retinal hemorrhage, papilledema, etc. These symptoms of carotid cavernous fistula are similar to those of conjunctivitis. Therefore, careful differential diagnosis is required. When an ophthalmologist suspects of this disease, it is usual to listen for noises in an eye ball and orbit with a stethoscope (bell side) and refer the patient to a neurosurgery specialist. By combining these existing or conventional medical procedures with some aspect examples that employs application of the present embodiment, evaluation of pulsating exophthalmos, external ophthalmoplegia, etc. can be performed by using position history data, visualization data, and/or other data as biomarkers of eye movements.

<Position History Data Corrector 238>

The position history data corrector 238 performs correction of position history data based on time series data acquired from the subject. As shown in FIG. 4B and FIG. 4C, the xy-position history data generated by the xy-position history data generator 232 and the z-position history data generated by the z-position history data generator 234 are input to the position history data corrector 238. The position history data corrector 238 performs any one or both of correction of the xy-position history data and correction of the z-position history data.

Examples of correction of position history data will be described. In the case where the ophthalmic examination apparatus 1 includes a stereo camera (illustration omitted), the motion of the subject's eye E (including eye movements and head movements) can be evaluated by detecting the center of the pupil from a pair of moving images of anterior eye segment of the subjects eye E acquired by the stereo camera and by detecting a time series change in the position of the center of the pupil. Further, evaluation of eye movements and evaluation of head movements can be performed separately from one another by detecting a site (e.g., outer canthus, inner canthus, eyelid) other than the center of pupil as a feature point and by subtracting the displacement of this feature point from the displacement of the center of pupil.

The xy-position history data generated by the xy-position history data generator 232 and the z-position history data generated by the z-position history data generator 234 (as well as evaluation data and visualization data generated based on the xy-position history data and/or the z-position history data) contain not only information on eye movements but also information on head movements. In order to detect and evaluate eye movements with a high degree of accuracy, it is desirable to remove motions of the subject's eye E originating from sources other than eye movements (e.g., head movements) from position history data (visualization data, evaluation data).

Accordingly, the position history data corrector 238 of the present aspect example is configured to remove motions of the subject's eye E originating from factors other than eye movements (e.g., head movements) from position history data by using the above information obtained using the stereo camera (separation between the motion of the subject's eye E originating from eye movements and the motion of the subject's eye E originating from factors other than eye movements).

Figure 6:
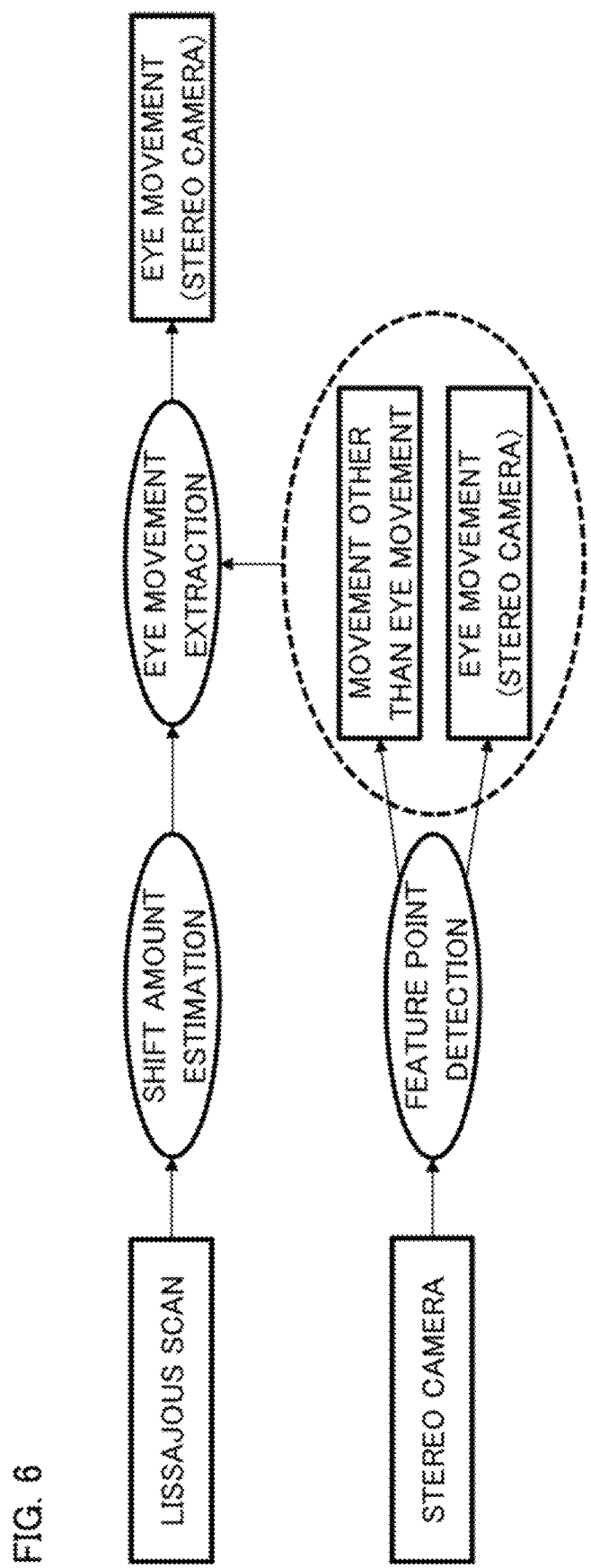
FIG. 6 illustrates an example of processing that can be performed by an ophthalmic examination apparatus according to the present disclosure.
Figure 7A:
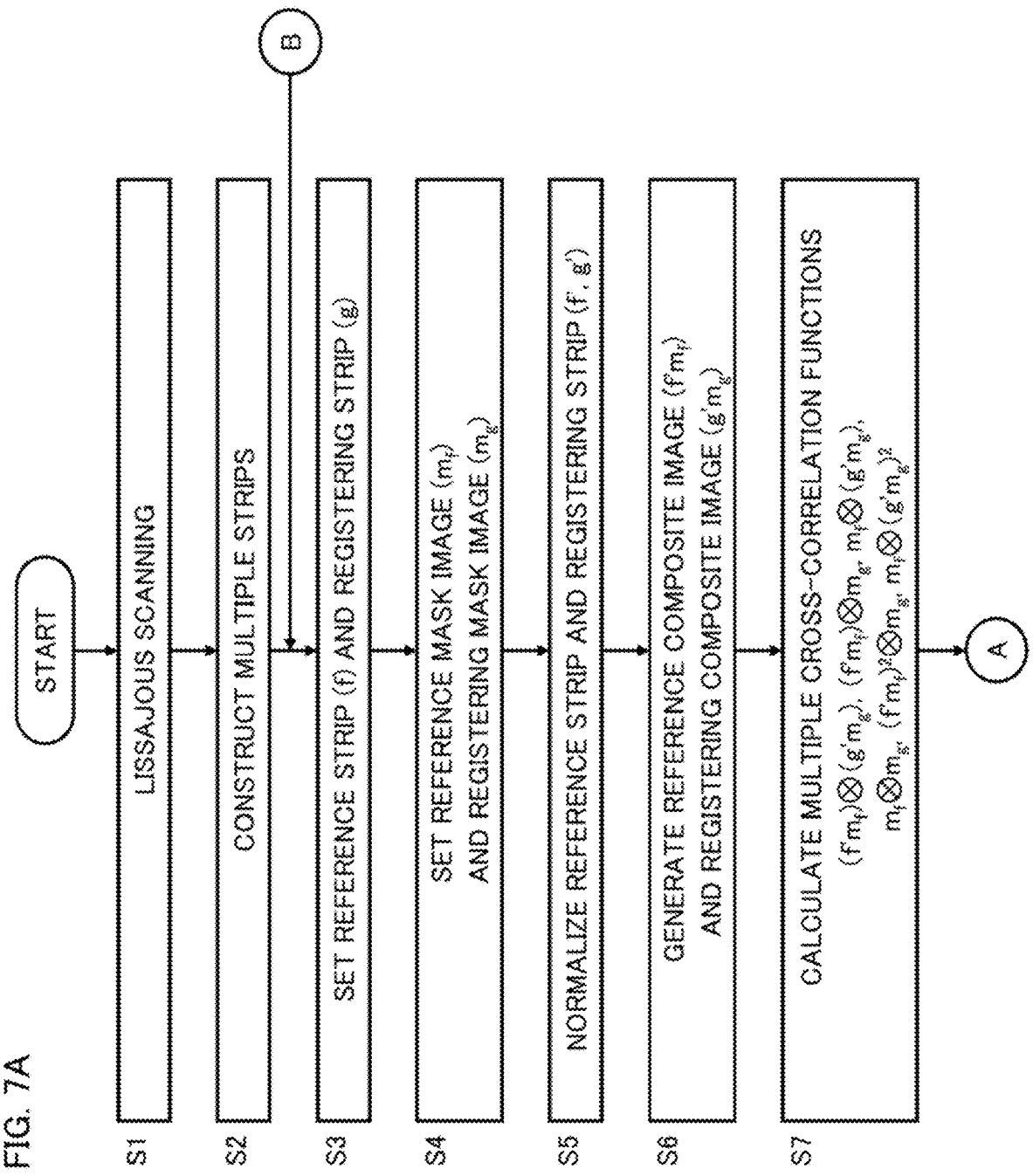
FIG. 7A illustrates a flowchart of an example of the operation of an ophthalmic examination apparatus according to the present disclosure.
Figure 7B:
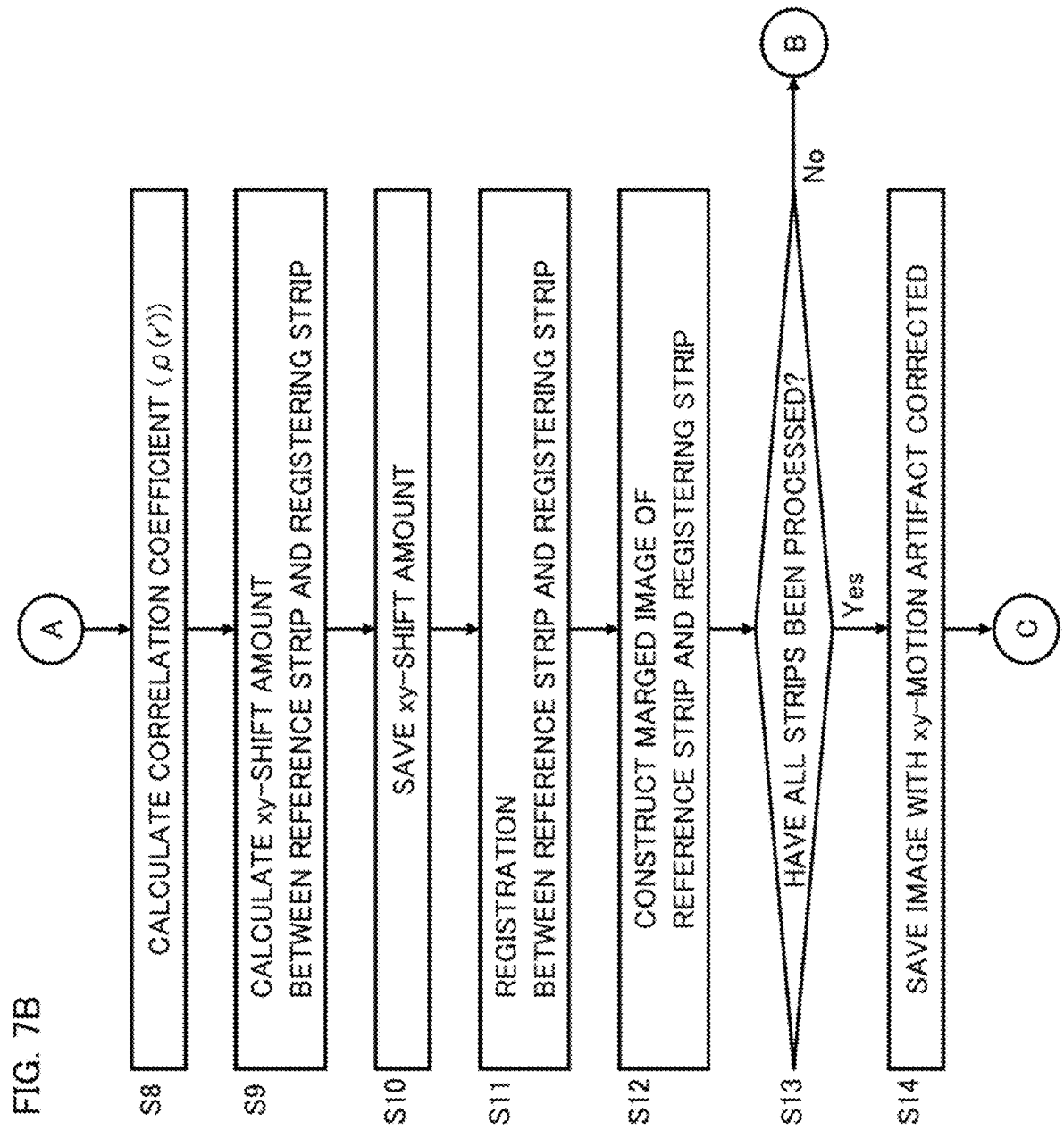
FIG. 7B illustrates a flowchart of an example of the operation of an ophthalmic examination apparatus according to the present disclosure.
Figure 7E:
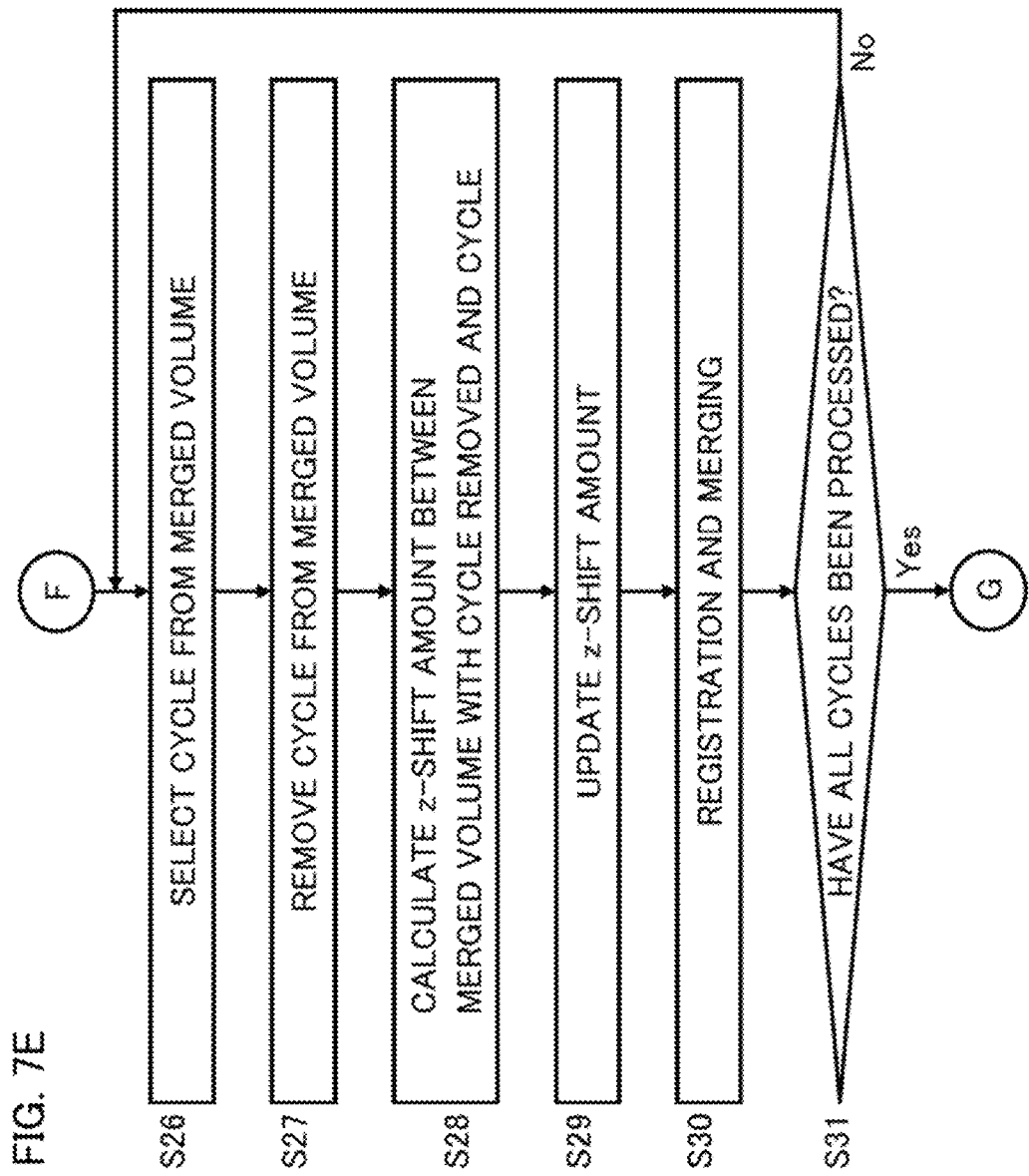
FIG. 7E illustrates a flowchart of an example of the operation of an ophthalmic examination apparatus according to the present disclosure.

In some examples, the position history data corrector 238 first performs the process of aligning the time axis of the position history data with the time axis of time series data of the motion of the subject's eye E originating from factors other than eye movements obtained using the stereo camera. Note that the position history data is time series data, and that this time series data of the motion of the subject's eye E originating from the factors other than eye movements is referred to as time series data for correction. Next, the position history data corrector 238 extracts the eye movement component from the position history data by subtracting the time series data for correction from the position history data. The detection of the motion of the subject's eye E using the stereo camera can detect the three-dimensional motion of the subject's eye E (the motion in the x direction, the motion in the y direction, and the motion in the z direction), and the position history data corrector 238 is capable of subtracting the time series data for correction from the position history data in the x direction, subtracting the time series data for correction from the position history data in the y direction, and subtracting the time series data for correction from the position history data in the z direction. FIG. 6 illustrates a process flow that can be used in the case where the above position history data correction is performed.

The visualization data generator 235 may be configured to generate visualization data from the position history data corrected by the position history data corrector 238. With this configuration, it becomes possible to obtain visualization data corresponding to eye movements. The evaluation data generator 237 may be configured to generate evaluation data based on the position history data corrected by the position history data corrector 238 and/or visualization data generated from this corrected position history data. With this configuration, it becomes possible to obtain evaluation data corresponding to eye movements.

The same or similar data correction as or to the correction performed by the position history data corrector 238 may be applied to visualization data generated by the visualization data generator 235 based on the xy-position history data generated by the xy-position history data generator 232 and/or the z-position history data generated by the z-position history data generator 234. This allows visualization data corresponding to eye movements to be obtained. This visualization data correction process is performed by the data processor 230 (by a visualization data corrector not shown in the diagrams).

The same or similar data correction as or to the correction performed by the position history data corrector 238 may be applied to evaluation data generated by the evaluation data generator 237 based on the xy-position history data generated by the xy-position history data generator 232 and/or the z-position history data generated by the z-position history data generator 234. This allows evaluation data corresponding to eye movements to be obtained. This evaluation data correction process is performed by the data processor 230 (by an evaluation data corrector not shown in the diagrams).

The technologies and techniques that can be combined with detection, analysis, evaluation, and/or other processes of the motion of the subject's eye E using Lissajous scanning are not limited to a stereo camera (detection, analysis, evaluation, and/or other processes of the motion of the subject's eye E using a stereo camera). In some aspect examples, any measurement technique may be combined with position history data generation and/or evaluation data generation. The typical example of this measurement technique may be any kind of medical techniques used for acquiring data related to eye movements (e.g., time series data). Examples of such medical techniques include Doppler measurements, infrared imaging, heart rate measurements, optical coherence elastography (OCE), and other techniques.

For example, a technique of measuring the hardness (stiffness) of a tissue using optical coherence elastography is known. While this existing or conventional technique employs optical coherence elastography imaging using phase information to evaluate small movements, the present embodiment can provide a novel measurement technique of estimating tissue stiffness from measurement data of the aforementioned heartbeat-derived pulsating vibration in the depth direction, that is, from measurement data of motion artifacts.

<User Interface 240>

The user interface 240 includes the display device 241 and the operation device 242. The display device 241 includes the display device 3. The operation device 242 includes various operation devices and various input devices. The user interface 240 may include a device that has both a display function and an operation function, such as a touch panel. Some embodiment may not include at least part of the user interface 240. For example, the display device may be an external apparatus connected to the ophthalmic examination apparatus 1.

<Data Receiving Unit 250>

The data receiving unit 250 acquires data from an external apparatus. For example, the data receiving unit 250 receives the above-described data of the subject's eye E on the predetermined items, from the external apparatus.

Examples of the external apparatus may include, for example, a computer, a storage device (data storage), a storage medium, an information system (e.g., a hospital information system, an electronic medical record system, an image archiving system), and any other apparatuses, devices, and equipment. The external apparatus may be, for example, directly connected to the ophthalmic examination apparatus 1, connected to the ophthalmic examination apparatus 1 via a local area network (LAN), connected to the ophthalmic examination apparatus 1 via a wide area network (WAN), or connected to the ophthalmic examination apparatus 1 in other connection aspects.

The data receiving unit 250 may include, for example, a communication interface, a drive device, or other devices. The data receiving unit 250 may include a scanner for reading data recorded on a paper. The data receiving unit 250 may include an input device for a user to input data. The input device may be a keyboard, a graphics tablet, or any other devices.

<Operation>

Some aspect examples of the operation of the ophthalmic examination apparatus 1 will be described. FIG. 7A to FIG. 7F shows an example of the operation of the ophthalmic examination apparatus 1. Some aspect examples may perform only some of the processes of the present operation example. In some aspect examples, some processes of the present operation example may be replaced by other processes, such as by similar processes. In some aspect examples, any process may be combined with the present operation example.

The same preparatory processes as those performed by existing or conventional ophthalmic examination apparatuses are performed before the step S1. Examples of these preparatory processes include the process of entering a patient identifier (ID), the process of setting or designating a scanning mode (the process of setting or designating Lissajous scanning in the present aspect example), the process of presenting a fixation target, the process of alignment, the process of focus adjustment, the process of OCT optical path length adjustment, and any other processes.

(S1: Lissajous Scanning)

Upon receiving a predetermined scanning start trigger signal, the scan controller 211 starts to apply OCT scanning (Lissajous scanning) to the subject's eye E (the fundus Ef).

The scanning start trigger signal is generated, for example, in response to the completion of predetermined preparation operations (e.g., alignment, focus adjustment, OCT optical path length adjustment) or in response to a predetermined scanning start instruction operation performed using the operation device 242.

The scan controller 2111 applies Lissajous scanning to the fundus Ef by controlling predetermined elements including the optical scanner 44 and the OCT unit 100 in accordance with the scan protocol 2121 (the protocol corresponding to Lissajous scanning). Data collected by this Lissajous scanning is sent to the image data constructing unit 220.

(S2: Construct Multiple Strips)

The image data constructing unit 220 constructs a plurality of strips based on the data collected in the step S1 in the manner described above. The plurality of strips constructed are sent to the data processor 230.

(S3: Set Reference Strip and Registering Strip)

The data processor 230 sequences (defines order of) the plurality of strips constructed in the step S2 in accordance with the dimensions or sizes, such as the areas, of the plurality of strips. In the present example, the number of the plurality of strips constructed in the step S2 is denoted by EN". Here, N is an integer equal to or greater than 2. Also, in accordance with the order defined by the sequencing, these N number of strips are referred to as the first strip, the second strip, . . . , and the N-th strip. In addition, any one of the first to the N-th strips may be referred to as the n-th strip (n=1, 2, . . . N). In this way, the first strip is the largest strip, the second strip is the second largest strip, the n-th strip is the n-th largest strip, and the N-th strip is the smallest strip.

In the present example, the data processor 230 sets the first strip to the initial reference strip and the second strip to the initial registering strip.

A reference strip and a registering strip correspond to the arbitrary shaped images f(r) and g(r) in Appendix A of Non-patent document 1, respectively.

(S4: Set Reference Mask Image and Registering Mask Image)

The mask image generator 2311 generates a mask image corresponding to the reference strip set in the step S3 and a registering mask image corresponding to the registering strip set in the step S3. That is, the mask image generator 2311 generates a reference mask image and a registering mask image.

At this stage (the process of the step S4 of the first time), the mask image generator 2311 generates two mask images respectively corresponding to the two strips, that is, corresponding to the first strip and the second strip. The data processor 230 sets the first mask image corresponding to the first strip to the initial reference mask image and sets the second mask image corresponding to the second strip to the initial registering mask image.

The reference mask image corresponds to the rectangular shaped binary image mask $m_f(r)$ in Appendix A of Non-patent document 1, and the registering mask image corresponds to the rectangular shaped binary image mask $m_g(r)$.
(S5: Normalize Reference Strip and Registering Strip)

The range adjustor 2312 performs normalization on the reference strip and the registering strip set in the step S3 in the manner described above. The normalization of the strips is performed in accordance with the pixel value range of the mask images. At this stage (the process of the step S5 of the first time), the range adjustor 2312 applies the normalization to the first strip (reference strip) and the second strip (registering strip). The process performed by the range adjustor 2312 is not limited to normalization. The process performed by the range adjustor 2312 may include any of the range adjustment processes described above or any similar processes.

In the present example, the pixel value range of each mask image is included in the closed interval [0, 1]. More specifically, each mask image in the present example is a binary image in which the values of the pixels in the area corresponding to the domain (defined area) of a corresponding strip are set to "1", and the values of other pixels are set to "0".

The range adjustor 2312 performs normalization of a strip, for example, through the process of dividing the value of each pixel of this strip by the maximum pixel value in this strip, or through the process of dividing the value of each pixel of this strip by the maximum value (upper limit value) of the pixel value range (gradation range, shade range, tone range) of this strip.

In addition, the data processor 230 (the composite image generator 2313) embeds each of the strips with the normalized pixel value range into an image with the same dimensions (the same size) and the same shape as a corresponding mask image. The embedded image of the normalized first strip $f(r)$ (that is, the image into which the normalized first strip has been embedded) is almost the same as the rectangular shaped image $f'(r)$ in Appendix A of Non-patent document 1; however, the absolute value "$|f(r)|$" of the range (value range) in the image area of the first strip $f(r)$ is normalized to be equal to or smaller than "1". This embedded image is also denoted as $f(r)$.

Similarly, the embedded image of the normalized second strip $g(r)$ (that is, the image into which the normalized second strip has been embedded) is almost the same as the rectangular shaped image $g'(r)$ in Appendix A of Non-patent document 1; however, the absolute value "$|g(r)|$" of the range (value range) in the image area of the second strip $g(r)$ is normalized to be equal to or smaller than "1". This embedded image is also denoted as $g'(r)$.
(S6: Generate Reference Composite Image and Registering Composite Image)

The composite image generator 2313 generates a composite image of an embedded image of a normalized strip and a corresponding mask image.

At this stage (the process of the step S6 of the first time), the composite image generator 2313 generates a composite image of the embedded image of the normalized first strip (reference strip) and the first mask image (reference mask image), and a composite image of the embedded image of the normalized second strip (registering strip) and the second mask image (registering mask image). The former composite image is referred to as a reference composite image, and the latter composite image is referred to as a registering composite image.

The reference composite image corresponds to the combination of two rectangle shaped images $f'(r)m_f(r)$ in Appendix A of Non-patent document 1, and the registering composite image corresponds to the combination of two rectangle shaped images $g'(r)m_g(r)$ in Appendix A of Non-patent document 1. However, as mentioned above, the absolute value ROI of the value range in the image area of the first strip $f(r)$ is equal to or less than 1, and the absolute value $|g(r)|$ of the value range in the image area of the second strip $g(r)$ is equal to or less than 1.

The image 311 shown in FIG. 8A is an example of the embedded image $f(r)$ of the normalized first strip $f(r)$, and the image 321 shown in FIG. 8A is an example of the first mask image. Synthesizing these two images 311 and 321 generates the reference composite image $f'(r)m_f(r)$.

Figure 8B:
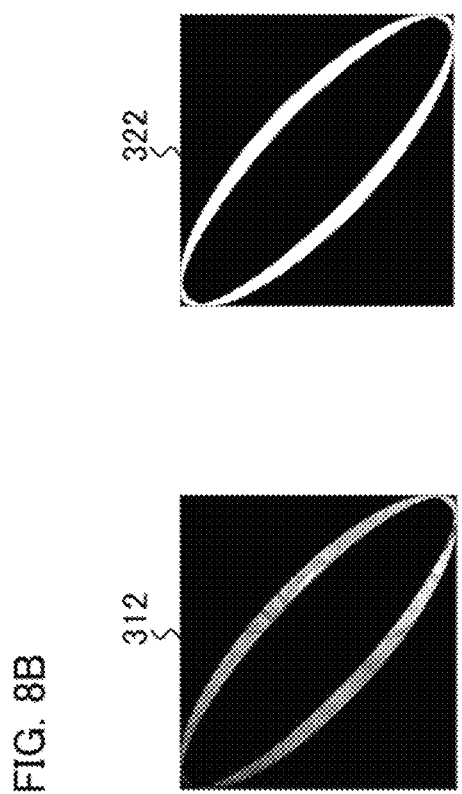
FIG. 8B illustrates a description of an example of the operation of an ophthalmic examination apparatus according to the present disclosure.

Similarly, the image 312 shown in FIG. 8B is an example of the embedded image $g'(r)$ of the normalized second strip $g(r)$, and the image 322 shown in FIG. 8B is an example of the second mask image. Synthesizing these two images 312 and 322 generates the registering composite image $g'(r)m_g(r)$.
(S7: Calculate Multiple Cross-Correlation Functions)

The cross-correlation function calculator 2314 calculates a plurality of cross-correlation functions based on the reference composite image and the registering composite image generated in the step S6. In the present example, the cross-correlation function calculator 2314 calculates the six cross-correlation functions included in the equation (33) of Non-patent document 1 based on the reference composite image and the registering composite image generated in the step S6.
(S8: Calculate Correlation Coefficient)

The correlation coefficient calculator 2315 calculates the correlation coefficient based on the plurality of cross-correlation functions calculated in the step S7. In the present example, the correlation coefficient calculator 2315 calculates the correlation coefficient $\rho(r')$ from the plurality of cross-correlation functions calculated in the step S7, according to the equation (33) of Non-patent document 1.
(S9: Calculate Xy-Shift Amount Between Reference Strip and Registering Strip)

The xy-shift amount calculator 2316 calculates the xy-shift amount between the first strip (reference strip) $f(r)$ and the second strip (registering strip) $g(r)$ based on the correlation coefficient calculated in the step S8. In the present example, the xy-shift amount calculator 2316 detects the peak of the correlation coefficient $\rho(r')$ calculated in the step S8, thereby determining the relative xy-shift amount ($\Delta x$, $\Delta y$) between the reference strip $f(r)$ and the registering strip $g(r)$.
(S10: Save Xy-Shift Amount)

The xy-shift amount calculated for the strip pair in the step S9 is sent to the xy-position history data generator 232 and saved therein. The xy-position history data generator 232, for example, records the xy-shift amount together with time information corresponding to this strip pair.

The time information may be a time parameter corresponding to Lissajous scanning or information generated from this time parameter, or may be order information on Lissajous scanning or information generated from this order information. The order information on Lissajous scanning may be, for example, the scan order of the plurality of cycles, the order of the plurality of strips based on the scan order, or any other information.

The xy-position history data generator 232 generates xy-position history data by recording a plurality of xy-shift amounts sequentially acquired through the repetition of the steps S3 to S12 together with the time information.

(S11: Registration Between Reference Strip and Registering Strip)

Based on the xy-shift amount calculated in the step S9, the registration processor 2317 applies registration in the xy direction (rough lateral motion correction) to the reference strip and the registering strip. At this stage (the process of the step S11 of the first time), performed is the registration between the first strip and the second strip.

In addition, the registration processor 2317 may apply any xy-directional registration (lateral registration), such as the "fine lateral motion correction" described above, to the reference strip and the registering strip.

(S12: Construct Merged Image of Reference Strip and Registering Strip)

Figure 8C:
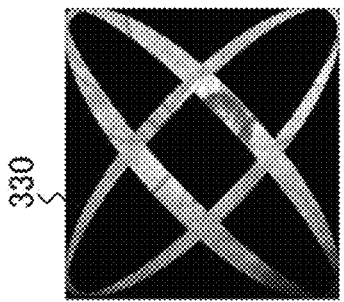
FIG. 8C illustrates a description of an example of the operation of an ophthalmic examination apparatus according to the present disclosure.

The mergence processor 2318 constructs a merged image of the reference strip and the registering strip whose relative positions has been corrected by the registration in the step S11. The image 330 in FIG. 8C shows an example of a merged image of the first strip and the second strip.

An example of the implementation of the processes of the steps S7 to S12 will now be described. First, the imaginary part or $f'(r)m_f(r)$, the imaginary part or $g'(r)m_g(r)$, the imaginary part or $m_f(r)$, the imaginary part or $m_g(r)$, the imaginary part or $(f'(r)m_f(r))^2$, and the imaginary part or $(g'(r)m_g(r))^2$ are all set to 0, and only their real parts will be used.

Then, fast Fourier transform (FFT) is applied to the real part of each of $f'(r)m_f(r)$, $g'(r)m_g(r)$, $m_f(r)$, $m_g(r)$, $(f'(r)m_f(r))^2$, and $(g'(r)m_g(r))^2$.

Next, the six cross-correlation functions described in the step S7 of FIG. 6 are calculated based on the set of functions obtained by these fast Fourier transforms.

Next, an inverse fast Fourier transform (IFFT) is applied to each of the six cross-correlation functions.

Next, the correlation coefficient $\rho(r')$ is calculated according to the equation (33) of Non-patent document 1.

Next, the relative shift ($\Delta x$, $\Delta y$) between the reference strip f(r) and the registering strip g(r) is calculated by finding the peak position of the correlation coefficient $\rho(r')$, and then the registration and merging process between the reference strip f(r) and the registering strip g(r) are performed based on the relative shift ($\Delta x$, $\Delta y$) calculated.

By sequentially applying such a series of processes to the N pieces of strips, a merged image of all these strips is obtained. In addition, the xy-shift amounts ($\Delta x$, $\Delta y$) calculated for individual strip pairs (the xy-shift amount ($\Delta x$, $\Delta y$) calculated for each pair of a reference strip and a registering strip) are saved together with time information. That is, each of the xy-shift amounts ($\Delta x$, $\Delta y$) respectively calculated for the strip pairs is associated with corresponding time information and saved.

(S13: Have all Strips been Processed?)

For all the N pieces of strips obtained in the step S2, the series of the steps S3 to S12 is conducted sequentially in accordance with the order described above.

In the case where the number N is 3 or more and where the merged image of the first strip and the second strip has been created in the step S12 (S13: No), the process returns to the step S3. In this step S3 (second time), the merged image of the first and second strips is set to a new reference strip, and the third strip is set to a new registering strip. By executing the steps S4 to S12 based on this new reference strip and this new registering strip, a merged image of the new reference strip and the new registering strip is obtained. This new merged image is a merged image of the first strip, the second strip, and the third strip. By applying such a series of processes sequentially to the N pieces of strips, a merged image of all the N pieces of strips is constructed (S13: Yes).

(S14: Save Image with Xy-Motion Artifact Corrected)

The merged image finally obtained by the repetitive process described above is not only an image in which motion artifacts in the xy direction have been corrected, but also an image that represents the entire area to which Lissajous scanning has been applied in the step S1. The main controller 211 stores this final merged image in the memory 212 (and/or other storage devices).

The data processor 230 may use the results of the registration based on the N pieces of strips to conduct registration of the data collected in the step S1 (three-dimensional data) and/or registration of three-dimensional image data constructed by the image data constructing unit 220 from the three-dimensional data collected in the step S1. In other words, the data processor 230 may perform registration of the three-dimensional data and/or the three-dimensional image data using the final merged image. This registration includes the process of transforming the coordinate system used for the definition of Lissajous scanning into a three-dimensional orthogonal (Cartesian) coordinate system (xyz coordinate system). This coordinate transformation (coordinate conversion) corresponds to the "remapping" of the technique described in Non-patent document 1. In this way, three-dimensional image data (volume) with xy-directional motion artifacts corrected is obtained. The main controller 211 may store this xy-directional motion artifact-corrected volume in the memory 212 (and/or other storage devices) together with or in place of the final merged image.

(S15: Select Reference Strip)

Next, the process for correcting motion artifacts in the z direction is performed. In this z-directional motion artifact correction, the z-shift amount calculator 233 first selects one strip (reference strip) from the plurality of strips corresponding to the volume with the xy-directional motion artifacts corrected. The reference strip selected in this step may be the first strip selected in the step S3 of the first time, or may be any other strip.

(S16: Selecting Registering Strip)

Next, the z-shift amount calculator 233 selects one strip (registering strip), which is different from the reference strip selected in the step S15, from the plurality of strips corresponding to the volume with the xy-directional motion artifacts corrected. The registering strip selected in this step may be the second strip selected in the step S3 of the first time, or may be any other strip.

(S17: Set Reference Sub-Volume Corresponding to Reference Strip)

Next, the z-shift amount calculator 233 sets the sub-volume corresponding to the reference strip selected in the step S15, to a reference sub-volume. Note that the en face projection image of this reference sub-volume is this reference strip.

(S18: Set Registering Sub-Volume Corresponding to Registering Strip)

Similarly, the z-shift amount calculator 233 sets the sub-volume corresponding to the registering strip selected in the step S16, to a registering sub-volume. Note that the en face projection image of this registering sub-volume is this registering strip.

(S19: Identify Overlapping Area Between Reference Sub-Volume and Registering Sub-Volume)

Next, the z-shift amount calculator 233 identifies the overlapping area (common area) between the reference sub-volume set in the step S17 and the registering sub-volume set in the step S18.

As mentioned above, there are four overlapping areas between the two sub-volumes. Among the four overlapping areas, the z-shift amount calculator 233 may identify one overlapping area or two or more overlapping areas. In the case of identifying two or more overlapping areas, the process of the following step S20 is performed on each of the two or more overlapping areas.

(S20: Calculate z-Shift Amount Between Reference Sub-Volume and Registering Sub-Volume)

Next, the z-shift amount calculator 233 calculates the z-shift amount between the reference sub-volume and the registering sub-volume based on the overlapping area between the sub-volumes identified in the step S19.

In some examples, the z-shift amount calculator 233 sets a cross section (cross section of interest) in the overlapping area identified in the step S19. The cross section of interest may be freely determined cross section of the overlapping area. Next, the z-shift amount calculator 233 constructs an image of the cross section of interest (reference cross sectional image) from the reference sub-volume, and also constructs an image of the cross section of interest (registering cross sectional image) from the registering sub-volume. Next, the z-shift amount calculator 233 analyzes the reference cross sectional image to identify an image of a predetermined site of the subject's eye E (reference image), and also analyzes the registering cross sectional image to identify an image of the same site of the subject's eye E (registering image). Next, the z-shift amount calculator 233 calculates a z coordinate of the reference image and a z coordinate of the registering image, and calculates the difference between these two z coordinates. In the present example, this difference calculated is used as a z-shift amount between the reference sub-volume and the registering sub-volume.

FIG. 9 illustrates a specific example of the z-shift amount calculation. The image 401 shows a state of the intersection between the strip 402 corresponding to the reference sub-volume and the strip 403 corresponding to the registering sub-volume. In the present example, the overlapping area shown by the white circle is focused on. The diameter of this white circle along the x direction (indicated by the dotted line) is set to a cross section of interest. The same overlapping area and the same cross section of interest are also shown in the two strips 402 and 403. The z-shift amount calculator 233 constructs an image of this cross section of interest (reference cross sectional image) 412 from the reference sub-volume corresponding to the strip 402, and also constructs an image of the same cross section of interest (registering cross sectional image) 413 from the registering sub-volume corresponding to the strip 403. Further, the z-shift amount calculator 233 analyzes the reference cross sectional image 412 to identify the z position (z coordinate) 422 of an image of the retinal surface of the subject's eye E, and also analyzes the registering cross sectional image 413 to identify the z position (z coordinate) 423 of an image of the same retinal surface. In addition, the z-shift amount calculator 233 calculates, as a z-shift amount between the reference sub-volume and the registering sub-volume, the difference Δz between the z position (z coordinate) 422 determined from the cross sectional image 412 and the z position (z coordinate) 423 determined from the cross sectional image 413.

As mentioned above, the method for calculating a z-shift amount between a reference sub-volume and a registering sub-volume is not limited to this, and may be freely selected from existing methods that uses an overlapping area(s) between the reference sub-volume and the registering sub-volume.

(S21: Save z-Shift Amount)

The z-shift amount calculated for the sub-volume pair in the step S20 is sent to the z-position history data generator 234 and saved therein. In the same manner as in the storage of the xy-shift amount (step S10), the z-position history data generator 234 may, for example, store the z-shift amount together with the time information corresponding to the sub-volume pair.

(S22: Registration Between Reference Sub-Volume and Registering Sub-Volume)

The image data corrector 236 applies registration in the z direction to the reference sub-volume and the registering sub-volume, based on the z-shift amount calculated in the step S20.

This registration is, for example, the process of adjusting the position in the z direction of the reference sub-volume and the position in the z direction of the registering sub-volume in such a manner as to eliminate (cancel) or reduce the z-shift amount Δz shown in FIG. 9, in other words, in such a manner that the image of the retinal surface in the reference cross sectional image 412 and the image of the retinal surface in the registering cross sectional image 413 are placed at the same z position (the same z coordinate).

(S23: Construct Merged Image of Reference Sub-Volume and Registering Sub-Volume)

The image data corrector 236 constructs a merged image of the reference sub-volume and the registering sub-volume whose relative positions in the z direction have been adjusted by the registration in the step S22. As a result of this, the merged image of the reference sub-volume and the registering sub-volume with relative positions adjusted in both the xy direction and the z direction, is obtained.

(S24: Have all Sub-Volumes been Processed?)

The series of processes in the steps S16 to S23 is performed on all the sub-volumes in a sequential manner in accordance with predetermined order (e.g., the order assigned to the first to N-th strips) (S24: No). In the present example, the merged image constructed in the step S23 is set to a reference strip in the next routine. By sequentially applying such a series of processes to all the sub-volumes, a merged image of all the sub-volumes is obtained (S24: Yes).

(S25: Save Merged Volume of all Sub-Volumes)

The merged image finally obtained by the above-described repetition of the steps S16 to S23, is an image whose motion artifacts in both the xy direction and the z direction have been corrected, and also an image that represents the entire area to which Lissajous scanning has been applied in the step S1. The main controller 211 stores this final merged image in the memory 212 (and/or other storage devices).

The following process is designed to improve the performance (e.g., accuracy, precision, fineness) of motion artifact correction in the z-direction. While the processes of the steps S15 to S24 perform motion artifact correction in the z direction for individual sub-volumes (individual strips), the processes of the following steps S26 to S31 perform motion artifact correction in the z direction for individual cycles.

This cycle-by-cycle motion artifact correction is executed by the data processor 230 (for example, by the image data corrector 236).

Fine z-directional motion artifact correction (fine axial motion correction) does not have to be performed for individual cycles, but may be performed for individual groups of cycles included in a sub-volume. Also, fine z-directional motion artifact correction does not need to be performed for all cycles (all cycle groups), but may be performed only for a subset of all cycles (a subset of all cycle groups).

(S26: Select Cycle from Merged Volume)

The image data corrector 236 selects one cycle from the merged volume of all the sub-volumes. That is, the image data corrector 236 selects partial data corresponding to one cycle from the merged volume of all the sub-volumes.

A cycle selected in the step S26 of the first time may be freely determined. For example, in repetitive execution of the step S26, cycles may be selected in a sequential manner in accordance with the scan order (chronological order) of the plurality of cycles in the Lissajous scanning of the step S1. Alternatively, order of selecting cycles may be determined based on order assigned to the plurality of strips (the plurality of sub-volumes).

(S27: Remove Cycle from Merged Volume)

Next, the image data corrector 236 removes (extracts, draw out, eliminate) the partial data corresponding to the cycle selected in the step S26, from the merged volume of all the sub-volumes.

(S28: Calculate z-Shift Amount Between Merged Volume with Cycle Removed and Cycle)

Next, the image data corrector 236 calculates the z-shift amount between: the partial data corresponding to the cycle extracted in the step S27; and the merged volume of all the sub-volumes from which the cycle has been removed.

The method of calculating the z-shift amount in the present step S28 may be the same as the method in the step S20. In some examples of the present step S28, the image data corrector 236 analyzes the partial data of the cycle removed from the merged volume in the step S27 (the partial data is referred to as a cross sectional image of interest) to identify an image of a predetermined site of the subject's eye E, and also analyzes the merged volume from which the cross sectional image of interest has been removed, to identify an image of the same site of the subject's eye E. Here, the image identified from the partial data is referred to as a first image, and the image identified from the merged volume with the cross sectional image of interest removed is referred to as a second image. The analysis for identifying the second image does not have to be applied to the entire region of the merged volume with the cross sectional image of interest removed. For example, the analysis for identifying the second image may be applied only to a partial region adjacent to (near) the cross sectional image of interest (adjacent cycles, neighboring cycles). Further, the image data corrector 236 calculates a z coordinate of the first image and a z coordinate of the second image, and then calculates the difference between these two z coordinates. In the present example, the difference calculated in this way is used as the z-shift amount between this cycle and the merged volume with this cycle removed.

(S29: Update z-Shift Amount)

Next, the z-position history data generator 234 replaces the z-shift amount calculated in the step S20 with the z-shift amount newly calculated in the step S28. With this, the z-shift amount of the sub-volume including the partial data corresponding to the cycle extracted in the step S27 is updated.

(S30: Registration and Merging)

Next, the image data corrector 236 performs registration between the partial data corresponding to the cycle extracted in the step S27 and the merged volume with this cycle removed. This registration is performed in such a manner as to eliminate (cancel) or reduce the z-shift amount calculated in the step S28. In addition, the image data corrector 236 constructs a merged image between the partial data, and the merged volume with this cycle removed. Note that relative position adjustment in the z-direction between this partial data and this merged volume has been performed by this registration. In this way, the registration and merging of the present step S30 generates a volume on which relative position correction in the xy direction has been performed as well as fine relative position correction in the z direction has been performed.

(S31: Have all Cycles been Processed?)

The series of processes of the steps S26 to S30 is performed on all the cycles in a sequential manner in accordance with predetermined order (S31: No). By sequentially applying this series of processes to all the cycles, a volume with relative position adjustment in the z direction between all the cycles is obtained (S31: Yes). The main controller 211 may store this final volume in the memory 212 (and/or other storage devices).

(S32: Generate Visualization Data)

Next, the visualization data generator 235 generates visualization data based on the volume constructed in the step S30. Note that in aspect examples where the processes of the steps S26 to S31 are not performed or in any other aspect examples, the visualization data generator 235 may generate visualization data based on the volume saved in the step S25. In some aspect examples, the visualization data generator 235 may generate visualization data based on the volume saved in the step S14.

FIG. 10A to FIG. 10D show several specific examples of the visualization data generated in the present step S32. The visualization data generated in the present step S32 is not limited to these examples.

Figure 10A:
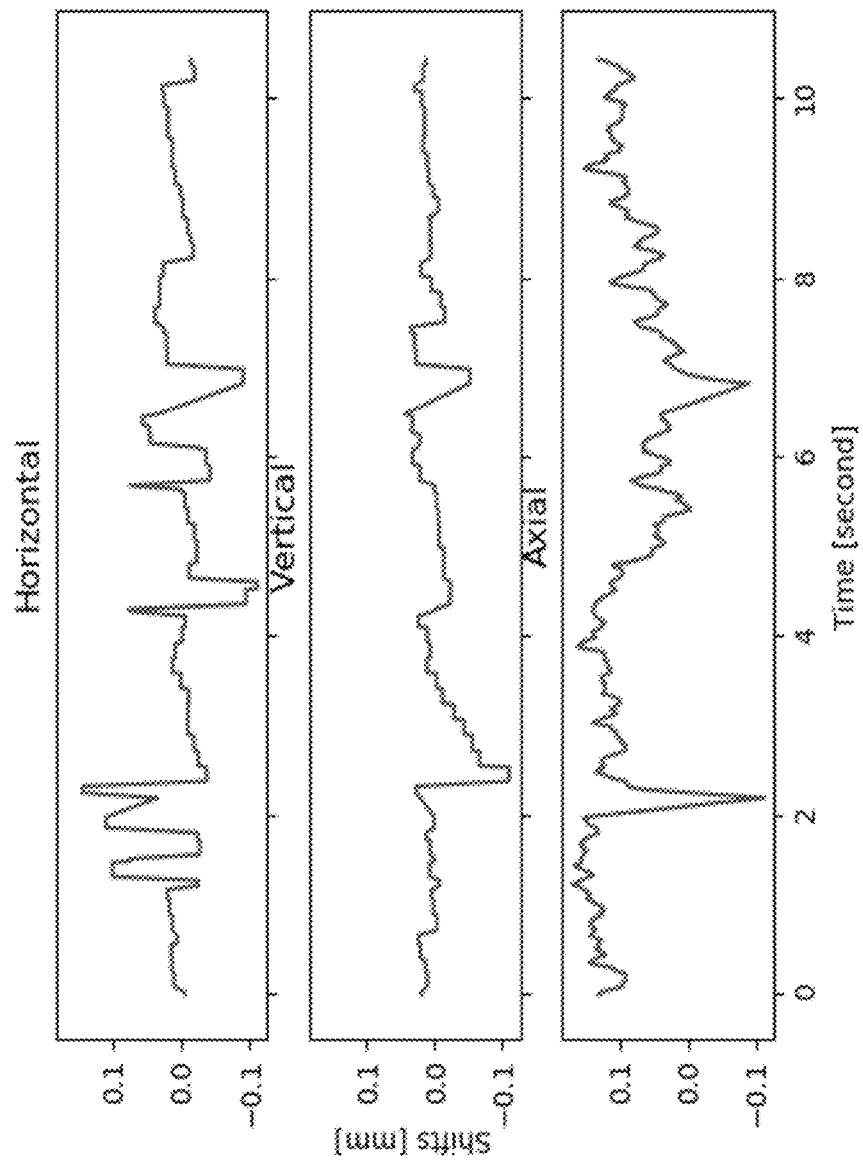
FIG. 10A illustrates a description of an example of the operation of an ophthalmic examination apparatus according to the present disclosure.

FIG. 10A shows several examples of the temporal profile (time profile) of the shift (motion) of the subject's eye E that occurred during the period of time while the Lissajous scanning of the step S1 was being performed. The upper graph shows an example of the time-dependent change (temporal change, chronological change) in the shift in the horizontal direction (x direction), that is, an example of the time-dependent change in the horizontal shift of the subject's eye E or the x-directional component of the three-dimensional motion of the subject's eye E. The middle graph shows an example of the time-dependent change (temporal change, chronological change) in the shift in the vertical direction (y direction), that is, an example of the time-dependent change in the vertical shift of the subject's eye E or the y-directional component of the three-dimensional motion of the subject's eye E. The lower graph shows an example of the time-dependent change (temporal change, chronological change) in the shift in the axial direction (z direction), that is, an example of the time-dependent change in the axial-directional shift of the subject's eye E or the z-directional component of the three-dimensional motion of the subject's eye E. In each of the graphs, the shift amount at the start of measurement is used as a reference (i.e., the shift amount is set to zero at the start of measurement). These graphs in FIG. 10A are examples of the first graph data described above.

Figure 10B:
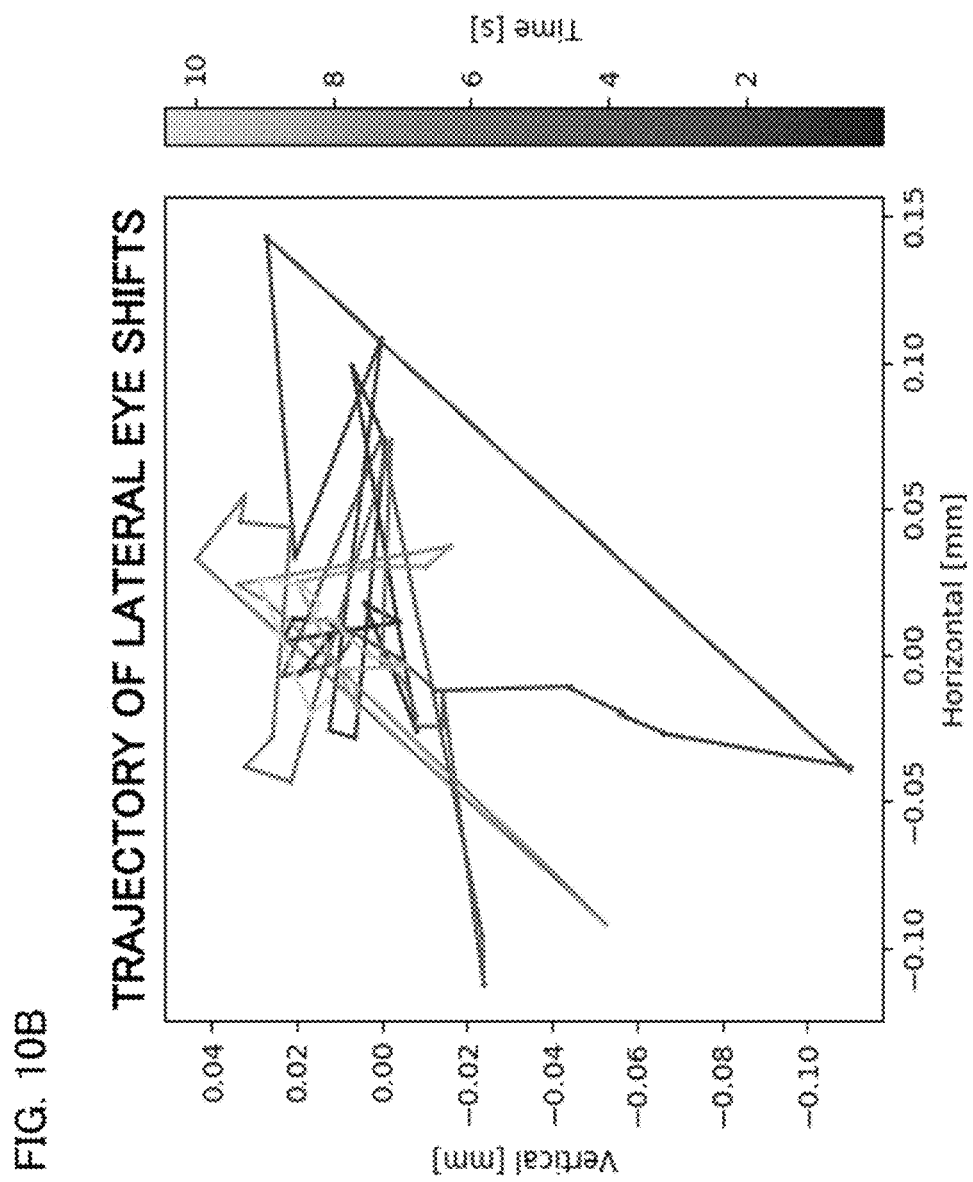
FIG. 10B illustrates a description of an example of the operation of an ophthalmic examination apparatus according to the present disclosure.

FIG. 10B shows an example of the trajectory of the shift (motion) of the subject's eye E in the xy direction (lateral direction) that occurred during the period of time while the Lissajous scanning of the step S1 was being performed. This graph is generated, for example, by combining the upper graph data and the middle graph data in FIG. 10A. The horizontal axis of the graph of FIG. 10B shows horizontal positions (x coordinates), and the vertical axis shows vertical positions (y coordinates). The present example represents time information by colors of individual points on the graph. A color code that shows the correspondence between time (time points) and colors is attached to the graph. The way of representing time information is not limited to such representation by colors. For example, time information may be represented using patterns, thicknesses, gradations, or any other aspects. The graph in FIG. 10B is an example of the second graph data described above.

Figure 10C:
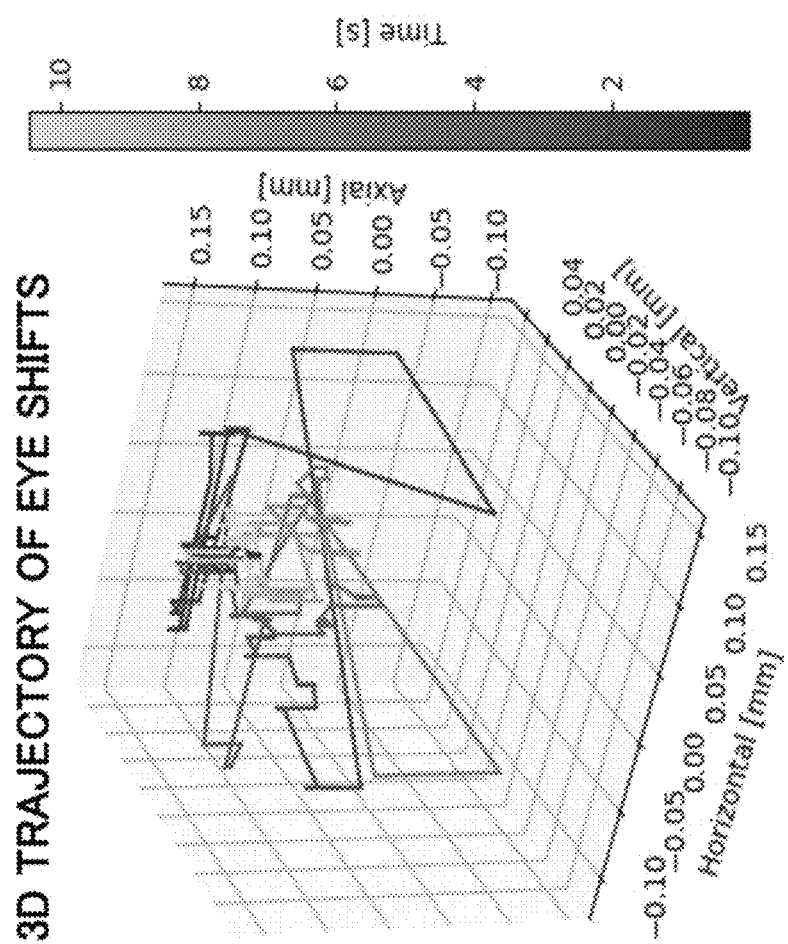
FIG. 10C illustrates a description of an example of the operation of an ophthalmic examination apparatus according to the present disclosure.

FIG. 10C shows an example of the three-dimensional trajectory of the shift (motion) of the subject's eye E that occurred during the period of time while the Lissajous scanning of the step S1 was being performed. This graph is generated, for example, by combining all of the three pieces of graph data in FIG. 10A. As in the example of FIG. 10B, the present example represents time information by colors of individual points on the graph. The way of representing time information may be the same as the graph data in FIG. 10B. The graph in FIG. 10C is an example of the third graph data described above.

Figure 10D:
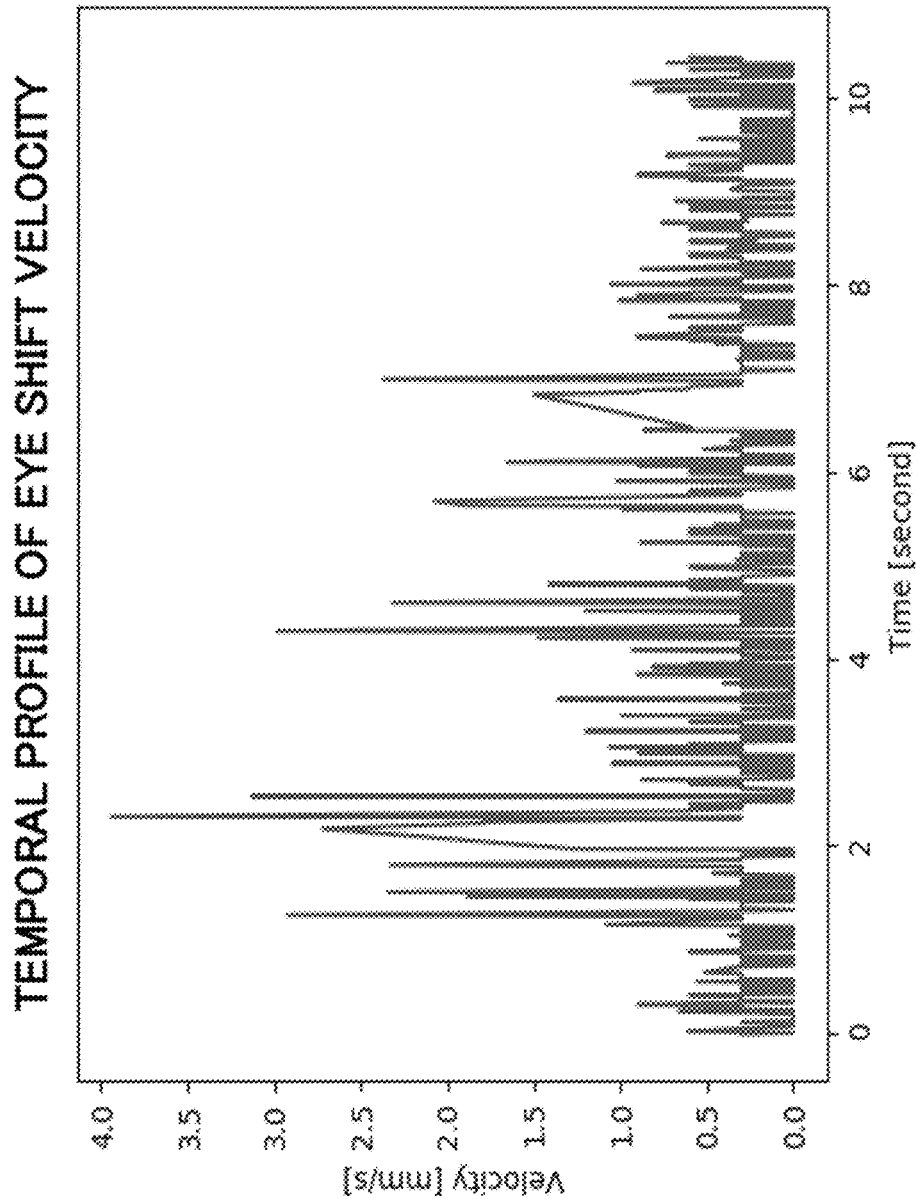
FIG. 10D illustrates a description of an example of the operation of an ophthalmic examination apparatus according to the present disclosure.

FIG. 10D shows an example of the temporal profile (time profile) of the velocity of the shift (motion) of the subject's eye E that occurred during the period of time while the Lissajous scanning of the step S1 was being performed. This graph is an example of the fourth graph data described above.

(S33: Save Visualization Data)

The main controller 211 stores the visualization data generated in the step S32 in the memory 212 (and/or other storage devices).

(S34: Generate Evaluation Data)

Next, the evaluation data generator 237 generates evaluation data based on the volume constructed in the step S30 and/or the visualization data generated in the step S32. In some examples, the evaluation data generator 237 may generate evaluation data based on, in place of the volume constructed in the step S30, the volume saved in the step S25, the volume saved in the step S14, or any other data.

For example, in the case of performing blink detection while performing the Lissajous scanning in the step S1, the evaluation data generator 237 may be configured to analyze blink data acquired by the blink detection, the three pieces of graph data of FIG. 10A, and the graph data of FIG. 10D, thereby judging whether the motion artifact correction performed in the present example is successful or unsuccessful, and/or estimating success probability (reliability) of the motion artifact correction performed in the present example. In other words, the evaluation data generator 237 may be configured to conduct judgement on whether the imaging using Lissajous scanning is successful or not, and/or estimation of success probability (reliability) of the imaging using Lissajous scanning.

In the case of performing blink detection while performing Lissajous scanning in the step S1, the evaluation data generator 237 may be configured to performs integration calculation of blink data acquired by the blink detection to calculate the total blinking time during Lissajous scanning, and apply frequency analysis to the three pieces of graph data of FIG. 10A to determine the value of a predetermined parameter such as amplitude, frequency, and any other parameters. In addition, the evaluation data generator 237 may be configured to input one or more features, such as the total blinking time, amplitude, frequency, and/or any other parameters, into a support vector machine, thereby performing judgement on whether the imaging using Lissajous scanning is successful or not, and/or estimation of success probability (reliability) of the imaging using Lissajous scanning.

In some aspect examples, the evaluation data generator 237 may be configured to conduct judgement on whether the imaging using Lissajous scanning is successful or not, and/or estimation of success probability (reliability) of the imaging using Lissajous scanning by inputting the graph data of FIG. 10C into a neural network, such as a convolutional neural network, that has been trained by machine learning using training data that includes labels of success or failure.

(S35: Save Evaluation Data)

The main controller 211 stores the evaluation data generated in the step S34 in the memory 212 (and/or other storage devices).

(S36: Display Information)

The main controller 211 displays information acquired in the present operation example on the display device 241 (END). The information displayed in the present step S36 may include any kinds of information such as one or more of the following examples or any other information: an image created from the volume saved in the step S14; an image created from the volume saved in the step S25; an image created from the volume constructed in the step S30; information created based on the visualization data generated in the step S32 (e.g., graph); information created based on the evaluation data generated in the step S34 (e.g., success or failure of imaging, success probability, reliability, confidence level); and an image acquired by the fundus camera unit 2.

As described above, the ophthalmic examination apparatus 1 applies optical scanning (e.g., Lissajous scanning) of a two-dimensional pattern to the subject's eye E to acquire a data set. This two-dimensional pattern includes a series of cycles that intersects each other. The acquired data set may include data collected by the optical scanning and/or any data generated from this collected data. Based at least on the acquired data set, the ophthalmic examination apparatus 1 generates position history data that represents a temporal change in the position of the subject's eye E.

Conventional three-dimensional OCT scanning (raster scan) cannot measure eye motions. Conventional techniques for measuring eye movements include techniques by means of Purkinje images, techniques by means of search coils, and techniques by means of eye fundus images obtained by fundus cameras or SLOs. However, these conventional techniques have the problem of low accuracy.

Eye movement evaluation devices (referred to as eye trackers), which have been attracting attention in recent years, use a stereo camera to photograph a subject's eye and evaluate eye movements based on the position of the pupil in the images obtained by the stereo camera. Such eye trackers also have the problem of low accuracy.

In contrast, the ophthalmic examination apparatus 1 is capable of conducting measurement and evaluation of eye movements (eye motions) with very high accuracy (of micrometer order, of micrometer scale) by using optical scanning of the two-dimensional pattern including the series of cycles that intersects each other, for example, by using OCT Lissajous scanning. In addition to measurement and evaluation of eye movements, the ophthalmic examination apparatus 1 is capable of providing images with motion artifacts corrected.

Several examples of features of the ophthalmic examination apparatus 1 will be described below.

The ophthalmic examination apparatus 1 may be configured to generate evaluation data based on the position history data of the subject's eye E. The evaluation data may include reliability evaluation data of a predetermined process. For example, the ophthalmic examination apparatus 1 may construct a plurality of pieces of image data (e.g., data collected by the optical scanning, volume, strip) based on the data set collected by the optical scanning, perform relative position correction (motion artifact correction) of the plurality of pieces of image data constructed, and generate reliability evaluation data of this relative position correction.

The ophthalmic examination apparatus 1 may include an inference model. The inference model is trained by machine learning using training data that includes position history data representing a temporal change in a position of an eye and/or processed data (e.g., frequency analysis data) generated by processing this position history data. The inference model receives, as an input, position history data and/or processed data of this history data, and generates reliability as an output. The ophthalmic examination apparatus 1 inputs the position history data of the subject's eye E and/or the processed data of this position history data to the inference model configured in this manner. Upon receiving this input data, the inference model generates and outputs reliability. This reliability output from the inference model may be included in the reliability evaluation data of the relative position correction.

The training data used for the machine learning of the inference model may further include data of a predetermined item acquired from an eye (e.g., blink data). If this is the case, the inference model receives, as an input, position history data and/or processed data generated from this position history data as well as data of the predetermined item and/or processed data generated by processing this data (e.g., integration data of blink data), and generates reliability as an output. The ophthalmic examination apparatus 1 inputs the data of the predetermined item for the subject's eye E and/or processed data generated from this data as well as the position history data of the subject's eye E and processed data of this position history data, to the inference model. Upon receiving this input data, the inference model outputs reliability. The reliability evaluation data of the relative position correction in the present example may include the reliability output from the inference model.

Without the use of machine learning technology, the ophthalmic examination apparatus 1 may be configured to generate evaluation data based on data of the subject's eye E on a predetermined item and the position history data of the subject's eye E.

The ophthalmic examination apparatus 1 may be configured to generate evaluation data based on time series data acquired from the subject and the position history data of the subject's eye E. The time series data may include data that represents a temporal change in the position of the head of the subject.

The ophthalmic examination apparatus 1 may be configured to correct the position history data of the subject's eye E based on time series data acquired from the subject. The time series data may include data that represents a temporal change in the position of the head of the subject.

The ophthalmic examination apparatus 1 may be configured to generate visualization data of the temporal change in the position of the subject's eye E. The visualization data may be any data that can be used for visualization such as display, printing, or any other methods.

The visualization data may include graph data that represents the temporal change in the position of the subject's eye E. The graph data may include graph data that represents a temporal change in a predetermined direction component (e.g., x-directional component, y-directional component, z-directional component) of the position of the subject's eye E defined by a predetermined coordinate system. This graph data is referred to as first graph data. The graph data included in the visualization data may include graph data that represents a temporal change in a two-dimensional position of the subject's eye E defined by a predetermined two-dimensional coordinate system (e.g., xy coordinate system, yz coordinate system, zx coordinate system). This graph data is referred to as second graph data. The graph data included in the visualization data may include graph data that represents a temporal change in a three-dimensional position of the subject's eye E defined by a predetermined three-dimensional coordinate system (e.g., xyz coordinate system). This graph data is referred to as third graph data. The graph data included in the visualization data may include graph data that represents a temporal change in a velocity of the subject's eye E. This graph data is referred to as fourth graph data.

The ophthalmic examination apparatus 1 may be configured to construct first image data corresponding to a first cycle group that includes a plurality of consecutive cycles (first consecutive cycles) among the series of cycles of the optical scanning, based on the data set acquired by the optical scanning, and also construct second image data corresponding to a second cycle group that includes a plurality of other consecutive cycles (second consecutive cycles different from the first consecutive cycles) among the series of cycles of the optical scanning, based on the data set acquired by the optical scanning. The first image data and the second image data may be, for example, sub-volumes used for strip construction (projection), or data used for sub-volume construction. In addition, the ophthalmic examination apparatus 1 may be configured to calculate a displacement of the subject's eye E between a first time point corresponding to the first cycle group and a second time point corresponding to the second cycle group, based on an overlapping area of the first image data and the second image data, and also generate the position history data of the subject's eye E based on the displacement calculated.

The first image data may be three-dimensional image data (sub-volume) defined by a predetermined three-dimensional coordinate system (e.g., xyz coordinate system), and the second image data may be three-dimensional image data (sub-volume) defined by the predetermined three-dimensional coordinate system (e.g., xyz coordinate system). If this is the case, the ophthalmic examination apparatus 1 may be configured to construct first projection image data by projecting the first image data in a first direction (e.g., z direction) along a first coordinate axis (e.g., z axis) of the predetermined three-dimensional coordinate system (e.g., xyz coordinate system), construct second projection image data by projecting the second image data in the first direction (e.g., z direction), and calculate a displacement of the subject's eye E in a second direction (e.g., xy direction, direction defined by an x coordinate and a y coordinate)

perpendicular to the first direction (e.g., z direction) based on the first projection image data and the second projection image data. The first projection image data and the second projection image data may be strips or data used to generate strips.

The ophthalmic examination apparatus 1 may be configured to perform registration between the first image data and the second image data in such a manner as to eliminate (cancel) (or reduce) the displacement of the subject's eye E in the second direction (e.g., xy direction). After this registration, the ophthalmic examination apparatus 1 may calculate a displacement of the subject's eye E in the first direction (e.g., z direction) by comparing the following pieces of image data with each other: the first image data, or image data oriented along the first direction (e.g., z direction) generated from the first image data (e.g., cross sectional image, partial three-dimensional image, A-scan image, data used for A-scan image construction, or any other data); and the second image data or image data oriented along the first direction (e.g., z direction) generated from the second image data (e.g., cross sectional image, partial three-dimensional image, A-scan image, data used for A-scan image construction, or any other data). Further, the ophthalmic examination apparatus 1 may generate the position history data of the subject's eye E based on the displacement of the subject's eye E in the first direction and the displacement of the subject's eye E in the second direction.

The first image data may be three-dimensional image data (sub-volume) defined by a predetermined three-dimensional coordinate system (e.g., xyz coordinate system), and the second image data may be three-dimensional image data (sub-volume) defined by the predetermined three-dimensional coordinate system (e.g., xyz coordinate system). A first coordinate axis of this predetermined three-dimensional coordinate system may define a first direction (e.g., z direction). The ophthalmic examination apparatus 1 may be configured to calculate the displacement of the subject's eye E through the process of calculating a displacement of the subject's eye E in the first direction by comparing the first image data or image data oriented along the first direction generated from the first image data with the second image data or image data oriented along the first direction generated from the second image data.

The predetermined three-dimensional coordinate system mentioned above may be an orthogonal coordinate system defined by the above-mentioned first coordinate axis, a second coordinate axis, and a third coordinate axis. The first coordinate axis may correspond to a direction along which probe light (e.g., measurement light LS) of the optical scanning is incident on the subject's eye E. Also, the two-dimensional pattern of the optical scanning may be defined by the second coordinate axis and the third coordinate axis (e.g., x axis and y axis).

The embodiment examples described above provide an ophthalmic data processing apparatus that includes data storage and a position history data generating processor. The data storage (e.g., the memory 212) stores (retains) a data set acquired by applying optical scanning of a two-dimensional pattern to a subject's eye. The two-dimensional pattern of this optical scanning includes a series of cycles that intersects each other. The position history data generating processor (e.g., the data processor 230) is configured to generate, based on the data set, position history data that represents a temporal change in a position of the subject's eye.

The embodiment examples described above provide a method of controlling an ophthalmic data processing apparatus. This ophthalmic data processing apparatus includes one or more processors (e.g., the main controller 211, the data processor 230) and data storage (e.g., the memory 212). The method of the present aspect includes the step of controlling the processor(s) to store, in the data storage, a data set acquired by applying optical scanning of a two-dimensional pattern to a subject's eye, and the step of controlling the processor(s) to generate, based on this data set, position history data that represents a temporal change in a position of the subject's eye. Here, the two-dimensional pattern of the optical scanning includes a series of cycles that intersects each other.

The embodiment examples described above provide an ophthalmic examination apparatus that includes a data set acquisition unit and a position history data generating processor. The data set acquisition unit (e.g., the fundus camera unit 2, the OCT unit 100, the image data constructing unit 220) is configured to acquire a data set by applying optical scanning of a two-dimensional pattern to a subject's eye. The two-dimensional pattern of the optical scanning includes a series of cycles that intersects each other. The position history data generating processor (e.g., the data processor 230) is configured to generate, based on this data set, position history data that represents a temporal change in a position of the subject's eye.

The data set acquiring unit may include a scanner (e.g., the fundus camera unit 2, the OCT unit 100) that performs the optical scanning. The scanner may include a deflector (e.g., the optical scanner 44) configured and controlled to be capable of deflecting light in two directions that are different from each other (e.g., in the x direction and the y direction). Further, the scanner may be configured to apply the optical scanning of the two-dimensional pattern to the subject's eye by repeating the following two operations in parallel with each other (simultaneously): the operation of changing the deflection direction along (in) one direction of these two directions in a first period; and the operation of changing the deflection direction along (in) the other direction of these two directions in a second period different from the first period.

The embodiment examples described above provide a method of controlling an ophthalmic examination apparatus. This ophthalmic examination apparatus includes a scanner and a processor. The scanner of some examples is configured to apply optical scanning to a subject's eye, and corresponds to the fundus camera unit 2 and the OCT unit 100 of the embodiment example described above. The processor of some examples corresponds to the image data constructing unit 220 and the data processor 230 of the embodiment example described above. The method of the present aspect includes the step of controlling the scanner to apply optical scanning of a two-dimensional pattern to a subject's eye to collect a data set, and the step of controlling the processor to generate, based on the data set collected by the scanner, position history data that represents a temporal change in a position of the subject's eye. Here, the two-dimensional pattern of the optical scanning includes a series of cycles that intersects each other.

The scanner may include a deflector (e.g., the optical scanner 44) configured and controlled to be capable of deflecting light in two directions that are different from each other (e.g., in the x direction and the y direction). If this is the case, the method of controlling the ophthalmic examination apparatus of the present aspect may include the process of controlling the scanner to apply the optical scanning of the two-dimensional pattern to the subject's eye by repeating the following two operations in parallel with each other (simultaneously): the operation of changing the deflection direction along (in) one direction of these two directions in a first period; and the operation of changing the deflection direction along (in) the other direction of these two directions in a second period different from the first period.

The embodiment examples described above provide a program configured to cause a computer to execute any of the above-described methods of controlling an ophthalmic examination apparatus. In addition, the embodiment examples described above provide a program configured to cause a computer to execute any of the above-described methods of controlling an ophthalmic data processing apparatus. Further, the embodiment examples described above provide a program configured to cause a computer to execute any of the above-described methods of processing ophthalmic data.

The embodiment examples described above provide a computer-readable non-transitory recording medium that stores any of the above-described programs. This computer-readable non-transitory recording medium may be in any form. Examples of this computer-readable non-transitory recording medium include a magnetic disk, an optical disk, a magneto-optical disk, a semiconductor memory, and any other kinds of recording media.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide v. DIRECTV*, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method of processing ophthalmic data comprising:
preparing a data set acquired by applying optical scanning of a two-dimensional pattern to a subject's eye, the two-dimensional pattern including a series of cycles that intersects each other;
generating, based on the data set, position history data that represents a temporal change in a position of the subject's eye;
constructing a plurality of pieces of image data based on the data set;
performing relative position correction of the plurality of pieces of image data,
inputting at least one of the position history data of the subject's eye and processed data generated by processing the position history data of the subject's eye to an inference model, the inference model being trained by machine learning using training data, the training data including at least one of position history data that represents a temporal change in a position of an eye and processed data generated by processing this position history data, and the inference model being configured to receive at least one of the position history data of the subject's eye and the processed data generated by processing the position history data of the subject's eye, and to output reliability; and
generating, based on the position history data, reliability evaluation data of the relative position correction that includes the reliability output from the inference model.

2. The method of claim 1, wherein
the training data further includes data of a predetermined item acquired from an eye, and
the inference model is configured to receive at least one of the position history data of the subject's eye and the processed data generated by processing the position history data of the subject's eye, and at least one of data of the predetermined item acquired from the subject's eye and processed data generated by processing the data of the predetermined item acquired from the subject's eye, and to output reliability,
the method further comprising:
preparing the data of the predetermined item acquired from the subject's eye; and
inputting, to the inference model, at least one of the prepared data of the predetermined item acquired from the subject's eye and processed data generated by processing the prepared data, and the at least one of the position history data of the subject's eye and the processed data generated by processing the position history data of the subject's eye,
wherein the reliability evaluation data of the relative position correction includes reliability output from the inference model.

3. The method of claim 1, further comprising preparing data of a predetermined item acquired from the subject's eye,
wherein the reliability evaluation data is generated based on the position history data and the data of the predetermined item acquired from the subject's eye.

4. The method of claim 1, further comprising preparing time series data acquired from a subject,
wherein the reliability evaluation data is generated based on the position history data and the time series data acquired from the subject.

5. The method of claim 4, wherein the time series data includes data that represents a temporal change in a position of a head of the subject.

6. The method of claim 1, further comprising:
preparing time series data acquired from a subject; and
revising the position history data based on the time series data.

7. The method of claim 6, wherein the time series data includes data that represents a temporal change in a position of a head of the subject.

8. The method of claim 1, wherein the position history data includes visualization data of the temporal change in the position of the subject's eye.

9. The method of claim 8, wherein the visualization data includes graph data that represents the temporal change in the position of the subject's eye.

10. The method of claim 9, wherein the graph data includes first graph data that represents a temporal change in a predetermined direction component of the position of the subject's eye defined by a predetermined coordinate system.

11. The method of claim 9, wherein the graph data includes second graph data that represents a temporal change in a two-dimensional position of the subject's eye defined by a predetermined two-dimensional coordinate system.

12. The method of claim 9, wherein the graph data includes third graph data that represents a temporal change in a three-dimensional position of the subject's eye defined by a predetermined three-dimensional coordinate system.

13. The method of claim 9, wherein the graph data includes fourth graph data that represents a temporal change in a velocity of the subject's eye.

14. The method of claim 1, further comprising:
constructing first image data from the data set, the first image data corresponding to a first cycle group that includes a plurality of consecutive cycles among the series of cycles;
constructing second image data from the data set, the second image data corresponding to a second cycle group that includes a plurality of other consecutive cycles among the series of cycles; and
calculating a displacement of the subject's eye between a first time point corresponding to the first cycle group and a second time point corresponding to the second cycle group, based on an overlapping area of the first image data and the second image data,
wherein the position history data is generated based on the displacement.

15. The method of claim 14, wherein
the first image data is three-dimensional image data defined by a predetermined three-dimensional coordinate system and the second image data is three-dimensional image data defined by the predetermined three-dimensional coordinate system, and
calculating the displacement of the subject's eye includes:
constructing first projection image data by projecting the first image data in a first direction along a first coordinate axis of the predetermined three-dimensional coordinate system;
constructing second projection image data by projecting the second image data in the first direction; and
calculating a displacement of the subject's eye in a second direction perpendicular to the first direction based on the first projection image data and the second projection image data.

16. The method of claim 15, wherein calculating the displacement of the subject's eye further includes:
performing registration between the first image data and the second image data in such a manner as to eliminate the displacement of the subject's eye in the second direction;
calculating, after the registration, a displacement of the subject's eye in the first direction by comparing the first image data or image data along the first direction generated from the first image data with the second image data or image data along the first direction generated from the second image data; and
generating the position history data based on the displacement of the subject's eye in the first direction and the displacement of the subject's eye in the second direction.

17. The method of claim 15, wherein the predetermined three-dimensional coordinate system is an orthogonal coordinate system defined by the first coordinate axis, a second coordinate axis, and a third coordinate axis, wherein
the first coordinate axis corresponds to a direction along which probe light of the optical scanning is incident on the subject's eye, and
the two-dimensional pattern of the optical scanning is defined by the second coordinate axis and the third coordinate axis.

18. The method of claim 14, wherein
the first image data is three-dimensional image data defined by a predetermined three-dimensional coordinate system and the second image data is three-dimensional image data defined by the predetermined three-dimensional coordinate system,
a first coordinate axis of the predetermined three-dimensional coordinate system defines a first direction, and
calculating the displacement of the subject's eye includes calculating a displacement of the subject's eye in the first direction by comparing the first image data or image data along the first direction generated from the first image data with the second image data or image data along the first direction generated from the second image data.

19. The method of claim 18, wherein the predetermined three-dimensional coordinate system is an orthogonal coordinate system defined by the first coordinate axis, a second coordinate axis, and a third coordinate axis, wherein
the first coordinate axis corresponds to a direction along which probe light of the optical scanning is incident on the subject's eye, and
the two-dimensional pattern of the optical scanning is defined by the second coordinate axis and the third coordinate axis.

20. An ophthalmic data processing apparatus comprising:
data storage that stores a data set acquired by applying optical scanning of a two-dimensional pattern to a subject's eye, the two-dimensional pattern including a series of cycles that intersects each other;
a position history data generating processor configured to generate, based on the data set, position history data that represents a temporal change in a position of the subject's eye;
an image data constructing processor configured to constructing a plurality of pieces of image data based on the data set;
a position correcting processor configured to perform relative position correction of the plurality of pieces of image data; and
an evaluation data generating processor configured to generate reliability evaluation data of the relative position correction based on the position history data, wherein
the evaluation data generating processor inputs at least one of the position history data of the subject's eye and processed data generated by processing the position history data of the subject's eye to an inference model, the inference model being trained by machine learning using training data, the training data including at least one of position history data that represents a temporal change in a position of an eye and processed data generated by processing this position history data, and the inference model being configured to receive at least one of the position history data of the subject's eye and the processed data generated by processing the position history data of the subject's eye, and to output reliability, and
the reliability evaluation data evaluation generated by the data generating processor includes the reliability output from the inference model.

21. An ophthalmic examination apparatus comprising:
a data set acquisition unit configured to acquire a data set by applying optical scanning of a two-dimensional pattern to a subject's eye, the two-dimensional pattern including a series of cycles that intersects each other;

a position history data generating processor configured to generate, based on the data set, position history data that represents a temporal change in a position of the subject's eye;

an image data constructing processor configured to constructing a plurality of pieces of image data based on the data set;

a position correcting processor configured to perform relative position correction of the plurality of pieces of image data; and an evaluation data generating processor configured to generate reliability evaluation data of the relative position correction based on the position history data, wherein the evaluation data generating processor inputs at least one of the position history data of the subject's eye and processed data generated by processing the position history data of the subject's eye to an inference model, the inference model being trained by machine learning using training data, the training data including at least one of position history data that represents a temporal change in a position of an eye and processed data generated by processing this position history data, and the inference model being configured to receive at least one of the position history data of the subject's eye and the processed data generated by processing the position history data of the subject's eye, and to output reliability, and the reliability evaluation data evaluation generated by the data generating processor includes the reliability output from the inference model.

\* \* \* \* \*